US009517319B2

United States Patent
Omura et al.

(10) Patent No.: US 9,517,319 B2
(45) Date of Patent: Dec. 13, 2016

(54) WEARING TOOL FOR BREATHING MASK, AND BREATHING MASK

(75) Inventors: Keiko Omura, Hino (JP); Shinya Fujimoto, Ibaraki (JP); Akito Nishijima, Ibaraki (JP)

(73) Assignee: Teijin Pharma Limited, Tokyo (JP)

( * ) Notice: Subject to any disclaimer, the term of this patent is extended or adjusted under 35 U.S.C. 154(b) by 721 days.

(21) Appl. No.: 13/130,709

(22) PCT Filed: Nov. 26, 2009

(86) PCT No.: PCT/JP2009/006376
§ 371 (c)(1),
(2), (4) Date: May 23, 2011

(87) PCT Pub. No.: WO2010/061599
PCT Pub. Date: Jun. 3, 2010

(65) Prior Publication Data
US 2011/0247627 A1    Oct. 13, 2011

(30) Foreign Application Priority Data
Nov. 27, 2008    (JP) ................................. 2008-302362

(51) Int. Cl.
*A61M 16/06*    (2006.01)

(52) U.S. Cl.
CPC ..... *A61M 16/0683* (2013.01); *A61M 16/0622* (2014.02); *A61M 16/06* (2013.01);
(Continued)

(58) Field of Classification Search
CPC ........... A61F 11/00; A61F 11/06; A61F 11/08; A61F 11/12; A61F 11/14; A42B 3/16; A42B 3/166; A61M 16/06; A61M 16/0683; A61M 2016/0633; A61M 2210/0662; A62B 18/084; A41D 13/1161
(Continued)

(56) References Cited

U.S. PATENT DOCUMENTS 879,048 A * 2/1908 Hibbler ........................... 30/318
975,581 A * 11/1910 Stevens ........................... 403/93
(Continued)

FOREIGN PATENT DOCUMENTS

| CN | 2149738 Y | 12/1993 |
|---|---|---|
| CN | 1173810 A | 2/1998 |

(Continued)

OTHER PUBLICATIONS

Russian Office Action for corresponding Application No. 2011126187 mailed Nov. 14, 2013, 6 pages.
(Continued)

*Primary Examiner* — Justine Yu
*Assistant Examiner* — Michael Tsai
(74) *Attorney, Agent, or Firm* — Sughrue Mion, PLLC

(57) ABSTRACT

For reducing a discomfort feeling brought by wearing a breathing mask, a wearing tool for the breathing mask which covers nostrils of a user and supplies gas for breathing to the nostrils comprises a pair of connecting members each of which has a longitudinal shape and has a first end portion which is connected to the breathing mask, and a pair of fixing members each of which is connected to a second end portion of the fixing member and is plugged in the tragus of the user. Hence a discomfort feeling due to restraining around the head of the user can be reduced.

34 Claims, 33 Drawing Sheets

(52) U.S. Cl.
CPC ... *A61M 16/0666* (2013.01); *A61M 2209/088* (2013.01); *A61M 2210/0618* (2013.01); *A61M 2210/0662* (2013.01)

(58) Field of Classification Search
USPC .... 128/866, 207.11, 206.13; 2/13, 209, 423, 2/422, 452; 181/129; 351/158; 403/61, 403/84, 204, 309, 408.1, 93–95, 98
See application file for complete search history.

(56) References Cited

U.S. PATENT DOCUMENTS

| | | | |
|---|---|---|---|
| 1,308,815 A * | 7/1919 | Simon | 403/95 |
| 2,133,699 A | 3/1937 | Heidbrink | |
| 2,430,229 A | 11/1947 | Kelsey | |
| 2,946,394 A * | 7/1960 | Smith | 181/135 |
| 2,954,027 A * | 9/1960 | Marasco | 128/206.28 |
| 3,297,832 A * | 1/1967 | Bernard | 381/327 |
| 3,747,599 A * | 7/1973 | Malmin | 128/201.12 |
| 3,983,336 A * | 9/1976 | Malek et al. | 381/313 |
| 4,179,590 A | 12/1979 | Snow | |
| 4,465,067 A | 8/1984 | Koch et al. | |
| 4,668,842 A | 5/1987 | Yokoyama et al. | |
| 5,284,469 A * | 2/1994 | Jasen et al. | 602/17 |
| 5,544,253 A | 8/1996 | Nagayoshi et al. | |
| 5,659,156 A | 8/1997 | Mauney et al. | |
| 5,697,363 A | 12/1997 | Hart | |
| 5,724,965 A | 3/1998 | Handke et al. | |
| 6,176,576 B1 * | 1/2001 | Green et al. | 351/123 |
| 6,467,482 B1 | 10/2002 | Boussignac | |
| 6,578,576 B1 * | 6/2003 | Taormina et al. | 128/207.17 |
| 6,690,807 B1 * | 2/2004 | Meyer | 381/327 |
| 6,728,974 B2 * | 5/2004 | Wadsworth | 2/456 |
| 7,313,246 B2 * | 12/2007 | Miller et al. | 381/381 |
| 2002/0014241 A1 | 2/2002 | Gradon et al. | |
| 2003/0150459 A1 | 8/2003 | Campbell | |
| 2003/0150460 A1 * | 8/2003 | Campbell et al. | 128/206.13 |
| 2003/0174853 A1 | 9/2003 | Howes et al. | |
| 2003/0196655 A1 | 10/2003 | Ging et al. | |
| 2003/0196657 A1 | 10/2003 | Ging et al. | |
| 2003/0196662 A1 | 10/2003 | Ging et al. | |
| 2004/0074498 A1 | 4/2004 | Begum | |
| 2004/0139973 A1 | 7/2004 | Wright | |
| 2004/0165743 A1 | 8/2004 | Bayer | |
| 2004/0182398 A1 | 9/2004 | Sprinkle et al. | |
| 2005/0066976 A1 | 3/2005 | Wondka | |
| 2005/0076913 A1 | 4/2005 | Ho et al. | |
| 2006/0130845 A1 | 6/2006 | Schegerin | |
| 2006/0162729 A1 | 7/2006 | Ging et al. | |
| 2006/0174887 A1 | 8/2006 | Chandran et al. | |
| 2006/0225740 A1 | 10/2006 | Eaton et al. | |
| 2006/0237017 A1 * | 10/2006 | Davidson et al. | 128/205.25 |
| 2006/0272645 A1 | 12/2006 | Ging et al. | |
| 2007/0003093 A1 | 1/2007 | Ito et al. | |
| 2007/0023044 A1 | 2/2007 | Kwok et al. | |
| 2007/0062536 A1 | 3/2007 | McAuley et al. | |
| 2007/0119458 A1 | 5/2007 | Ging et al. | |
| 2007/0135717 A1 * | 6/2007 | Uenishi et al. | 600/485 |
| 2008/0041389 A2 | 2/2008 | Ging et al. | |
| 2008/0047560 A1 | 2/2008 | Veliss et al. | |
| 2008/0121235 A1 | 5/2008 | Ging et al. | |
| 2008/0196727 A1 | 8/2008 | Ho et al. | |
| 2008/0216825 A1 | 9/2008 | Singh et al. | |
| 2008/0216838 A1 | 9/2008 | Wondka | |
| 2008/0276937 A1 | 11/2008 | Davidson et al. | |
| 2009/0044808 A1 * | 2/2009 | Guney et al. | 128/206.24 |
| 2009/0145429 A1 | 6/2009 | Ging et al. | |
| 2010/0043800 A1 | 2/2010 | Omura et al. | |
| 2012/0073576 A1 | 3/2012 | Wondka | |

FOREIGN PATENT DOCUMENTS

| | | |
|---|---|---|
| CN | 2721141 Y | 8/2005 |
| CN | 1681553 A | 10/2005 |
| CN | 1784252 A | 6/2006 |
| CN | 1893731 A | 1/2007 |
| CN | 1905917 A | 1/2007 |
| CN | 101238047 A | 8/2008 |
| DE | 3215466 A1 | 11/1983 |
| DE | 29718483 U1 | 2/1999 |
| EP | 1780580 A1 | 5/2007 |
| GB | 2336692 A | 10/1999 |
| JP | 59-221199 A | 12/1984 |
| JP | 1-22311 Y | 6/1989 |
| JP | 1-171418 U | 12/1989 |
| JP | 9-10311 A | 1/1997 |
| JP | 2-77052 U | 6/1999 |
| JP | 2000-508562 A | 7/2000 |
| JP | 2001-231860 A | 8/2001 |
| JP | 200252082 A | 2/2002 |
| JP | 2004-570 A | 1/2004 |
| JP | 2004-572 A | 1/2004 |
| JP | 2006-68471 A | 3/2006 |
| JP | 2007-518456 A | 7/2007 |
| JP | 2008-119239 A | 5/2008 |
| JP | 2004-209061 A | 7/2011 |
| TW | 242214 B | 3/1995 |
| WO | 9623443 A1 | 8/1996 |
| WO | 2004022146 A1 | 3/2004 |
| WO | 2007146844 A2 | 12/2007 |
| WO | 2008010484 A1 | 1/2008 |
| WO | 2008011682 A1 | 1/2008 |

OTHER PUBLICATIONS

International Search Report dated Mar. 16, 2010 for PCT/JP2009/006376.
Written Opinion for PCT/JP2009/006376 dated Mar. 16, 2010 English Translation.
Communication dated Mar. 18, 2014 from the State Intellectual Property Office, P.R. China in counterpart Chinese Application No. 200980147592.7.
Communication dated Jul. 1, 2014 from the European Patent Office in counterpart European Patent Application No. 09828849.1.
Communication dated Aug. 21, 2014 from the Chinese Patent Office in counterpart Chinese Patent Application No. 200980147592.7.
Office Action dated Oct. 10, 2014, for the corresponding Australian Patent Application No. 2009321054.

* cited by examiner

Lateral View　　　　Front View

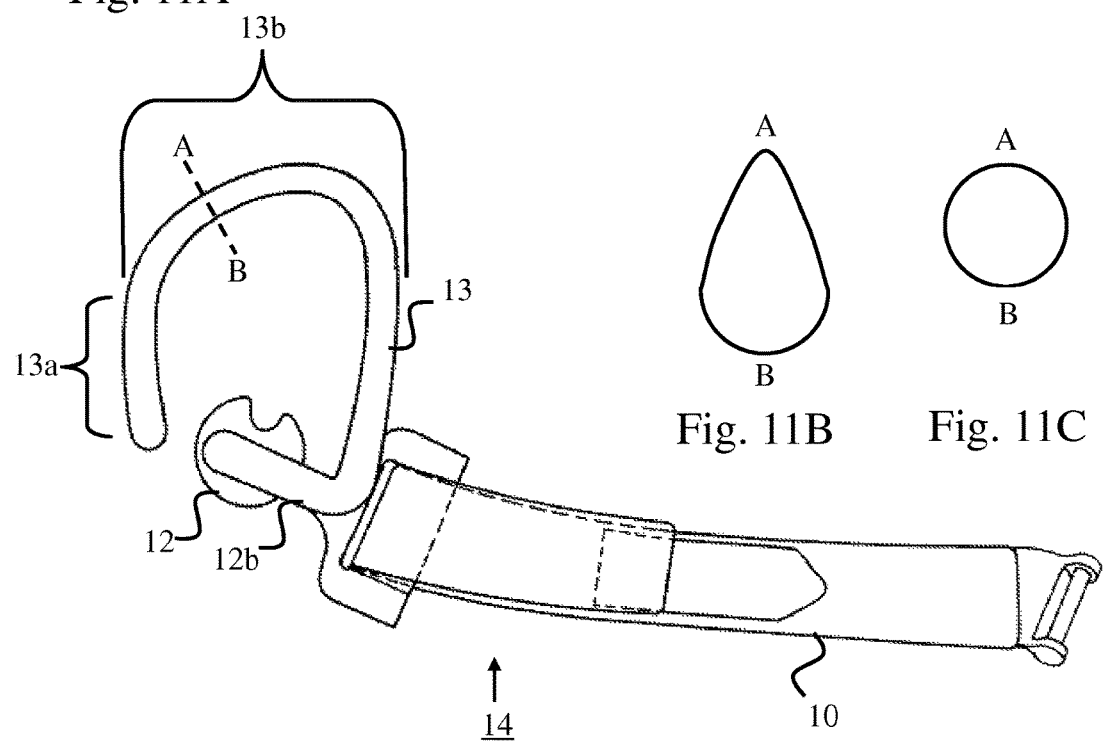
Fig. 11A
Fig. 11B
Fig. 11C
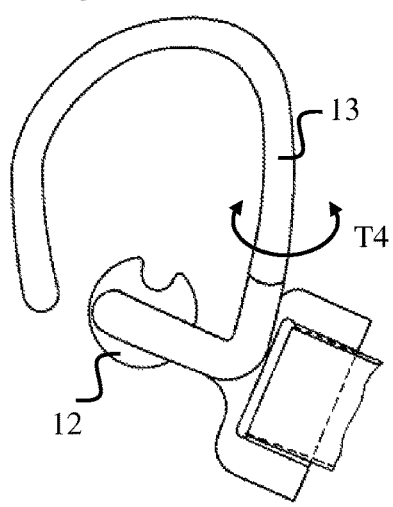
Fig. 11D
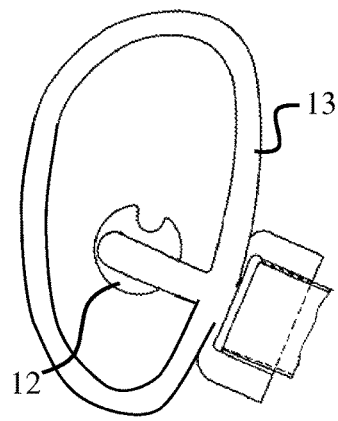
Fig. 11E

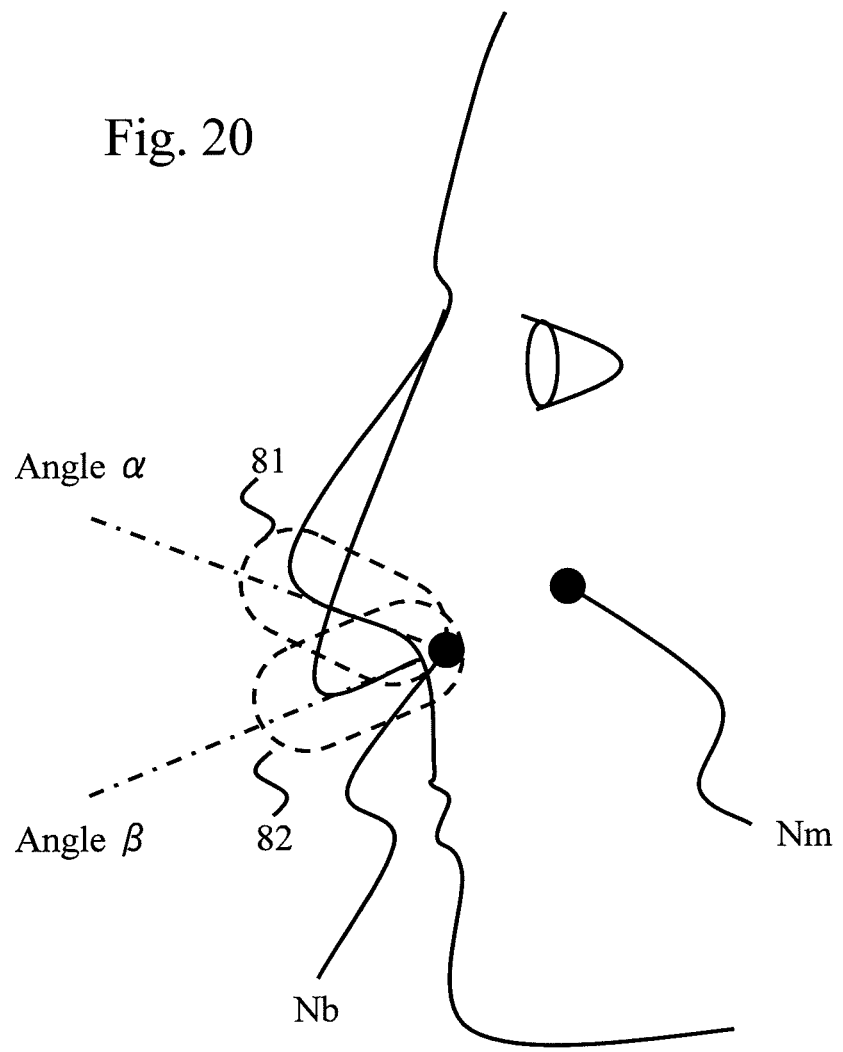

Lateral View

Front View

WEARING TOOL FOR BREATHING MASK, AND BREATHING MASK

CROSS REFERENCE TO RELATED APPLICATIONS

This application is a National Stage of International Application No. PCT/JP2009/006376 filed Nov. 26, 2009, claiming priority based on Japanese Patent Application No. 2008-302362, filed Nov. 27, 2008, the contents of all of which are incorporated herein by reference in their entirety.

FIELD OF THE INVENTION

The present invention relates to a breathing mask which covers a user's nostrils and supplies pressurized gas for breathing to the nostrils, and to a wearing tool for the breathing mask.

BACKGROUND OF THE INVENTION

As a treatment method for sleep apnea syndrome, such that an airway is obstructed and becomes apnea during sleep, CPAP (Continuous Positive Airway Pressure) treatment is known, in which gas for breathing pressurized in the range from 392 to 1961 Pa is continuously supplied to the nostrils of a patient when sleeping, so that the airway of the patient is expanded, and thus the patient breathing is assisted.

For CPAP treatment, a breathing gas supply apparatus is used, which has a function for generating gas for breathing by pressurizing the air. Gas for breathing generated by the breathing gas supply apparatus is supplied through a flexible hose to a breathing mask. The breathing mask, as an example is described in Patent Document 1, is configured to cover the nostrils of the patient who uses the breathing mask (hereinafter, the "user"). And the user is supplied with gas for breathing by wearing the breathing mask when sleeping.

To achieve the intended effect of therapy by CPAP treatment, it is important to ensure that gas for breathing does not leak out of the breathing mask. Therefore, it is required that the breathing mask be in close contact with the environs of the nostrils and fixed in that condition for a long term. To meet such a requirement, various methods have been proposed. For example, in Patent Document 1 and Patent Document 2, a headgear-style wearing tool is described. The headgear-style wearing tool fixes the breathing mask by straps fasten around the head of the user. A cold mask-style wearing tool described in Patent Document 3 fixes the breathing mask by loop-shape elastic bands latching around ears of the user. Further, in Patent Document 2, there is a description of a breathing mask which is configured so that an angle of the above mentioned wearing tool attached to the breathing mask is adjustable. This breathing mask has an angle adjustment mechanism which is configured so that a connecting portion with the wearing tool is configured to be rotatable, and an angle of the breathing mask relative to the environs of the nostrils of the user is adjusted, and thus the degree of closeness of contact of the breathing mask is enhanced.

In addition, if humidity contained in gas for breathing or the breath of the user is condensates on the inner walls of the breathing mask and water drops drip onto the face of the user lying on the back, the user is needlessly wakened. Therefore, methods to prevent this have been proposed. For example, a breathing mask described in Patent Document 4 has outer shell (frame) which is dual structured, and a heat insulating air layer between the inner and the outer walls of the breathing mask. By this means, the temperature of the inner walls is maintained higher than the temperature of the outer walls, and the condensation is suppressed.

Further, when the user lies on the side with the breathing mask worn, if the flexible hose is crushed by his body, supply of gas for breathing is inhibited and the treatment is interfered. To prevent this, for example, there is a description of a breathing mask in Patent Document 5, which has on the frame a rotatable L-shape tube to be connected with the flexible hose. By this breathing mask, the user can direct the flexible hose to the direction such that the concern of the flexible hose being crushed under the user's body who lies on the side is smaller, and thus crushing of the flexible hose can be prevented.

PRIOR TECHNICAL DOCUMENT

Patent Document 1: Japanese Patent Application Laid-Open Publication No. H09-10311
Patent Document 2: Japanese Patent Application Laid-Open Publication No. 2004-572
Patent Document 3: Japanese Patent Application Laid-Open Publication No. 2004-209061
Patent Document 4: Japanese Patent Application Laid-Open Publication No. 2008-119239
Patent Document 5: Japanese Patent Application Laid-Open Publication No. 2004-570

SUMMARY OF THE INVENTION

However, the conventional arts described above have the following types of problems. Firstly, as for the headgear-style wearing tool described in Patent Document 1 and Patent Document 2, due to the straps pressing around the head of the user, there is the concern that a discomfort feeling such as a feeling of restraint or a feeling of pressure may occur. Secondly, as for the cold mask-style wearing tool described in Patent Document 3, due to the elastic bands biting the bases of the ears of the user, there is the concern that a discomfort feeling or a pain may occur. These discomfort feeling or pain may cause poor quality of sleep. This can cause a problem with regard to the object of CPAP treatment, that is, suppressing unnecessary and harmful awakening and raising the quality of sleep.

As for a wearing tool such as straps, when the user changes his body position while sleeping and the breathing mask or the hose are caught and pulled by the user's body or by a bedcloth, there is a case that a force is placed to twist the strap in the width direction. Then the straps are twisted, and there is the concern that the breathing mask is displaced from the environs of the nostril. This causes problems from the standpoints of therapeutic effects.

There also is the concern that the angle adjustment mechanism for adjusting the angle of the breathing mask and the wearing tool described in Patent Document 2 underlies and presses user's face when the user lies on the side, which results a discomfort feeling. Additionally, if an attempt is made to adjust the angle of the breathing mask relative to the height of the nasal bridge or the direction of the nostrils of the user while the breathing mask is worn, gaps are likely to occur at the environs of the nostrils, and thus there is the concern that it becomes necessary to wear the wearing tool again after the angle adjustment. This causes problems from the standpoints of user convenience.

Further, as for the breathing mask described in Patent Document 4, there is a problem of increase of costs for manufacturing the dual structured frame. For example, integral molding by a method with high difficulty such as blow molding leads to increase of costs. Even if a method is employed to mold the inner and the outer walls separately and to combine them, increase in the number of components and increase in the number of assembly processes entail.

And, as for the breathing mask described in Patent Document 5, manufacturing the frame and the L shaped hose separately and assembling them leads to a problem of increase of costs due to increased number of components and assembly steps. There also is the concern that the L-shape tube, because of being rotatable, may touch the forehead or lips of the user and gives the user a discomfort feeling.

Therefore, the object of the present invention is to provide a breathing mask and a wearing tool for it, which can reduce a discomfort feeling brought by wearing.

Another object of the present invention is to provide a wearing tool which can prevent displacement of the breathing mask.

Further object of the present invention is to provide a wearing tool which enables adjusting an angle of the breathing mask relative to the user's nostrils, and which can be worn easily.

Further object of the present invention is to provide at low cost a breathing mask which can suppress the condensation.

Further object of the present invention is to provide at low cost a breathing mask which can prevent interference with the supply of gas for breathing.

In order to achieve the above object, the first aspect of the present invention is a wearing tool for a breathing mask which covers nostrils of a user and supplies gas for breathing to the nostrils comprising a pair of connecting members each of which has a longitudinal shape, and has a first end portion which is connected to the breathing mask, and a pair of fixing members each of which is connected to a second end portion of the connecting member, and is plugged in a tragus of the user.

The second aspect of the present invention is a wearing tool for a breathing mask which supplies a user with gas for breathing comprising a pair of connecting members each of which has a longitudinal shape and has a first end portion which is connected to the breathing mask, and a frame portion which is connected to a second end portion of the connecting member and is placed around an ear flap of the user; the frame portion has a biasing portion which abuts and biases the base of the ear of the user.

The third aspect of the present invention is a wearing tool for a breathing mask which covers nostrils of a user and supplies pressurized gas for breathing to the nostrils comprising a pair of connecting members each of which has a longitudinal shape and has a first end portion, which is connected to the breathing mask, and which fixes the breathing mask at the environs of the nostrils of the user, and a supporting member which extends in the longitudinal direction of the connecting member, and has greater rigidity than that of the connecting member; the supporting member has a first width in the region close to the first end portion and a second width, which is greater than the first width, in the other region.

The fourth aspect of the present invention is a breathing mask which has a wearing tool comprising a pair of connecting members each of which has a longitudinal shape and has a first end portion which is connected to the breathing mask, and a pair of supporting members which are provided on the pair of connecting members and have greater rigidity than that of the pair of connecting members; each of the pair of the supporting members further comprises a first plate-shape member which is fixed at the breathing mask and a second-plate shape member which is fixed at the connecting member, and the first plate-shape member and the second plate-shape member are rotatable around a rotation axis in a position which is used as a pivot of an angle adjustment of the breathing mask when the angle adjustment of the breathing mask is performed.

The fifth aspect of the present invention is a breathing mask which covers the nostrils of the user and supplies gas for breathing to the nostrils comprising a first member which abuts the face of a user and covers the nostrils and comprises a first inhaling port which takes in gas for breathing and/or a first exhaling port which discharges breath, and a second member having a rigidity greater than that of the first member, which covers at least a portion of the first member and comprises a second inhaling port connected to a means for transport of the gas for breathing and which mates with the first inhaling port portion and/or a second exhaling port which mates with the first exhaling port portion and which is connected to the outside; a cavity is present between the first member and the second member, or the first member has water repellent properties.

The sixth aspect of the present invention is a breathing mask which covers the nostrils of a user and supplies gas for breathing to the nostrils comprising a first member which abuts the face of the user and covers the nostrils, and a second member, having greater rigidity than that of the first member, which is connected with the first member by connecting, at a prescribed position, with a transporting means of the gas for breathing; portions of the first member and the second member for connecting each other have 180 degree rotational symmetry shapes.

According to the first and the second aspect of the present invention, the breathing mask can be fixed at the environs of the nostrils of the user, and the discomfort feeling brought by wearing can be reduced.

According to the third aspect of the present invention, displacement of the breathing mask while used can be prevented, and the discomfort feeling brought by wearing can be reduced.

According to the fourth aspect of the present invention, the wearing tool for the breathing mask is provided which enables adjustment according to the structure of the nose of the user, and which can be easily worn.

According to the fifth aspect of the present invention, the breathing mask is provided at low cost which can suppress the condensation.

According to the sixth aspect of the present invention, the breathing mask is provided at low cost which can prevent interference with the supply of gas for breathing.

BRIEF DESCRIPTION OF THE DRAWINGS

FIG. 11A through FIG. 11E are drawings for explaining the third practical example of the plug 12 as the fixing member.

FIG. 20 is a drawing for explaining function of the fourth embodiment.

DESCRIPTION OF THE PREFERED EMBODIMENTS

Embodiments of the present invention are explained below with reference to accompanying drawings. The technical scope of the present invention, however, is not limited to these embodiments, and includes the subject matter set forth in the claims as well as equivalents thereof.

Figure 1:
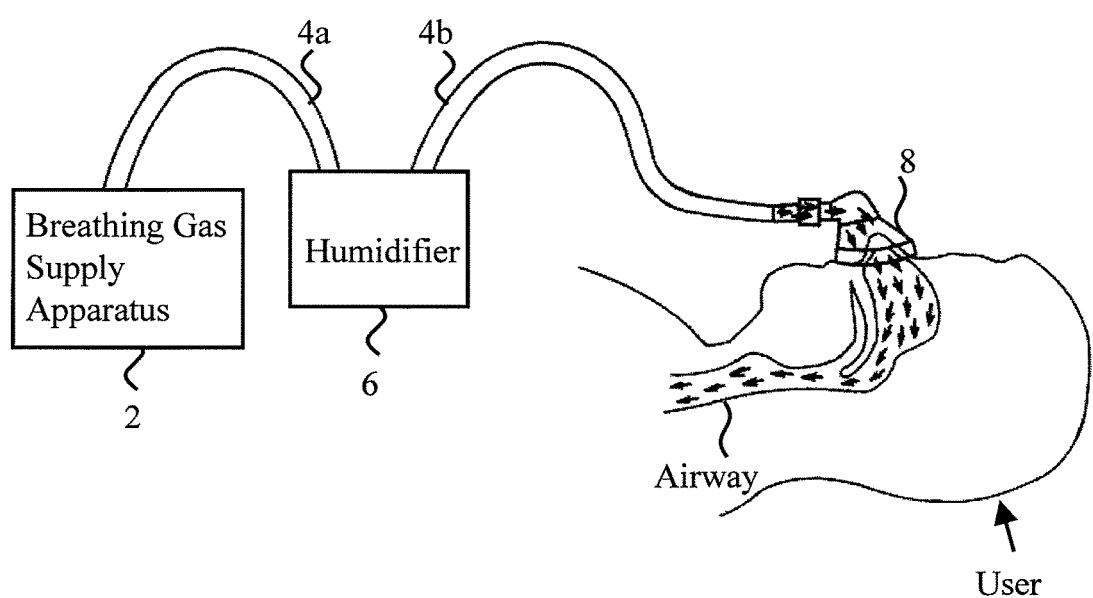
FIG. 1 is a drawing for explaining the overall configuration of CPAP system to which the breathing mask and the wearing tool for it related to the present invention are applied.

FIG. 1 is a drawing for explaining the overall configuration of CPAP system to which the breathing mask and the wearing tool for it related to the present invention are applied.

This CPAP system, through pressurizing gas for breathing according to the prescribed-pressure by a medical doctor and sending the gas for breathing to the airway of a sleep apnea syndrome patient (the user) who is receiving CPAP treatment, expands the user's airway so as to assist the user to breathe.

The CPAP system comprises a breathing gas supply apparatus 2 which supplies gas for breathing by pressurizing the air according to an inputted pressure prescribed by a medical doctor, flexible hoses 4a and 4b which carry gas for breathing, and a breathing mask 8 which is worn by the user when sleeping. Here, a humidifier 6 is also shown, which humidifies gas for breathing to a preliminarily set degree of humidity and supplies it to the breathing mask 8.

Breathing gas supply apparatus 2 starts its operation when powered on, and sends pressurized gas for breathing firstly to humidifier 6 through the flexible hose 4a. Gas for breathing humidified by the humidifier 6 is sent to the breathing mask 8 through the flexible hose 4b. The breathing mask 8 is fixed in close contact with the environs of the nostrils and covering it by a wearing tool as described later, and sends gas for breathing through the nostrils into the airway of the user.

The breathing gas supply apparatus 2, for example, operates in fixed-pressure mode in which the air is pressurized to a certain pressure in the range from 392 Pa to 1961 Pa, or in dynamic-pressure mode in which the pressure of gas for breathing is adjusted according to breathing conditions of the user sensed by a pressure sensor or a flow sensor installed in the apparatus. Humidifier 6 is used to prevent excessive drying of the mucous membranes within the nostrils or the larynx, however, it can be omitted according to the instruction of the medical doctor or preference of the user.

Hereinafter, embodiments of the wearing tool for the breathing mask and of the breathing mask are explained. Embodiments described hereinafter can be practiced solely or in combination, or in another combination.

[1] First Embodiment of Wearing Tool

Figures 2A, 2B:
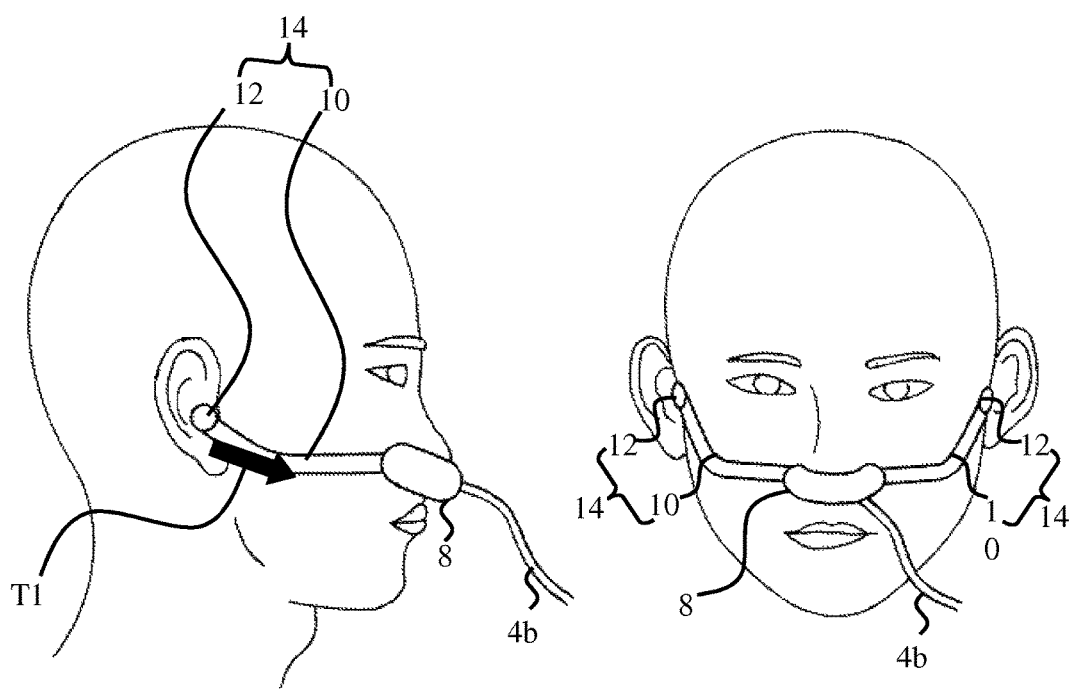
FIGS. 2A and 2B are drawings for explaining a using status of a wearing tool in the first embodiment.

FIGS. 2A and 2B are drawings for explaining a using status of a wearing tool in the first embodiment. Here, a front view and a side view are shown when the user wears the breathing mask 8 by a wearing tool 14. The wearing tools 14 are connected to the both sides of the breathing mask 8 which is connected to the flexible hose 4b and covers the nostril. The wearing tool 14 comprises straps 10 as the pair of the longitudinal connecting members each of which is connected by one end portion to either sides of the breathing mask 8, and the plugs 12 as the pair of fixing members each of which is connected to the other end portion of straps 10. In the following explanations, the lateral direction, the anteroposterior direction, and the vertical direction refer to each of the corresponding directions from the user who wears the wearing tool and the breathing mask.

Figure 3:
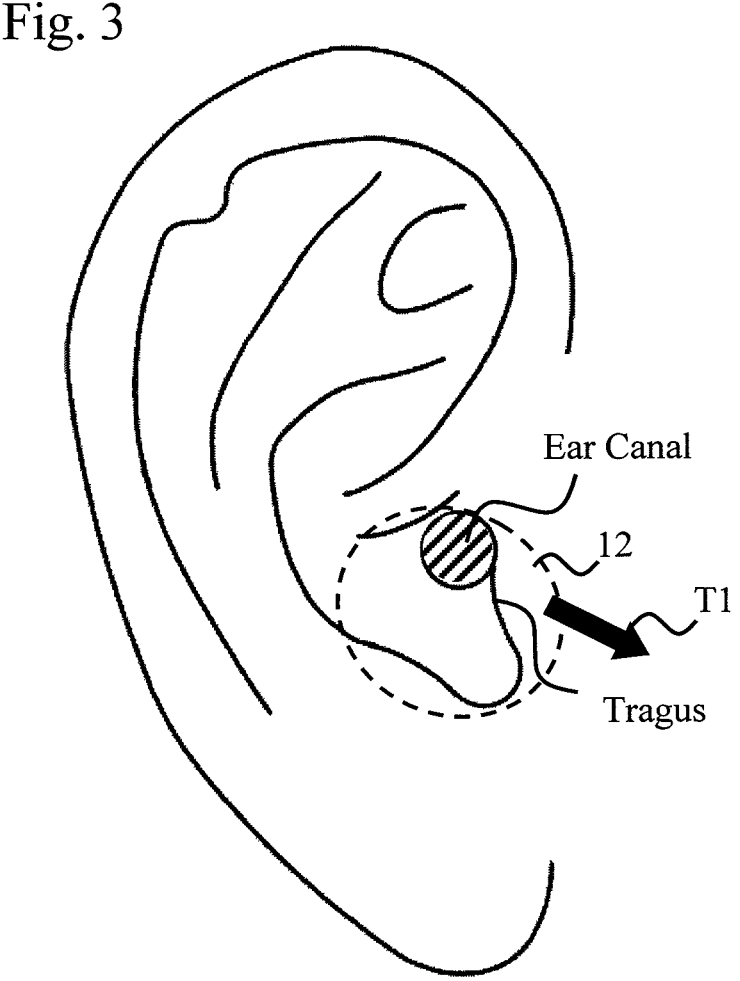
FIG. 3 is a drawing for explaining a using status of the plug 12 plugged in a dimple inside the tragus.

Here, names of parts of the ear together with a using status of the plug 12 are shown in FIG. 3. The plug 12 is plugged into a dimple around the tragus of the user as shown by a dotted line.

Here, by configuring the strap 10 to be in properly adjusted length, a tensional force (arrow T1) acts in the longitudinal direction of the strap 10 when the user wears the breathing mask 8. Then, resisting such a tensional force, the plug 12 latches at inside the tragus. In this way, the wearing tool 14 fixes the breathing mask 8 in close contact with the environs of the nostrils of the user.

The wearing tool 14 which is configured as above does not restrain and compress the head of the user, as with a headgear-style wearing tool. Therefore, an advantageous result is achieved, such that a physical pain and a discomfort feeling such as a feeling of restraint or a feeling of pressure are reduced. Also region of contact with the head of the user has smaller area than that of the headgear-style wearing tool, and thus a discomfort feeling caused by sweat and humidity in the contact region with the wearing tool is reduced. Inconvenience by untidy hair also can be prevented.

The wearing tool 14 is not brought into contact with a pillow when user lies on the back, therefore, displacement of the breathing mask 8, caused by shift of relative position of the wearing tool to the user's head due to a friction with the pillow when user rolls over, can be prevented. If the breathing mask 8 is displaced, close contact with the environs of the user's nostrils is lost, and gas for breathing leaks from gaps which occur between the breathing mask 8 and user's face. This causes problems such as not only poor therapeutic performance by failure in supplying gas for breathing of preliminary designated amount, but also unnecessary and harmful awakening of the user caused by gas for breathing blown onto the user's face. This embodiment, however, can avoid such problems.

The wearing tool 14 in this embodiment also can reduce a pain given to the user, compared with the cold mask-style wearing tool which has loop-shape elastic members such as elastic bands or the like to latch around user's ear. The reason is that the cold mask-style wearing tool gives a pain to the user by biting into the environs of the ear which are pain sensitive and delicate region, but the inside of the tragus is more robustly structured and has lower pain threshold compared to the environs of the ear. Thus, the wearing tool 14 of this embodiment can reduce user's pain.

Further, in this embodiment, such an action of latching the wearing tool around the back of the head as is required in the case of headgear-style wearing tool is unnecessary, therefore, even a user who has impairment in the shoulder with limited moving range can easily wear the breathing mask 8.

FIG. 4 is a drawing for explaining the configuration of the wearing tool 14. FIG. 4A shows the entire configuration of, for example, right-side wearing tool 14. The strap 10, in one example, consists of inelastic fabric. As explained above, one end portion of the strap 10 is connected to a side of the breathing mask 8, and the other end portion is connected to the plug 12. Here, the strap 10 can be fixed to the side of the breathing mask 8 by a connecting means such as stitching, resin adhesion, or the like. In one preferable embodiment, as shown in FIG. 4A, the strap 10 and the breathing mask 8 are configured so that attachment and removal are enabled by the mating portion 10a such as a buckle and a hook which can mate with each other and provided on the end portion of the strap 10 and the side of the breathing mask 8. Thereby, the strap 10 and the breathing mask 8 can be disassembled and cleaned, so that the strap 10 and the breathing mask 8 can be maintained in sanitary manner.

Figure 4A:
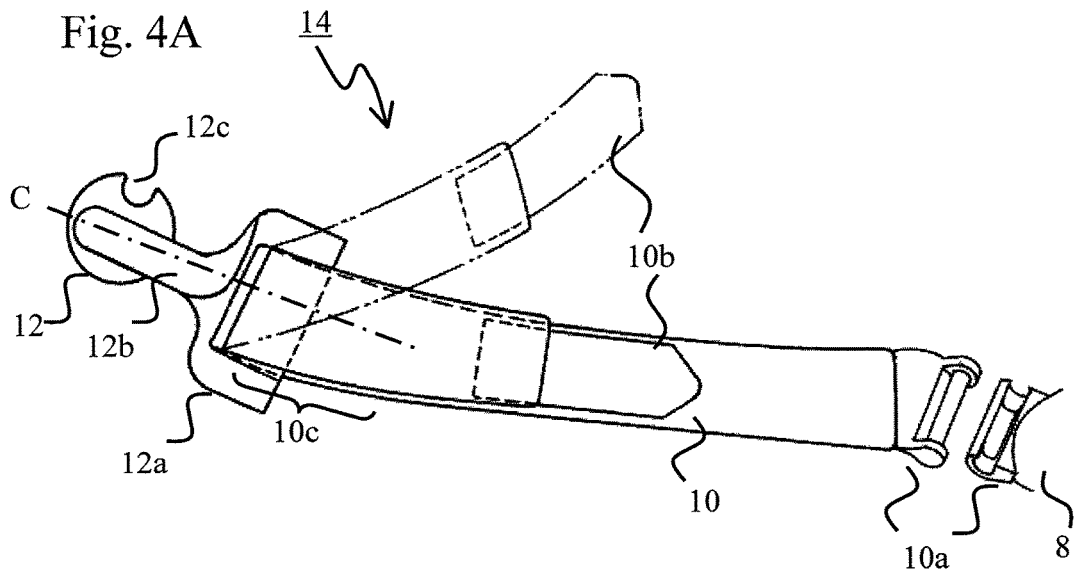
FIG. 4A through FIG. 4D are drawings for explaining the configuration of the wearing tool 14.

On the other hand, as an example of a connecting means of the strap 10 and the plug 12, stitching, resin adhesion or the like can be used. In one preferable embodiment, as shown in FIG. 4A, planate fastener 10b such as Velcro® or Magic tape® are provided on the tip end of the strap 10, which goes through an opening of the buckle 12a and folds back so that the planate fastener 10b latches on the surface of the strap 10. Thereby, the overall length of the strap 10 can be adjustable. Alternatively, various fastening means can be used other than the planate fastener 10b. For example, a configuration is possible, in which equally spaced holes are provided at either of the tip end of the strap 10 or opposing middle portion of the strap 10, and a hook or a button to be snapped in one of the holes is also provided on the other. Or, a tine can be provided on the side of the buckle 12 to latch on the fabric of the surface of the strap 10.

In a further preferable embodiment, one portion of the strap 10 such as a portion 10c which goes through the buckle 12a and folds back can be configured by other material such as elastic strap or the like. Thereby, excessive elasticity overall can be avoided, and at the same time, adjustability of the length of the strap 10 is enhanced.

In this way, the length of the strap 10 can be adjusted according to the size of the face of the user. And, as shown in FIGS. 2A and 2B and FIG. 3, by latching of the plug 12 at inside the tragus against the tensional force which acts in the longitudinal direction of the strap 10, the breathing mask 8 can be fixed in close contact with the environs of the nostrils of the user.

Below, the plug 12 will be explained. The plug 12 which is plugged in the dimple inside the tragus is connected to the buckle 12a by a connecting portion 12b which is exposed on the outside of the tragus. Preferably, the plug 12 and the connecting portion 12b are placed substantially on the centerline C of the strap 10 shown by a dashed-dotted line. Thus, the force to hook of the plug of 12 on the tragus can resist, without being dispersed, the tensional force acting in the longitudinal direction of the strap 10. By this means, dropping off of the plug 12 can be prevented.

Figure 4B:
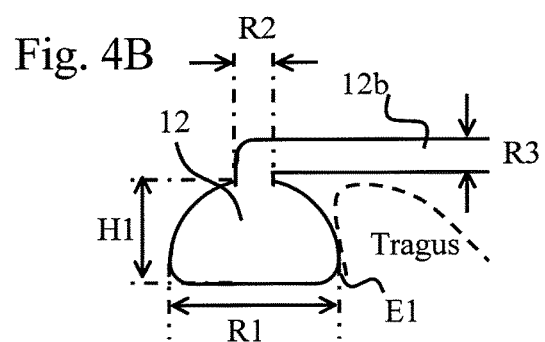
Figure 4C:
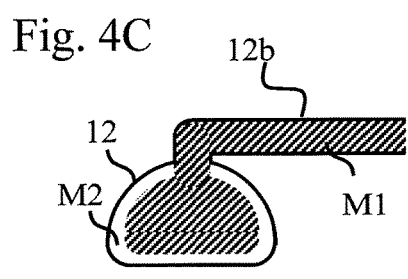
Figure 4D:
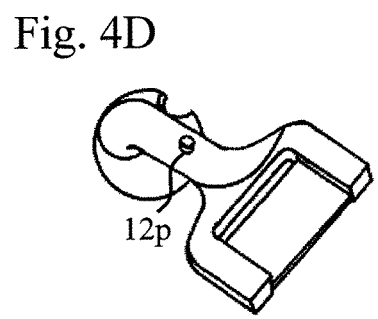

A cross-sectional view of the plug 12 on a dashed-dotted line C is shown in FIG. 4B. The plug 12 which is plugged in the dimple inside the tragus has substantially semispherical shape. Further, it is preferable that an edge E1 which demarks the bottom plane and the lateral side is rounded so as to soften the contact and reduce a pain of the user when the plug 12 is worn.

Also, by making a diameter R1 of the plug 12 greater than the diameter R2 of the portion for connecting the plug 12 and the connecting portion 12b, the area of contact of the plug 12 with the dimple inside the tragus, when the plug 12 is plugged in, can be increased, and thus the force to hook can be enhanced. Also, it is preferable that the height H1 of the plug 12 is such that the plug 12 fits in the dimple inside the tragus, and that the height of a portion of the connecting portion 12b which is exposed out the tragus, that is, the diameter R3 is small. By making the diameter R3 small, even when the user lies on the side and the connecting portion 12b presses the environs of the tragus due to the contact with pillow, a feeling of pressure can be reduced. As for preferable examples of sizes, the diameter R1 lies in the range from 13 to 17 millimeters, the height H1 lies in the range from 5 to 10 millimeters, and the diameter R3 of connecting portion 12b is equal to or less than 8 millimeters. However, this embodiment is not meant to be limited within these ranges of numbers.

The plug 12 can be integrally molded by a single kind of material, or can be formed by using combination of a plurality of materials. In case of integral molding from a single kind of material, a material with moderate elasticity, robustness, and/or biocompatibility is preferably used. Such a material can be, for example, silicone rubber, natural rubber, polystyrene rubber, polyisoprene rubber, polyurethane elastomer, urethane or another pressure relieving material. On the other hand, in case of forming the plug 12 by a plurality of materials, as an example shown in a cross-sectional view in FIG. 4C, the connecting portion 12b and inner portion of the plug 12 shown by hatching can be formed from a material M1 such as nylon or the like, and the outer portion is covered by a material M2 such as urethane or another pressure relieving material, or silicone rubber or the like. Thereby, frictional force when plugged inside the tragus can be enhanced, and dropping off of the plug 12 can be prevented. And at the same time, a contact sensation can be softened and the user's pain can be reduced.

Another preferable embodiment of the plug 12 is explained by referencing FIG. 3 again and by using FIG. 4A. The plug 12 has a cutout as an acoustic hole 12 in the position corresponding to the ear canal, when plugged in the dimple inside the tragus. Thereby, passage for sounds of the outer environment and a beep sound of an alarm clock can be secured. Thus, the user, while sleeping, can hear the sounds of the outer environment in emergency and the beep sound of the alarm clock, therefore, safety of the user is secured and convenience for the user is enhanced. For securing the acoustic passage, the plug 12 can also have a through hole in place of the cutout.

Further, for securing the sanitation of the wearing tool 14, it is preferable to disassemble and clean the wearing tool 14. However, in that case, the user is required by himself to reassemble the wearing tool 14. Therefore, to assist precise and efficient reassemble, the plug 12 is provided with a discriminating means for the left and right sides. For example, as shown in an enlarged view of the plug 12 in FIG. 4D, the plug 12, herewith on the connecting portion 12b provided on the plug 12, has a protrusion 12a. Thereby, discrimination between the left and right sides is possible according to presence or absence of protrusion 12a, or by the number thereof. Alternately, instead of a protrusion, characters, symbols, or figures can be used as the discriminating means for the left and right sides.

[First practical example of fixing member] FIG. 5 is a drawing for explaining the first practical example of the plug 12 as the fixing member. FIG. 5A through FIG. 5D show lateral views of the plug 12. In an example shown by FIG. 5A, the plug 12 further has an inserting portion 12d which is to be inserted in the ear canal. The inserting portion 12d is configured to be substantially circular cylinder shape or circular truncated cone shape (shown by a dashed-dotted line), at least a portion of which has a diameter equal to or greater than that of the ear canal. By providing such inserting portion 12d, in addition to the plug 12 mating with the dimple inside the tragus, a friction force between the exterior surface of the inserting portion 12d and the ear canal prevents dropping off of the plug 12 with higher certainty. Particularly, in case that an external force acts to rotate connecting portion 12b in the direction shown by an arrow T2, in relation to such an external force, the plug 12 is to rotate in the direction shown by an arrow T3. At this time, the plug 12, which has the inserting portion 12d, a frictional force and a stress thereof, can resist such rotation, and dropping off of the plug 12 can be prevented with higher certainty than the case without the inserting portion 12d.

Also in this case, by providing a cutout or a through hole through the entirety of the plug 12 and the inserting portion 12d, the acoustic hole 12c can be secured. Thereby, safety of the user during sleep is secured and convenience for the user is enhanced.

Considering that the ear canal in general has a shallow curve in forward and the upward direction, by making the inserting portion 12d preferably deformable along the shape of the ear canal, the frictional force with the ear canal is secured, and at the same time, a bothered feeling or a feeling of pressure of the user can be prevented. For example, in case that the plug 12 is formed from silicone rubber, the inserting portion 12d can be formed from less rigid material, such as urethane or another pressure relieving material. Or in case of integrally molding the plug 12 and the inserting portion 12d from the same material such as silicone rubber, the inserting portion 12d can be configured less rigid and deformable by having a cavity 12d of a diameter of about 2 millimeters, as shown in FIG. 5C. In this case, configuring the cavity to function as acoustic hole 12c is a preferable embodiment from the standpoints of simplifying the structure and facilitating molding.

Figure 5A:
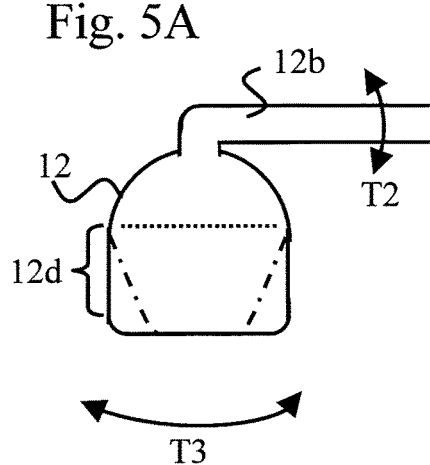
FIG. 5A through FIG. 5D are drawings for explaining the first practical example of the plug 12 as the fixing member.
Figure 5D:
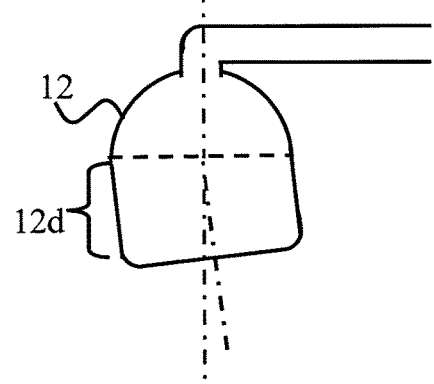
Figure 5B:
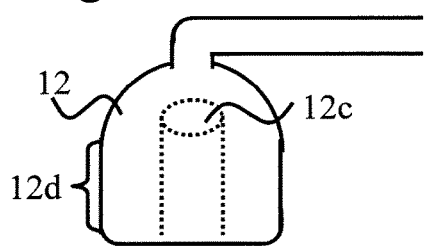
Figure 5C:
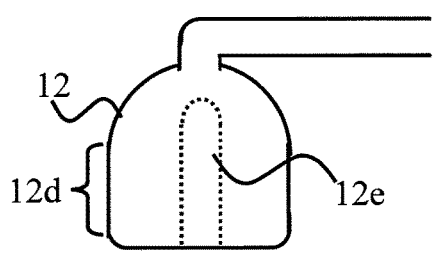

Alternatively, as shown in FIG. 5D, the inserting portion 12d can be configured to have its center which has a certain degree of angle relative to the center CL of the plug 12. Specifically, since the ear canal, in general, has a shallow curve in forward and the upward direction, the inserting portion is provided in such an angle that it is inserted along the ear canal, when worn, to the forward and the upward direction of the user's face.

Thereby, through deformation of the inserting portion 12d along the ear canal, a stress acts to the plug 12, and slight displacement of the position of the plug 12 relative to the tragus can be prevented. That is, positional relation of the plug 12 with the tragus is maintained preferable, and at the same time, the frictional force between the inserting 12d and the ear canal is obtained. Thereby, dropping off of the plug 12 can be prevented more reliably. Together with this, a feeling of pressure of the user can be prevented.

FIG. 6 is a drawing for explaining a variation of the inserting portion 12d. The inserting portion 12d can be configured to have a shaft extending along the direction of insertion which has a plurality of protrusions projected in substantially the perpendicular directions of the direction of insertion.

Figure 6A:
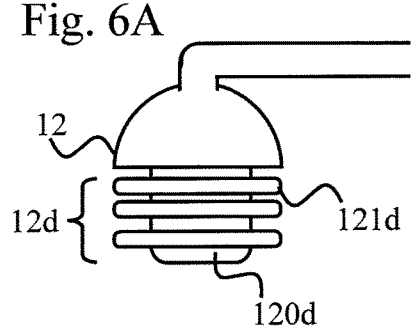
FIG. 6A through FIG. 6G are drawings for explaining a variation of the inserting portion 12d.

For example, as shown in FIG. 6A, a shaft 120d can be provided with plurality of frictional plates 121d of sword guard like flange-shape. Or, as shown in FIG. 6B, the frictional plates 121d can be arranged in spiral so as to shape a root of screw thread around the shaft 120d.

Figure 6F:
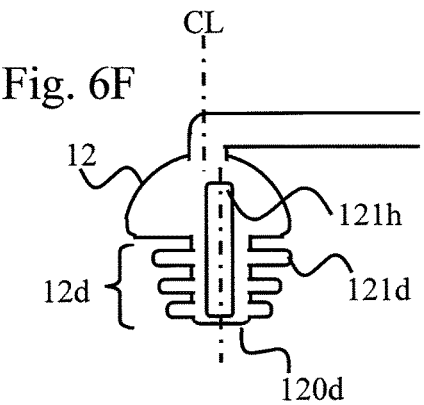
Figure 6B:
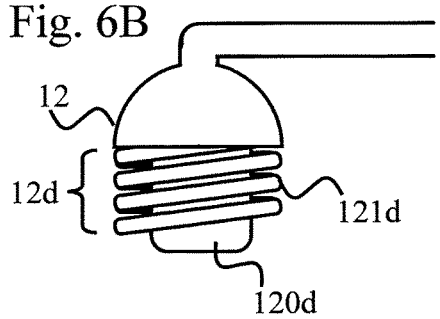
Figure 6G:
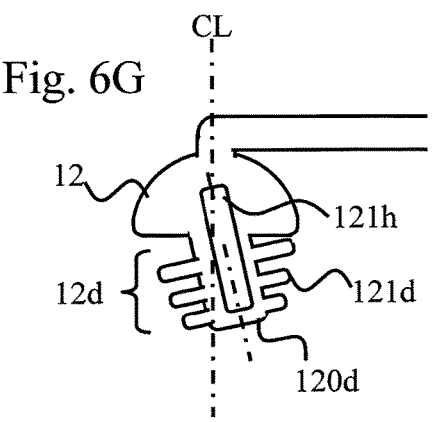
Figure 6C:
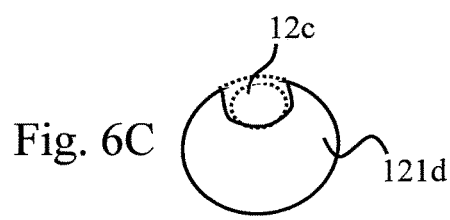
Figure 6D:
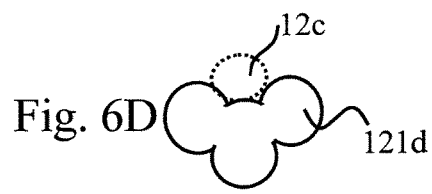
Figure 6E:
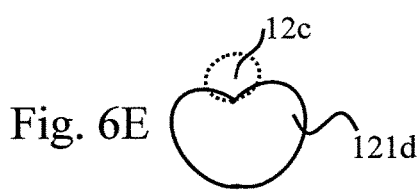

In cases of FIG. 6A and FIG. 6B, the planar shape of the frictional plates 121d can vary such as circular shape as shown in FIG. 6C, cloverleaf shape as shown in FIG. 6D, heart shape as shown in FIG. 6E or the like. Further, each of the frictional plates 121d can have different shapes. In case of circular shape as shown in FIG. 6A, a cutout or a through hole can be provided so as to secure the acoustic hole 12c. Or, in cases of cloverleaf shape as shown in FIG. 6D or case of heart shape as shown in FIG. 6E, without a cutout or a through hole, an opening as acoustic hole 12c can be secured. In cases of FIG. 6A through FIG. 6E, the frictional plates 121d are preferably formed from an elastic material such as silicone rubber. In this configuration, even diameters of the ear canal varies among individuals, the frictional plate can bend to ensure close contact with the ear canal when inserted thereinto. Thereby, the frictional force with the ear canal is enhanced, and dropping off of the plug 12 is prevented reliably. At the same time, a contact sensation with the ear canal can be softened and a feeling of pressure of the user is prevented.

Further, by applying the configuration shown in FIG. 5C to the configurations shown in FIG. 6A through FIG. 6E, the shaft 120d can have a cavity so that the inserting portion 12d can be deformable overall. Or, the shaft 120d can have an angle relative to the center of the plug 12 so as to fit the ear canal. Thereby, the frictional force with the ear canal can be secured, and at the same time, giving a bothered feeling or a feeling of pressure to the user is prevented. In this configuration, the frictional force with the ear canal can be secured, and at the same time, a contact sensation with the ear canal can be softened, therefore, dropping off of the plug 12 can be prevented and also the user's bothered feeling or a feeling of pressure can be reduced.

Alternatively, a configuration in which the center of the plug 12 and the center of shaft 120d are deviated is possible. In FIG. 6F, a cross-sectional view of the center of the plug 12 and shaft 120d in such a configuration is shown. As illustrated, the center of the plug 12 and the center of shaft 120d are deviated, thereby positional relation of the plug 12 with the tragus and positional relation of the inserting portion 12d with the ear canal are maintained preferable.

Further, in this case, the shaft 120d can be formed from an elastic material such as silicone rubber or the like, and formed to have cavity 121h inside, so that the shaft 120d can be deformable along the ear canal. In this case, cavity 121h can be configured to be enclosed space, so that deformation is facilitated and contamination of the inside of the cavity is prevented. Further, as shown in FIG. 6G, the shaft 120d can have an angle relative to the center CL of the plug 12 so as to fit the ear canal.

In this configuration, dropping off of the plug 12 and the inserting portion 12d cab be prevented.

In FIG. 6F and FIG. 6G, the diameter of the frictional plates 121d are configured so as to become smaller as getting closer to the tip end. Since the ear canal, in general, is taper off to the end, such a configuration can secure the frictional force of the inserting portion 12d with the ear canal and soften the contact sensation with the ear canal. By this means, dropping off is avoided and user's bothered feeling or feeling of pressure is reduced.

Figure 7A:
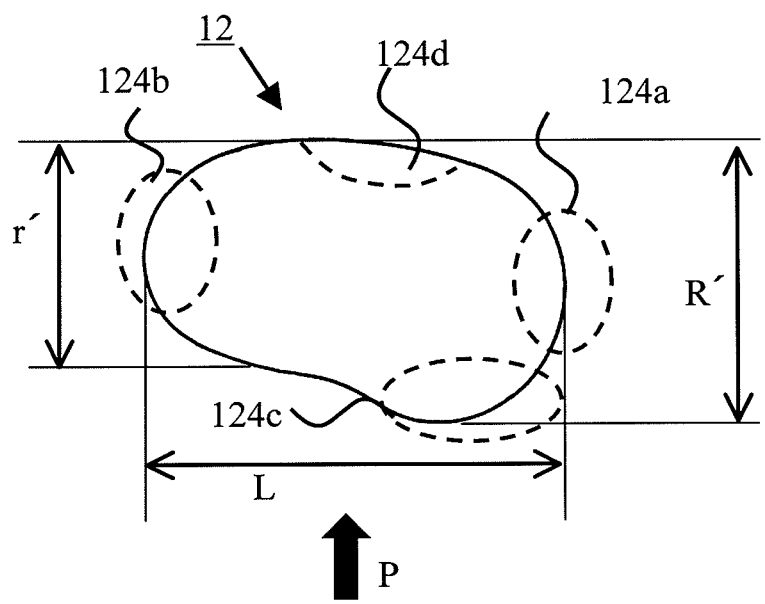
FIG. 7A and FIG. 7B are drawings for explaining the second practical example of the plug 12 as the fixing member.
Figure 7B:
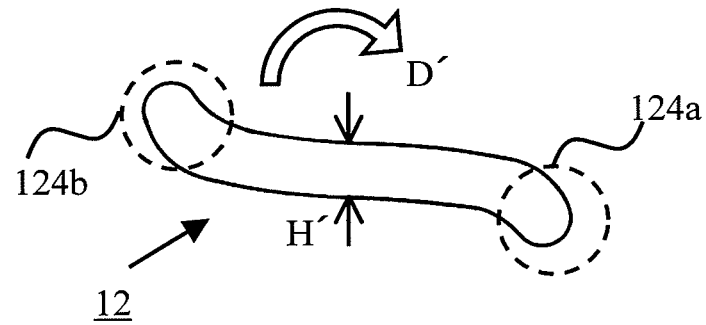
Figure 8:
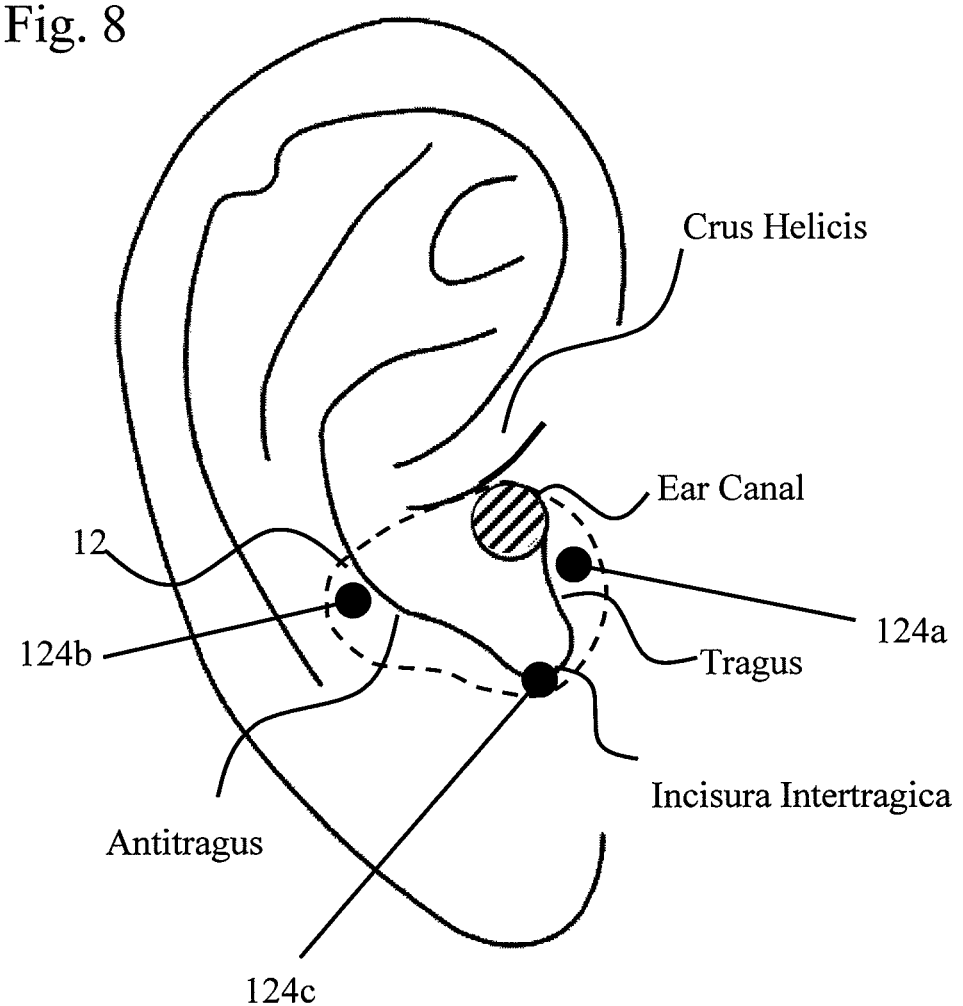
FIG. 8 is a drawing for showing a using status of the second practical example.

[Second practical example of fixing member]FIG. 7 is a drawing for explaining the second practical example of the plug 12 as the fixing member. FIG. 7A shows a plane view of right-side plug 12 as an example, and FIG. 7B shows a lateral view of the plug 12. Here, to facilitate understanding, the connecting portion 12b is not illustrated. FIG. 8 shows using status of the second practical example. FIG. 8 shows, by using a right ear as an example, names of parts of the ear and, by a dotted line, the status of the plug 12 plugged therein.

In FIG. 7 and FIG. 8, the right in the plane of the paper corresponds to the forward direction of the user, that is, the side of the face of the user, the left in the plane of the paper corresponds to the backward direction, that is, the back side of the head of the user, and the perpendicular direction of the plane of the paper corresponds to the lateral direction of the user. In the second practical example, the plug 12 is configured with a plate piece which extends longitudinally in the anteroposterior direction, and has a longitudinal length L which reaches, when worn, the dimple inside antitragus from the dimple inside the tragus. The plug 12 has, for example, asymmetric shape in the anteroposterior direction and/or the vertical directions, that is, preferably a broad bean-shape which has a large-diameter portion of diameter R' and a small-diameter portion of diameter r' connected in the anteroposterior direction.

The plug 12 has a latching portion 124a to latch in the dimple inside the tragus, and adding to this, in a position substantially opposing the latching portion 124a in the longitudinal direction, a latching portion 124b to latch in the dimple inside antitragus. The latching portion 124a has a curved surface which curves in the vertical direction and/or the lateral direction along the shape of the dimple inside the tragus. Likewise, the latching portion 124b has a curved surface which curves in the vertical direction and/or the lateral direction along the shape of the dimple inside antitragus. More preferably, the plug 12 has a latching portion 124c which latches in the dimple inside the incisura intertragica. The latching portion 124c has a curved surface which curves in the vertical direction and/or the lateral direction along the shape of the dimple inside incisura intertragica.

FIG. 7B shows a side view from the direction of arrow P in FIG. 7A. In FIG. 7B, the upward direction in the plane of the paper corresponds to the right side of the user, and the downward direction in the plane of the paper corresponds to the left side of the user, that is, side of the head of the user. In one of preferable embodiments, the plug 12 curves, in its side geometry, so that the latching portion 124a curves towards entrance of the ear canal, and the latching portion 124b curves in the opposite direction. That is, the plug 12 has a shallow S-shape overall.

With regard to the plug 12 described above, a preferable size of the length L in the longitudinal direction is, for example, from 13 to 30 millimeters. A preferable size of the diameter R' of the large-diameter portion is, for example, from 13 to 20 millimeters. On the other hand, a preferable size of the diameter r' of the small-diameter portion is, for example, from 7 to 15 millimeters. Further, a preferable size of the thickness H' of the plug 12 is, for example, from 2 to 10 millimeters. Shapes and sizes described above, however, is an example, and shapes of the large-diameter portion and the small-diameter portion are not limited to precise circular shape. The plug 12 can be, for example, arbitrary shape comprising flat surface or free-form surface. Shapes of the latching portions 124a, 124b, or 124c can be arbitrary shape as long as they can latch namely on the tragus, antitragus, or incisura intertragica.

In the second practical example, in addition to the latching portion 124a latching on the dimple inside the tragus, the latching portion 124b latches on the dimple inside antitragus. Therefore, dropping off of the plug 12 scarcely occurs even when worn by a user who has a small tragus. Particularly, in case that a force acts so as to rotate entirety of the plug 12 to the forward direction as shown in FIG. 7B by an arrow D', by latching of the latching portion 124b on the dimple inside antitragus, dropping off of the plug 12 is prevented. With regard to this, in the above first practical example, the inserting portion 12d prevents the plug 12 from dropping off by latching inside the ear canal, but in this second practical example, same advantageous result can be achieved without the inserting portion 12d. Thereby, even a user who easily feels pain in the ear canal can bear long-term use. Nevertheless, a configuration comprising both of the latching portion 124a of this second practical example and the inserting portion of the above first practical example is obviously possible. By such a configuration, since the latching portion 124b latches on the dimple inside antitragus and the inserting portion 12d latches inside the ear canal, the force to hook is strengthened and dropping off of the plug 12 is prevented more reliably. Further, the plug 12 can latches with greater force to hook, by latching of the latching portion 124c on the dimple inside incisura intertragica.

In the above, a configuration in which each of the latching portion 124a, 124b, and 124c has curved surface to fit the shape of the dimple inside the tragus, the antitragus, and the incisura intertragica respectively, militates for increasing the area of the contact and enhancing the force to hook. Further, by a configuration in which the latching portion 124a curves toward the entrance of the ear canal and the latching portion 124b curves to the opposite direction of latching portion 124a so as to be in close contact with the dimple inside antitragus, contact areas with the dimple inside of the tragus and with the dimple inside of antitragus are further increased and force to hook is strengthened.

Further, as is in the first practical example, the plug 12 can have a cutout or a hole 124d which leads to the ear canal as the acoustic passage. By this means, the user can hear sound of the outer environment. Therefore, safety and convenience for the user are enhanced. Or in another preferable embodiment, the plug 12 has elasticity in the longitudinal direction. Thereby, even in the case that the length between the tragus and antitragus varies among individuals, the plug 12 of the same size can be worn by different users. The plug 12, to obtain elasticity, can be integrally molded from, for example, silicone rubber, natural rubber, polystyrene rubber, polyisoprene rubber, polyurethane elastomer, urethane, or another elastic material, and is connected to the connecting portion 12b which has greater rigidity than the plug 12. By the function of the elastic material as a cushion, an advantageous result is also achieved such that the user's pain is reduced. The plug 12, by having S-shape overall in its side geometry, can more easily bend in the longitudinal direction so as to obtain elasticity.

FIG. 9 is a drawing for showing an variation of the second practical example. FIG. 9A through FIG. 9D show examples of the plug 12 which can easily bend overall in the longitudinal direction so as to obtain elasticity.

Figure 9A:
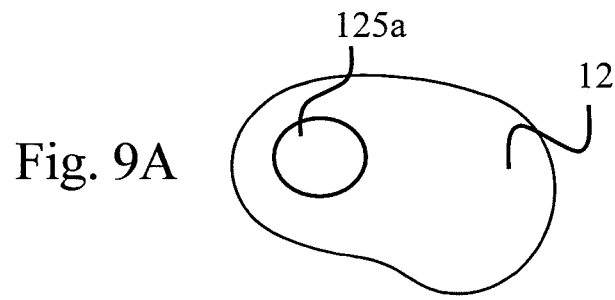
FIG. 9A through FIG. 9D are drawings for explaining a variation of the second practical example.
Figure 9B:
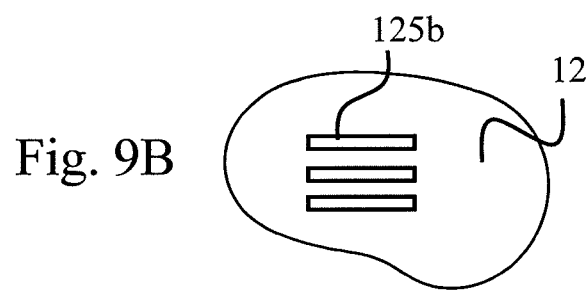
Figure 9C:
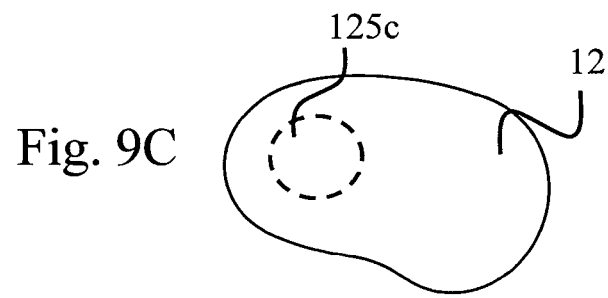
Figure 9D:
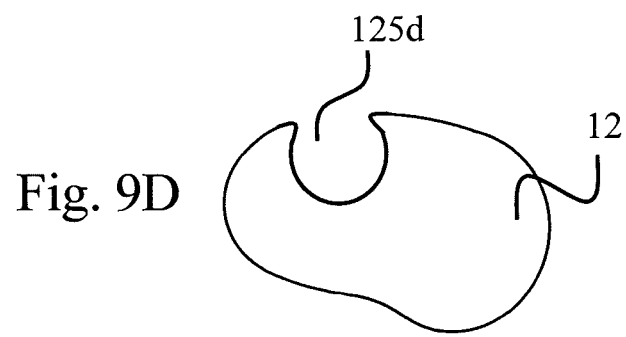

FIG. 9A shows an example of the plug 12 having a hole 125a in the small-diameter portion. FIG. 9B shows an example of the plug 12 having, in the small-diameter portion, the longitudinal slits 125b along the longitudinal direction of the plug 12. FIG. 9C shows an example of the plug 12 having a cavity (hollow space or the dimple) 125c in the small-diameter portion. FIG. 9D shows an example of the plug 12 having a cutout 125d in the small-diameter portion.

In examples of FIG. 9A through FIG. 9D, since rigidity of the small-diameter portion which has the hole 125a, the slits 125b, the cavity 125c, or the cutout 125d is comparatively reduced, the plug 12 becomes easy to bend therein. Hence, the plug 12, by bending overall, obtains elasticity in the longitudinal direction. Here, the hole 125a, the slits 125b, or the cutout 125d provided in the plug 12 can function as the acoustic passage.

Figure 10A:
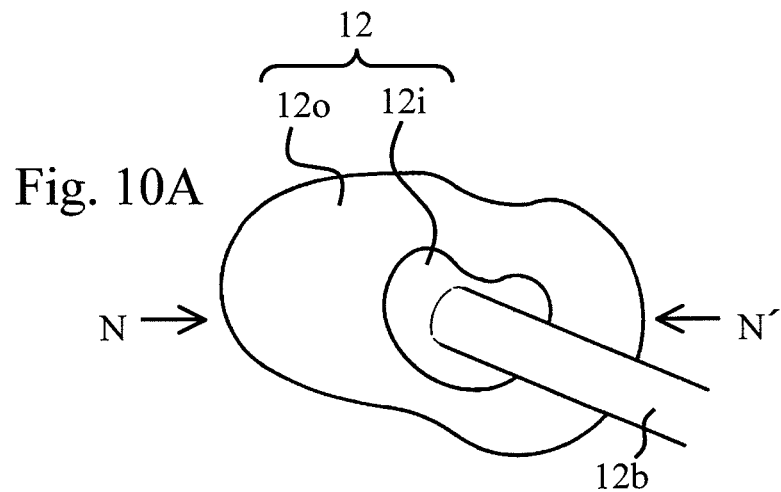
FIG. 10A through FIG. 10C are drawings for explaining a connecting structure of the plug 12 and the connecting portion 12b.
Figure 10B:
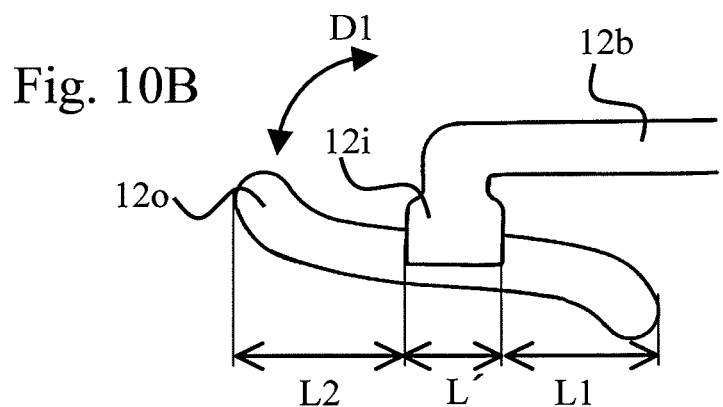

FIG. 10 is a drawing for explaining a connecting structure of the plug 12 and the connecting portion 12b. FIG. 10A shows, for example, a plane view of right-side plug 12 together with a part of the connecting portion 12b. FIG. 10B shows a cross-sectional view along a line NN' in the FIG. 10A. In FIG. 10A and FIG. 10B, the right in the plane of the paper corresponds to the forward direction, and the left in the plane of the paper corresponds to the backward direction.

Here the plug 12 is configured to be divided into an inner structure 12i and an outer structure 12o, and the inner structure 12i and the outer structure 12o are formed from different materials. That is, the inner structure 12i and the connecting portion 12b are integrally molded from a material which has a certain degree of rigidity, such as nylon or the like. On the other hand, the outer structure 12o of the plug 12 is formed from an elastic material such as silicone rubber, urethane or the like. In this configuration, the plug 12 can have a certain degree of rigidity overall and a greater frictional force when plugged in inside the tragus or the antitragus, and thus dropping off of the plug 12 can be prevented. At the same time, contact sensation can be softened, and the user's pain can be reduced.

Here, by shortening the length L' of the inner structure 12i in the longitudinal direction of the plug 12, the length L1 and L2 of the outer structure 12i in the longitudinal direction of the plug 12 can be lengthen. Thereby, elasticity of the plug 12 in the longitudinal direction can be secured.

Here, a preferable size of the length L' of the inner structure 12i in the longitudinal direction of the plug 12 is, for example, from 3 to 15 millimeters. And a preferable size of the length L1 of the outer structure 12o in the longitudinal direction of the plug 12 from inner structure 12i towards the forward direction is, for example, from 0.5 to 26 millimeters. On the other hand, a preferable size of the length L2 of the outer structure 12o in the longitudinal direction of the plug 12 from inner structure 12i towards the backward direction is, for example, from 0.5 to 26 millimeters. Shapes and sizes described here are examples, and various shapes and sizes are possible as long as they satisfy the requirements described above. For example, a length in the vertical direction of the plug 12 such as to reach the crus helicis is also possible, as long as the plug 12 has the latching portions 124a, 124b, and the longitudinal length L.

Further in the second practical example, as shown by an arrow D1, by deformation of the plug 12 in the anteroposterior direction with a joint with the connecting portion 12b as a center, a tilting movement in the anteroposterior direction can be simulated. Direction in which the ear faces varies among individuals, and some users have comparatively forward facing ears while the others have comparatively laterally facing ears. The plug 12, by tilting in the anteroposterior direction, can be adapted to such variation, and can be fixed in the desired position without depending on the direction of the user's ears.

Figure 10C:
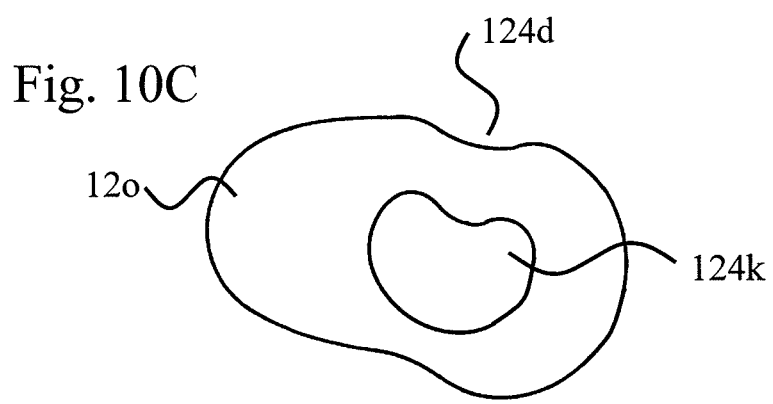

In one of preferable embodiments, the outer structure 12o and the inner structure 12i of the plug 12 are configured to mate with each other to enable attachment and removal. Thereby, the plug 12 can be disassembled and cleaned, so that the sanitation is maintained. In this case, in the combination of the outer structure 12o and inner structure 12i, the mating portions have different mating shape between the both sides. For example, the outer structure 12o of the plug 12 as shown in FIG. 10C has the mating portion 124k of C-shape with an opening upward, which is asymmetric in the anteroposterior direction. Thereby, an attempt of mating the plug 12 with the mating portion 12b of an opposite side results failure, in which incorrect assembly is easily detected, and in which correct assembly can be assisted. Further, on the outer structure 12o of the plug 12, a cutout or a hole 124d can be provided as the acoustic passage along the C-shape of the mating portion 124k. The shape of the mating portion 124k can vary without being limited to the above example. The shapes of the mating portions 124k on the both sides can obviously be totally different.

[Third practical example of fixing member]FIG. 11 is a drawing for explaining the third practical example of the plug 12 as the fixing member. The third embodiment is more preferable for preventing dropping off of the plug 12 with higher certainty. The third practical example can be practiced solely or in combination with either of above described the first, or the second practical examples.

In the configuration shown in FIG. 11A, the wearing tool 14 further comprises a hook-shape ear hooking portion 13 as the latching member to latch around ear. The ear hooking portion 13 is connected to the end portion of the strap 10 to which the plug 12 is connected. Preferably, as shown in FIG. 11A, the ear hooking portion 13 is connected to the connecting portion 12b of the plug 12. By this means, the plug 12 and the ear hooking portion 13 can be integrally molded from the same material, for example, silicone rubber or the like. Alternatively, the plug 12 and the ear hooking portion 13 can be formed from different materials. In that case, it is preferable that the ear hooking portion 13 is formed from such a material as to have certain degree of elasticity and rigidity, so that the hook-shape is secured, as well as the facility of hooking around the ear. Examples of such a material are, nylon, acetyl cellulose, celluloid, or another rein, or titanium, stainless, aluminum, duralumin, or another metal.

By the above configuration of the ear hooking portion 13, dropping off of the plug 12 can be prevented with higher certainty. Further, even if the plug 12 drops off, the ear hooking portion 13 can prevent dropping off of the entirety of the wearing tool 14.

It is preferable to configure, as shown in FIGS. 11B and 11C, a cross-sectional shape of the ear hooking portion 13 along a dotted line AB to be spindle-shape (FIG. 11B) or circular-shape (FIG. 11C) which have curved line on the side which makes contact with the environs ear, for preventing biting of the ear hooking portion 13 into the base of the ear. Thereby, user's pain can be reduced. Especially, in the case of spindle-shape, since thickness of the top portion A of the cross-sectional shape in FIG. 11B is thin, feeling of pressure is reduced even when the user lies on the side with his ear pressed by a pillow.

Further, diameter of the ear hooking portion 13 is not required to be consistent. An example is that, the central portion 13b, which generate the most force to latch when latching around the ear, has the largest diameter, and the tip portion 13a has a smaller diameter. Thereby, twist of the central portion 13b can be avoided so that the hook-shape and thus the facility to latch around the ear are secured, and biting around the ear is also prevented. On the other hand, the tip portion 13a is deformable to some degree along the shape of the environs of the ear, and pressure to the environs of the ear is reduced.

As shown in FIG. 11D, the ear hooking portion can be configured to be rotatable relative to the plug 12 in the direction shown by an arrow T4. For example, the plug 12 and the ear hooking portion 13 can be a combination of separate components combined rotatably, or the plug 12 and the ear hooking portion 13 can be integrally molded by the same material which has some degree of elasticity such as silicone rubber, so that rotation is realized by twisting the entirety. By doing so, the user can wear the wearing tool 14 in such manners that the user first latches the ear hooking portion 13 around the ear, then plug the plug 12 into the dimple inside the tragus by rotating the plug 12. Or, the user can wear the wearing tool 14 in steps such as latching the ear hooking portion 13 around the ear by rotating the ear hooking portion 13, after plugging the plug 12 in the dimple inside the tragus. By this means, the wearing tool 14 can be more easily worn than the case that the plug 12 and the ear hooking portion 13 are not rotatable. The preferable size of diameter of the ear hooking portion 13 shown in FIG. 11A through FIG. 11D, is from 3 to 10 millimeters for reducing biting to the environs of the ear. The embodiment of the presented invention, however, is not limited to this range.

Alternatively, the ear hooking portion 13 can be loop-shape as shown in FIG. 11E. In this case, the ear hooking portion 13 is formed from an stretch material so as to enable latching around the ear. This shape is that of so called cold mask-style, however, since the ear hooking portion 13 of this type is used as a secondary latching means in this embodiment, the user's pain is less than the case of the ear hooking portion 13 is solely used. By this means, the ear hooking portion 13 can prevent dropping off of the plug 12 with higher certainty.

Figure 12A:
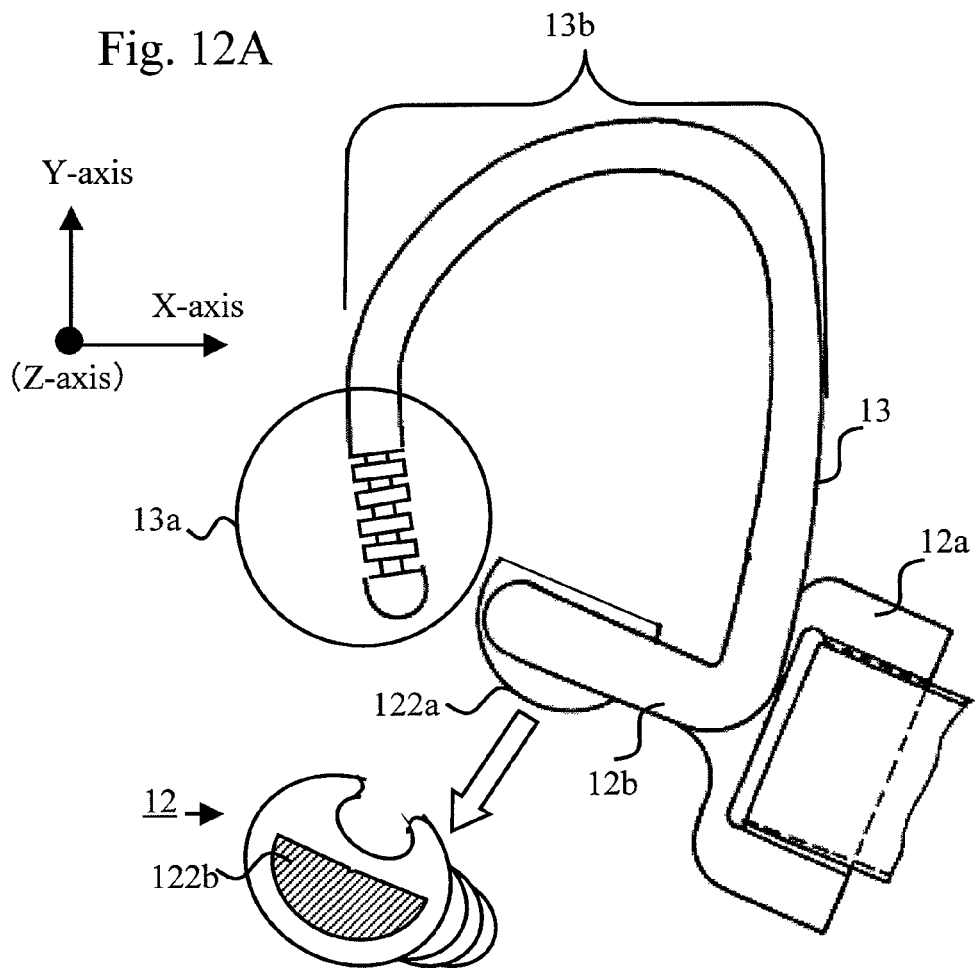
FIG. 12A through FIG. 12C are drawings for explaining a variation of the plug 12 and the ear hooking portion 13.

FIG. 12 is a drawing for explaining a variation of the plug 12 and the ear hooking portion 13. In this variation, as shown in FIG. 12A, the plug 12 and the ear hooking portion 13 are formed from different materials so that attachment and removal thereof are enabled. For example, the plug 12 is formed from a material which has some degree of elasticity, durability, and biocompatibility, such as silicone with hardness of 40 degrees. On the other hand, the ear hooking portion 13 is integrally molded together with the connecting portion 12b and the buckle 12a by a material which has some degree of elasticity and rigidity such as nylon. And the plug 12 and the ear hooking portion 13 are attached each other by the mating portion 122a of the ear hooking portion 13 which mates in a hole 122b provided on the plug 12.

Here, exterior appearances of variations of the plug 12 are shown in FIG. 6F and FIG. 6G. In this case, cavity 121h shown in FIG. 6F or in FIG. 6G can be connected or can be disconnected to the hole 122b. In the configuration in which the cavity 121h is connected to the hole 122b, molding is facilitated.

In this way, the plug 12 and the ear hooking portion 13 are configured to enable attachment and removal, they can be easily disassembled and cleaned, or worn components can be easily replaced. Hence, convenience for the user is enhanced.

Figure 12B:
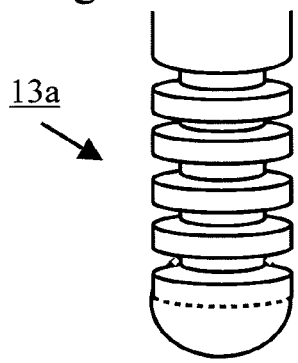

In this variation, a tip portion 13a of the ear hooking portion 13 is, as shown in an enlarged view in FIG. 12B, shaped as skewered multiple discs, so that the diameter is intermittently changes. Thereby, when the ear hooking portion 13 is integrally molded from the same material, rigidity of the tip portion 13a can be comparatively reduced. By this means, the region around the central portion 13b of the ear hooking portion 13 can resist twist so as to maintain the hook-shape, and to facilitate latching around ear. And at the same time, biting into the environs of the ear is prevented. On the other hand, the tip portion 13a can be deformed to some degree along the shape of the environs of the ear, so that pressure to the environs of the ear is reduced.

Figure 12C:
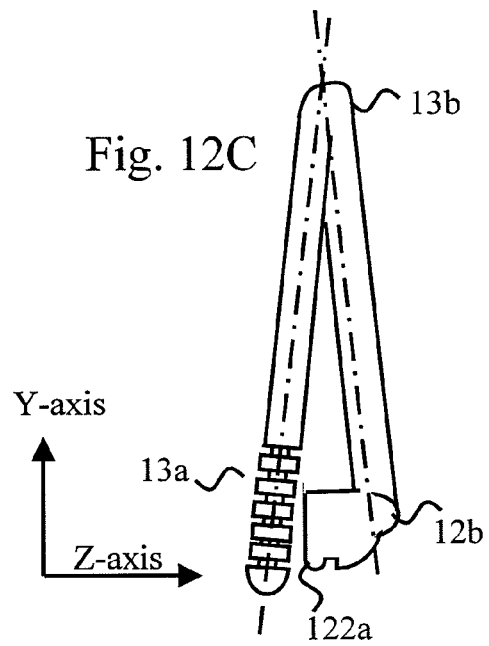

Further, an exterior appearance of the ear hooking portion in Y-Z axis is shown in FIG. 12C with the lateral direction of FIG. 12A as X-axis, the vertical direction of FIG. 12A as Y-axis, and the perpendicular direction to the plane of the paper as Z-axis. The ear hooking portion 13 can be formed to have sterically-skewed shape, so that the portion from the central portion 13b to the connecting portion 12b and the tip portion 13a have different angles in Y-Z plane. Thereby, the ear hooking portion 13 can better fit the shape of curved surface of the environs of the ear, when worn by the user. Hence, the ear hooking portion 13 can be fixed reliably around the ear, and a contact sensation of the user is softened so that the user's pain can be prevented.

[2] Second Embodiment of Wearing Tool

Figure 13:
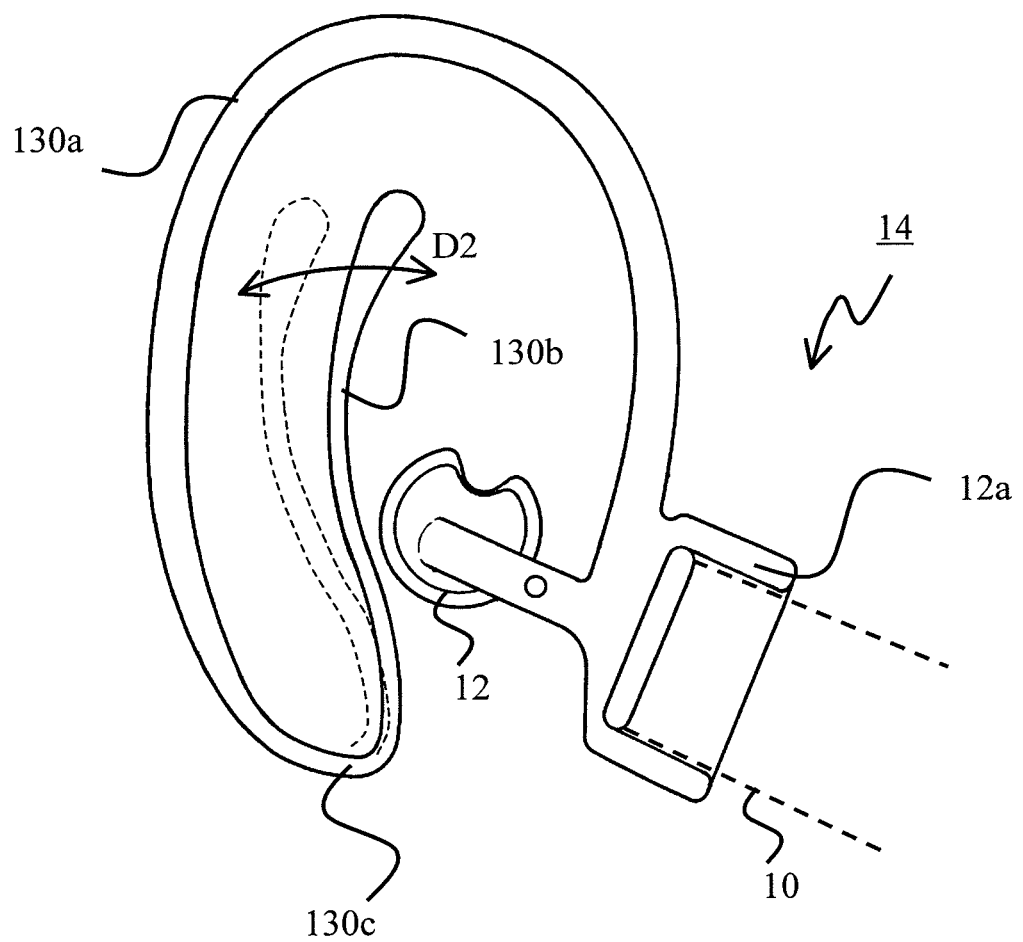
FIG. 13 is a drawing for explaining the second embodiment of the wearing tool 14.

FIG. 13 is a drawing for explaining the second embodiment of the wearing tool 14. The wearing tool 14, which is provided on an end portion of the strap 10 opposite to the other end portion which is connected to the breathing mask 8, latches at the position of the ear of the user. FIG. 13 shows the wearing tool for the right ear as an example, with the right in the plane of the paper corresponding to the forward direction, and the left in the plane of the paper corresponding to the backward direction.

As illustrated, the wearing tool 14 has a frame portion 130a which has an upside-down U-shape curve. The frame portion 130a has on one end portion the buckle 12a to be connected to the strap 10, and has on the other end portion a biasing portion 130b. The biasing portion 130b is provided inside the frame portion 130a. The frame portion 130a and the biasing portion 130b are integrally molded so that they shape a hairpin curve overall, binding together at curving portion 130c. For example, the frame portion 130a and the biasing portion 130b are, as with the above ear hooking portion 13, formed from an material which has certain degree of elasticity and rigidity such as, nylon, acetyl cellulose, celluloid, or another rein, or such as titanium, stainless, aluminum, duralumin, or another metal.

The biasing portion 130b has a length half to three fourth of the vertical length of the frame portion 130a. Together with this, the biasing portion 130b has a slightly curved shape along the shape of the base of ear, and the tip end of the biasing portion 130b is apart from the frame portion 130a. The frame portion 130a and the biasing portion 130b are formed so that they have substantially circular cross-sectional shape. The curving portion 130c is configured to have a comparatively small diameter compared with the diameters of the frame portion 130a and the biasing portion 130b, and thus to have comparatively low rigidity. In this configuration, the biasing portion 130b tilts in the antero-posterior direction as shown by an arrow D2 with the curving portion 130c as a pivot.

Here, a case is shown in which the second embodiment is practiced together with the plug 12 of the first embodiment, however, the second embodiment can be solely practiced. And the breathing mask in practicing the second embodiment can be a breathing mask which covers only the environs of the nostril, or a breathing mask which covers the nostrils and the mouth.

Figure 14:
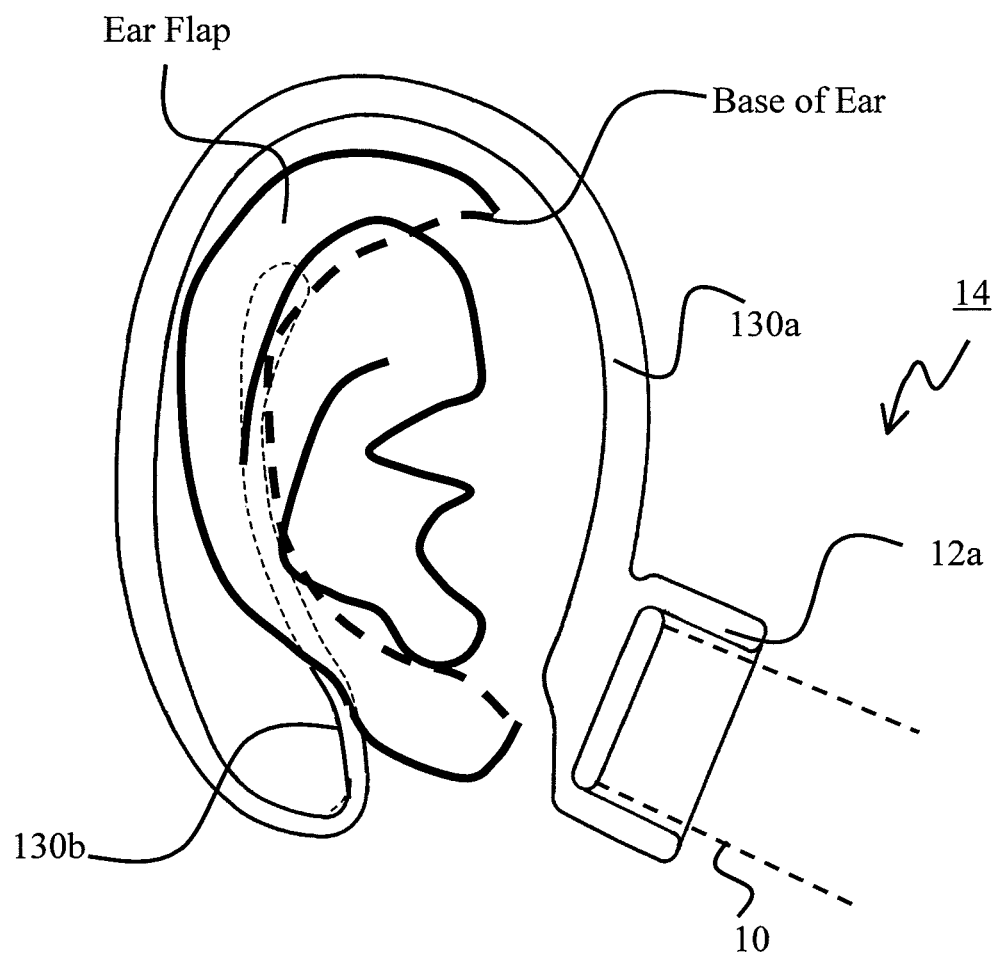
FIG. 14 is a drawing for explaining a using status of the wearing tool 14.

FIG. 14 is a drawing for explaining a using status of the wearing tool 14. In FIG. 14, to facilitate understanding, the plug 12 is not illustrated. FIG. 14 shows right ear as an example, and the right in the plane of the paper corresponds to the forward direction, and the left in the plane of the paper corresponds to the backward direction. The frame portion 130a is placed to surround and circumvent the environs of the ear flap. The biasing portion 130b, within the frame portion 130a, abuts the base of the ear from behind the ear, and biases in the forward direction. For reliably securing the wearing tool 14, the frame portion 130a and the biasing portion 130b can be curved shape in the lateral direction of the user, or in the other word, in the perpendicular direction in the plane of the paper in FIG. 14, so as to fit the shape of the environs of the ear at temporal area of the user.

In the second embodiment, since the frame portion 130a surrounds and circumvents the environs of the ear flap, placing of the burden topically on the base of the ear due to the tension of the strap 10 connected to the buckle 12a can be prevented. Therefore, the occurrence of a pain, as with cold mask-style wearing tool, caused by elastic bands or the like placing burden topically on the base of the ear is prevented. Especially, the occurrence of a pain due to biting of the elastic band on the top portion of the base of ear can be prevented. Also, even when the user lies on the side, the occurrence of pain caused by the frame portion 130a being pressed between the ear and the head, and thus biting the back of the ear and the head portion can be prevented.

By the biasing portion 130b biasing allover the base of the ear, the breathing mask can be fixed reliably. Also, although the shape and the size of the ear vary among individuals, gaps between the biasing portion 130b and the base of ear barely occur, and thus force to hook is enhanced. Therefore, increase of a pain due to displacement of wearing tool and thus scraping therein can be prevented. Thereby, pain and a discomfort feeling caused by wearing the breathing mask can be reduced.

Figure 15A:
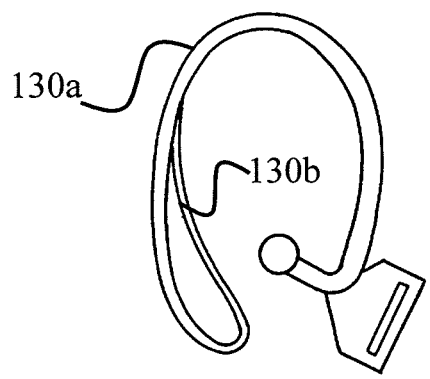
FIG. 15A through FIG. 15C are drawings for explaining examples of the shape of the biasing portion 130b.
Figure 15B:
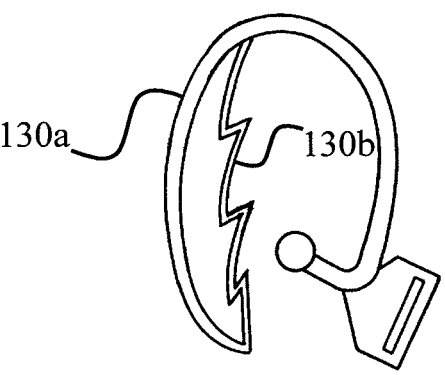
Figure 15C:
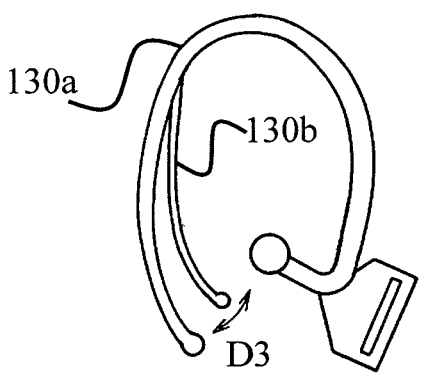

FIG. 15 is a drawing for explaining examples of the shape of the biasing portion 130b. FIG. 15A shows an example in which the biasing portion 130b has its tip end connected to the frame portion 130a and shapes a loop. Preferably, the diameter of the biasing portion 130b is configured to be smaller than the diameter of the frame portion 130a. In this configuration, a loop shaped by the biasing portion 130b bows and performs biasing. FIG. 15B shows an example in which the biasing portion 130b has its tip end connected to the frame portion 130a and shapes accordion, and by bowing thereof biasing is performed. FIG. 15C shows an example in which the biasing portion 130b and the frame portion 130a bind together at the central portion, not at the tip end of the frame portion 130a, and the tip end of the biasing portion 13b is apart from the frame portion 13a, so that the overall shape is branched-shape. Preferably, the diameter of the biasing portion 130b is configured to be smaller than the diameter of the frame portion 130a. By this means, the biasing portion 130b is enabled easily to tilt in the direction shown by an arrow D3, and the biasing portion 130b performs biasing through titling. The second embodiment includes configurations in which the biasing portion 130b is realized by pressure relieving material as sponge or the like, alpha gel, or metal spring or the like, which is provided on the frame portion 130a.

FIG. 16 is a drawing for explaining a variation of the second embodiment. FIG. 16A shows an example of the wearing tool 14 of which the buckle 12a has plurality of the strap holes 12s. By this means, the length of the straps 10 can be adjusted in a stepwise fashion, and wearing can be done more flexibly. FIG. 16B shows an example of the strap holes 12s arranged in different angles in a fan-like fashion. By this means, angles of the straps 10 relative to the frame portion 130a can be adjusted. Therefore, individual difference of the user in positional relationship between the nostrils and the ear can be addressed.

Figure 16A:
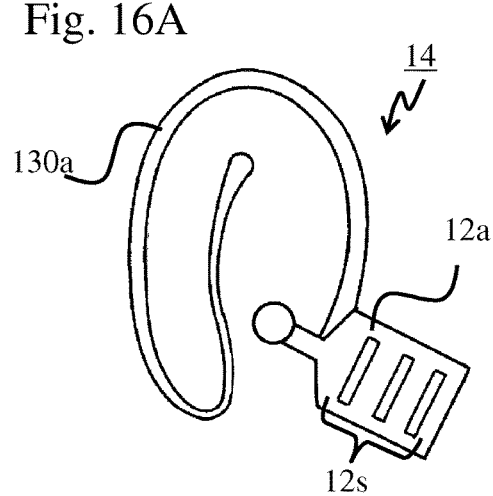
FIG. 16A through FIG. 16F are drawings for explaining a variation of the second embodiment.
Figure 16B:
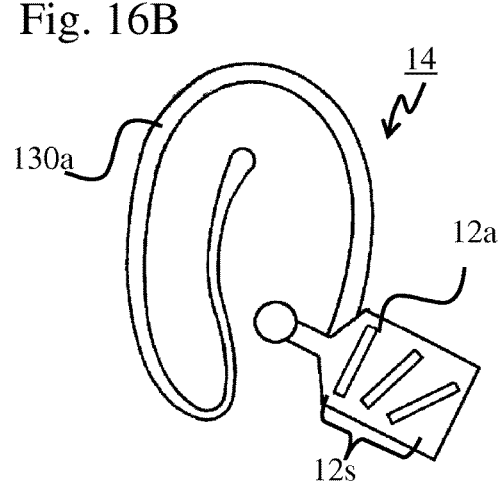
Figure 16C:
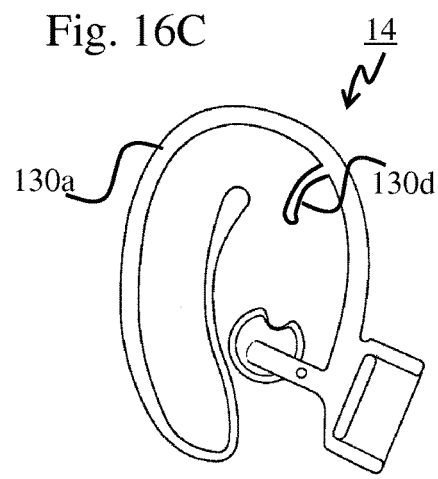
Figure 16D:
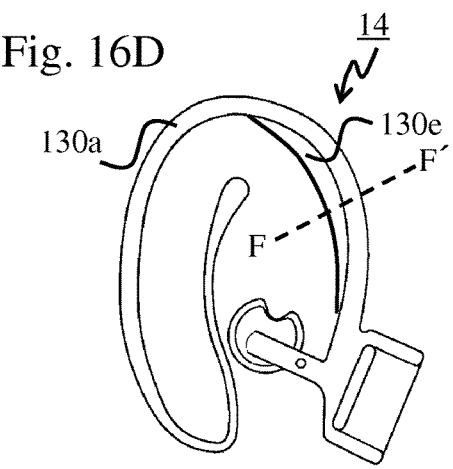
Figure 16E:
Figure 16F:

FIG. 16C shows an example of the wearing tool 14 which has on the frame portion 130a latching portion 130d to latch on the crus helicis (see FIG. 8). By this means, the force to latch is enhanced. FIG. 16D shows an example of the wearing tool 14 which has a rib 130e inside of U-shape shaped by the frame portion 130a. A cross-sectional shape on a dotted line FF' is illustrated in lower section. Thus, by making the diameter small, the frame portion 130a can be formed smaller and lighter with, and at the same time, rigidity of the frame portion 130a is secured as shown in FIG. 16E. Alternatively, in place of providing the rib 130e, the frame portion 130a can be configured to have a cross-sectional shape of spindle-shape tucking in the inward direction F as shown in FIG. 16F. Here, by configuring the rib 130e or an edge of spindle-shape to have the shape and the sizes so as to surround and to circumvent the environs of the ear flap, scraping of rib 130e against the top of the base of ear and thus causing pain are prevented.

In case of practicing the second embodiment together with the plug 12 of the first embodiment, by biasing of the biasing portion 130*b*, the pressures placed on the tragus or the antitragus can be distributed. And thus a pain or a discomfort feeling of the user caused by wearing the breathing mask can be reduced.

[3] Third Embodiment of Wearing Tool

In the third embodiment, the wearing tool 14 has supporting member provided along the longitudinal direction of the wearing tool 14.

Figure 17A:
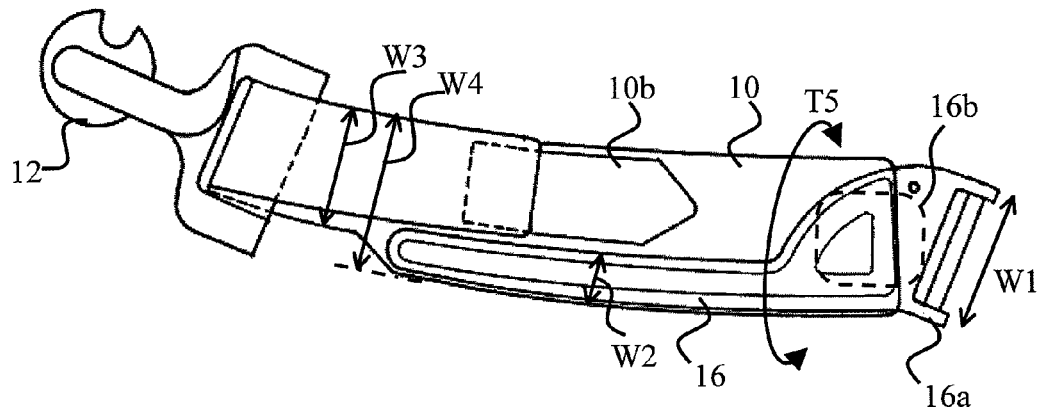
FIG. 17A through FIG. 17C are drawings for explaining configuration of the supporting member.

FIG. 17 is a drawing for explaining configuration of the supporting member. FIG. 17A shows, by using the right-side strap 10 of the first embodiment as an example, the supporting member provided on the strap 10. However, the third embodiment can be practiced solely, or together with any of the wearing tools of the first, the second, or another embodiments. And the breathing mask in practicing the third embodiment can be a breathing mask which covers only the environs of nostrils, or a breathing mask which covers the nostrils and the mouth of the user.

As shown in FIG. 17A, the strap 10 is provided with, as the supporting member, a panel 16 which extends in the longitudinal direction of the strap 10 and has a certain length in the width direction, and has greater rigidity than the strap 10. The panel 16 is preferably formed from a material which has robustness, adding to rigidity, such as nylon, polyacetal, polypropylene or the like. And the strap 10 and the panel 16 are fixed each other at least at the rim portion of the panel 16 by stitching or by resin adhesion or the like. And the mating portion 16*a* which can mate with the side portion of the breathing mask 8 is provided at the end portion of the panel 16. By this means, the strap 10 is connected to the breathing mask 8 by the panel 16.

The panel 16 has a certain length in the longitudinal direction and in the width direction of the strap 10, and has certain degree of rigidity, therefore the following advantageous results are achieved. Firstly, even when pressurized gas for breathing is supplied to the inside of the breathing mask 8 and a tensional force acts on the longitudinal direction of the strap 10, a stress in the longitudinal direction can prevent extension of the strap 10, and thus the breathing mask 8 can be in close contact with the environs of the nostrils of the user. Secondly, even when an external force acts to twist the breathing mask 8 in the width direction of the strap 10, as shown by an arrow T5, a stress in the width direction prevents twist of the strap 10 and thus displacement of the breathing mask 8.

Here, more preferably, the panel 16 has, in the region of the end portion which is connected to the side portion of the breathing mask 8, a plane portion 16*b* which has a width in the width direction and a length the longitudinal direction. For example, for the panel 16 which has a length from 3 to 15 centimeters in the longitudinal direction and width from 2 to 5 centimeters in the width direction, plane portion 16*b* is configured to have a plane region which has a length more than 1 centimeters in the longitudinal direction and a width more than 2 centimeters in the width direction. By this means, a stress against twist in the width direction can be enhanced, hence twist is prevented with higher certainty. However, the sizes of plane portion 16*b* are not limited to the above figure range.

In further preferable embodiment, the panel 16 has a width, in a portion of the longitudinal direction, which is narrower than the width of the end portion which is connected to the breathing mask 8. Specifically, as shown in FIG. 17A, the panel 16 has a with W1 at the end portion which is connected to the breathing mask 8, and has a width W2 which is narrower than the width W1 in a portion which lies from the center portion to a portion closer to the plug 12 in the longitudinal direction. In other words, the panel 16 has, so to say, a hollowed shape in the upper region.

The panel 16 is required to have a certain degree of rigidity so as to fix the breathing mask 8 at the environs of the nostrils of the user and to prevent its displacement. However, since the strap 10 passes on the cheekbones of the user when worn, as illustrated in FIGS. 2A and 2B, there is the concern that, if the panel 16 is provided to the entirety of the strap 10, the panel 16 is in contact with the cheekbones and gives pain to the user. Therefore, by the panel 16 of above shape, contact of the panel 16 with the cheekbones is prevented, or, region of contact could be reduced even in case of the contact occurs, and thus giving pain to the user is prevented.

As for the shape of the strap 10, when the panel 16 is provided, width W3 of a portion of the strap 10 which goes through the buckle 12*a* of the plug 12 and folds back, is preferably configured to be narrower than the width W4 of the portion on which the panel 16 is provided. Then the panel 16 which has the above described shape is provided in the position which does not overlap with the strap 10 which folds back. Thereby, the panel 16 and the strap 10 which folds back can be configured to avoid overlapping each other.

By this means, when the end portion of the strap 10 which goes through the buckle 12*a* and folds back, surface area of the strap 10 is secured to be latched by planate fastener 10*b* which is provided on the end portion of the strap 10. Hence, the flexibility in adjustment of the length of the strap 10 is enhanced. Together with this, the end portion of the strap 10 which folds back and has the planate fastener have positional relation to the panel 16 so as not to overlap, the strap 10 and the panel 16 can be configured so that entire thickness of the strap 10 and the panel 16 can be reduced. Thereby, even when the user lies on the side with the side of his face pressing against a pillow, pain caused by biting of the strap 10 and the panel 16 into the face of the user is prevented.

Figure 17B:
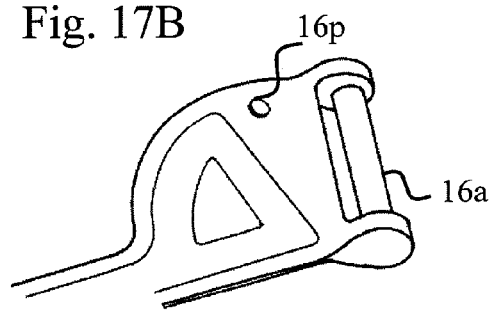

The panel 16 also can be provided with a discriminating means to discriminate between the left and right. For example, as shown by FIG. 17B in an enlarged view of a region of the panel 16 in which the mating portion 16*a* is provided to mate with the breathing mask 8, protrusion 16*p* is provided on the panel 16, by which the left and right are discriminated according to the presence or absence of the protrusion 16*a*, or the number thereof. Alternatively, characters, symbols, or figures can be used as the discriminating means. Thereby, the user can easily discriminate the left and the right of the wearing tool 14 and the breathing mask 8, when the user connects them. By this means, when the user disassemble and clean the wearing tool 14 and reassemble it, efficient and accurate performance is assisted.

Figure 17C:
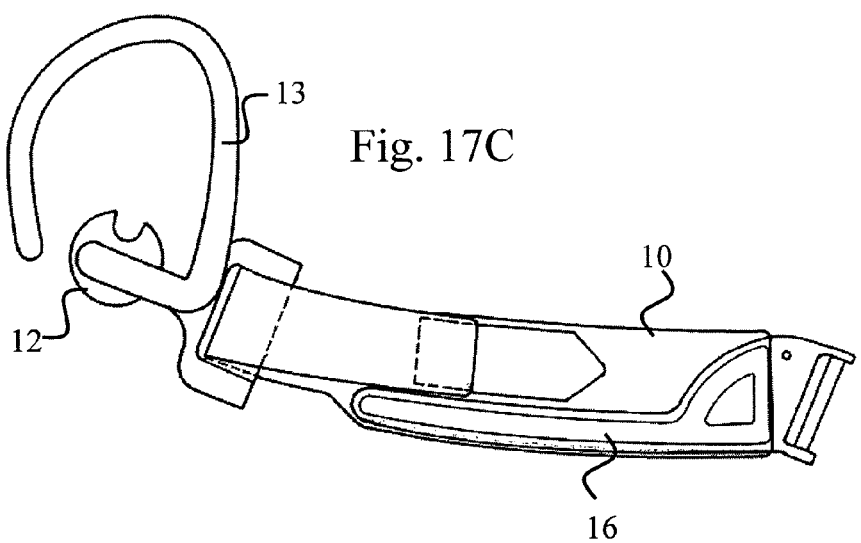

As also shown in FIG. 17C, the panel 16 is applied to the strap 10 in case that the plug 12 and the ear hooking portion 13 are in practice. In this case, in addition to an advantageous result by the ear hooking portion 13 on preventing dropping off of the plug 12, another advantageous result is also achieved by the panel 16 on preventing twist of the strap 10. Hence, the breathing mask 8 can be fixed in close contact with the environs of the nostrils of the user with higher certainty.

FIG. 18 is a drawing for explaining a variation of the panel 16. FIG. 18A through FIG. 18C show examples of the shape of the plane portion 16*b*. As shown in FIG. 18A through FIG. 18C, the plane portion 16*b* can have an arbitrary shape which corresponds to the shape of the plane fastener 10b so that the end of the strap 10, when folding back, does not overlap with the plane portion 16b.

Figure 18A:
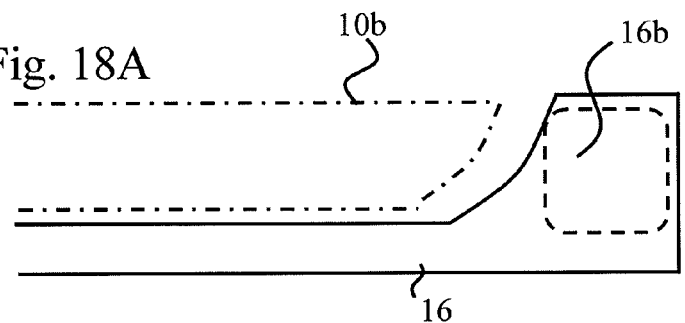
FIG. 18A through FIG. 18D are drawings for explaining a variation of the panel 16.
Figure 18B:
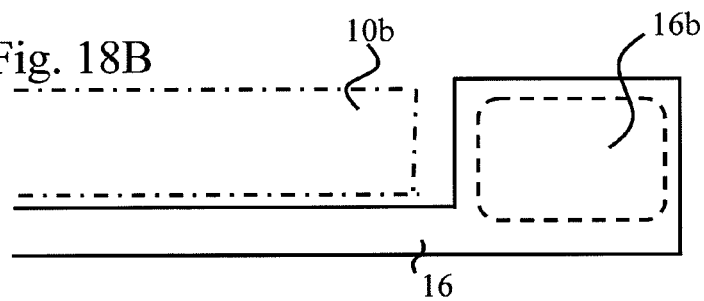
Figure 18C:
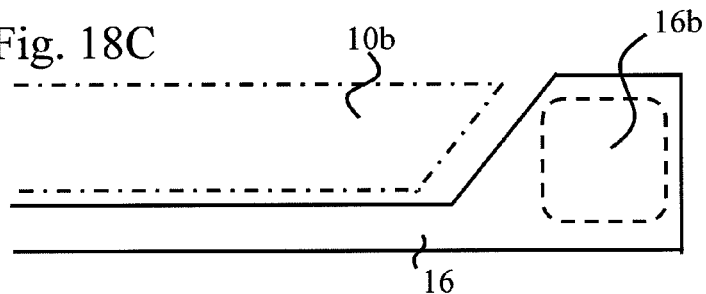
Figure 18D:
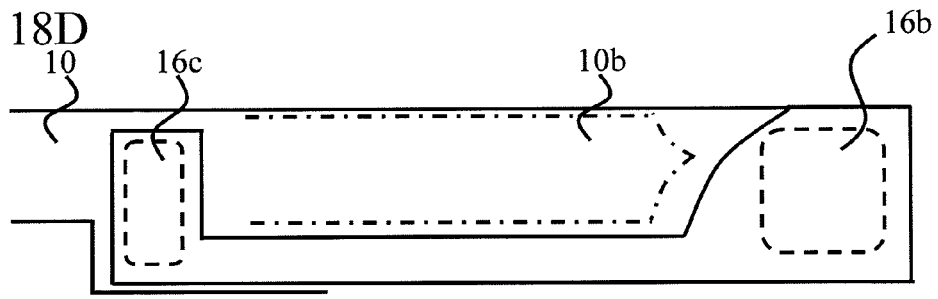

FIG. 18D also shows a shape of the panel 16, which has wider width in the portion close to the end portion which is connected to the plug 12. By means of this shape, plurality of plane portions 16b and 16c can be provided which have widths in the width directions. Therefore, a stress against the force to twist in the width direction can be increased compared with the cases shown by FIG. 17A or FIG. 18A through FIG. 18C. And, by configuring the panel 16 to have shortened width at the center portion in the longitudinal direction, the plane fastener 10b on the end portion of the strap 10 which folds back can latch around the central portion of the strap 10. Consequently, effectiveness is enhanced on preventing twist of the strap 10 without reducing flexibility of adjustment of the length of the strap 10. Contact of the panel 16 with the cheekbones can also be prevented, and thus pain of the user can be reduced. Increase of thickness of the strap 10 and the panel 16 due to overlapping can be prevented. Hence, giving the user a pain due to the strap 10 pressing into the face, when the user lies on the side, can be prevented.

[4] Fourth Embodiment of the Wearing Tool

In the fourth embodiment, the wearing tool 14 has the supporting member provided in the longitudinal direction. This supporting member comprises a first plate-shape member which is fixed to the breathing mask 8 and a second plate-shape member which is fixed to said connecting member. And, the first and the second plate-shape members are configured to be rotatable. The fourth embodiment can be solely practiced, or can be practice with any of wearing tools of the first and the second embodiments, and another the wearing tool. The breathing mask in the practice of the fourth embodiment can be a breathing mask which covers only the environs of the nostrils of the user, or a breathing mask which covers the nostrils and the mouth of the user.

Figure 19A:
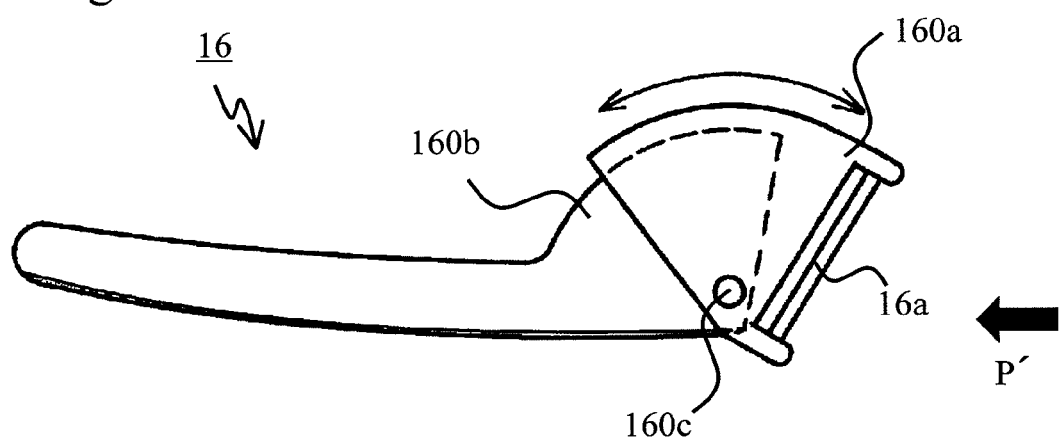
FIG. 19A and FIG. 19B are drawings for explaining the panel 16 as the supporting member.
Figure 19B:
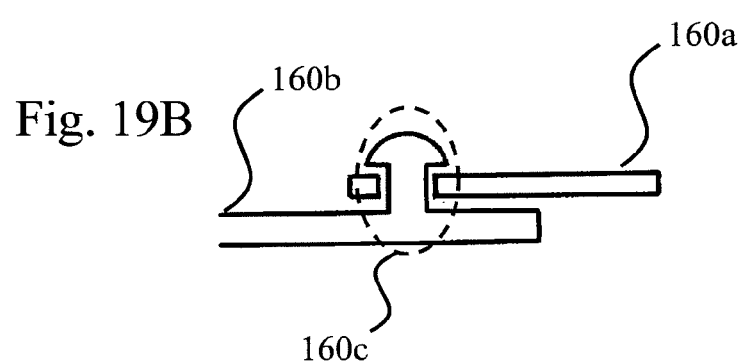

FIG. 19 is a drawing for explaining the panel 16 as the supporting member. FIG. 19A shows a plane view of the right-side panel 16, and FIG. 19B shows a cross-sectional view on an arrow P'. The panel 16 is configured to have the first plate-shape member 160a which has a mating portion 16a to be connected to the breathing mask 8, and the second plate-shape member 160b which is connected to the strap 10. Plate-shape members 160a and 160b are combined each other so that they are rotatable around a rotation axis 160c. The rotation axis 160c is configured with protrusion provided on the plate-shape member 160a (or 160b) and a hole (alternatively a concave or a cutout) with which the protrusion mates, provided on plate-shape member 160b (or 160a). Here, the plate-shape member 160a and overlapping portion of the plate-shape members 160a and 160b are shaped fan-like shape, and the rotation axis 160c is provided in the position of the pivot point of the fan-like shape. In a preferable embodiment, the thickness of each of the plate-shape members 160a and 160b are from 0.1 to 3 millimeters.

In such a configuration, by connecting the plate-shape member 160a to the breathing mask 8, and by connecting the plate-shape member 160b to the strap 10, an angle between the breathing mask 8 and the strap 10 can be changed. Here, since the rotation axis 160c is provided in the position corresponding to the bottom of the nostrils when the user wears the breathing mask 8, adjustment of the angle of the breathing mask 8 is possible with the position of the bottom of the nostrils as a rotation axis. This is explained in FIG. 20.

FIG. 20 is a drawing for explaining function of the fourth embodiment. This embodiment is particularly advantageous when practiced with the breathing mask 8 that covers only the environs of nostril. In FIG. 20, a side face of the user is shown schematically. Here, a case of the nostrils facing upward with an angle of degree α and a case of the nostrils facing downward with an angle of degree β are typically shown, with the horizontal plane as a reference. Assumption is made such that the users have the nostrils which have angle substantially between degree α and degree β.

The breathing mask 8 is desired to cover the nostrils with no gaps occurring at the rim portion which abuts the environs of the nostrils. However, as illustrated, since an angle of the nostrils varies among individuals, an angle of the rim portion of the breathing mask 8, or an angle of the breathing mask 8, is required to be adjusted according to the angle of the nostrils, so that the rim portion of the breathing mask 8 is brought into close contact with the environs of the nostrils. For example, in case that the angle of the nostrils is degree α, the breathing mask 8 is required to be worn with an angle indicated by a dotted line 81, and in case that the angle of the nostrils is degree β, the breathing mask 8 is required to be worn with an angle indicated by a dotted line 82.

In this embodiment, since rotation axis 160c is provided in a position which corresponds to a position Nb of the bottom of the nostrils and plate-shape members 160a and 160b rotate around the position Nb as a rotation axis, an angle of the breathing mask 8 can be adjusted around the position Nb of the bottom of the nostrils as a rotation axis.

This brings an advantageous result as described bellow, compared with the conventional art. In general, when the user wears the breathing mask 8, the length of the strap 10 is firstly adjusted so that a portion of the breathing mask 8, which is required to oppose the bottom of the nostrils (here such a portion is called "nostril bottom-opposing portion"), is in close contact with the bottom of the nostrils. Next, after wearing the breathing mask 8 by the strap 10, confirmation is made on whether the nostril bottom-opposing portion is in close contact with the bottom of the nostril. Here, if the breathing mask 8 is not in close contact with at least a portion of the environs of nostrils, or, to the contrary, compressing hard at least one portion of the environs of nostrils, that is, if an angle of the breathing mask 8 is found inappropriate, by a conventional art which has an angle adjustment mechanism in the center of the vertical direction of the breathing mask 8, the angle of the breathing mask 8 is adjusted with a position Nm as a rotation axis which is distanced from the position Nb of the bottom of the nostrils. Consequently, the nostril bottom-opposing portion is displaced from the bottom of the nostrils, and thus gaps occur at the bottom of the nostril, or, to the contrary, the bottom of the nostrils is pressed hard. Then, the lengths or the wearing position of the straps 10 need to be adjusted again. In this away, since inappropriateness of an angle of the breathing mask 8 is found after adjusting the length of the strap 10, necessity occurs to readjust the length of the strap 10 after adjusting the angle of the breathing mask 8.

With regard to this point, in this embodiment, since the angle of the breathing mask 8 is adjusted with the portion Nb of the bottom of the nostrils as a rotation axis, displacement of the nostril bottom-opposing portion of the breathing mask 8 is prevented. Therefore, even after adjusting an angle of the breathing mask 8, necessity to readjust the length of the strap 10 does not occur. By this means, wearing of the breathing mask 8 accompanied by angle adjustment is facilitated, and convenience for the user is enhanced.

Further, since the angle adjustment mechanism in conventional art has a certain degree of thickness, if the user rolls over and underlies the angle adjustment mechanism, there is the concern for the occurrence of a discomfort feeling due to the face being pressed. With regard to this point, by this embodiment, entirety of angle adjustment mechanism can be configured to be thin, and thus such a discomfort feeling can be prevented.

The panel 16 explained above in the third embodiment is configured so that upper side of a portion in the longitudinal direction is hollowed and has a narrower width than the end portion which is connected to the breathing mask 8. In case of practicing this configuration together with the fourth embodiment, the rotation axis 160*c* on the plate-shape members 160*a* and 160*b* is preferably provided on the bottom portion of the panel 16, that is, on the extended line of the portion of narrower width. Therefore, when rotating plate-shape members 160*a* and 160*b*, rigidity of allover he panel 16 is secured.

Figure 21A:
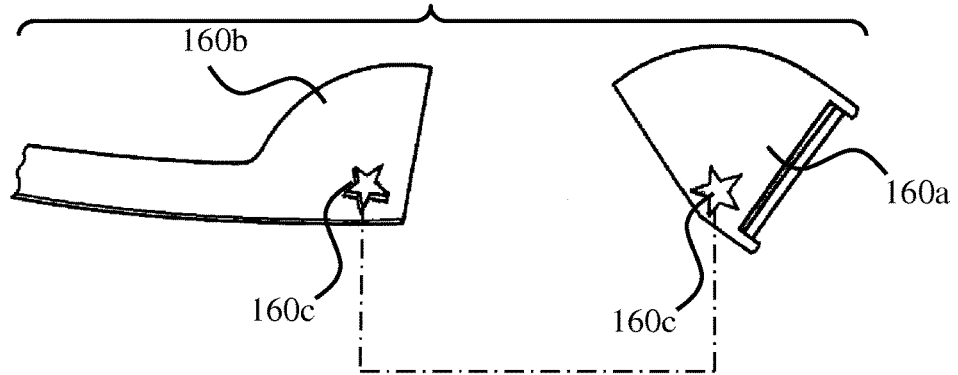
FIG. 21A through FIG. 21C are drawings for explaining a variation of plate-shape members 160a and 160b.
Figure 21B:
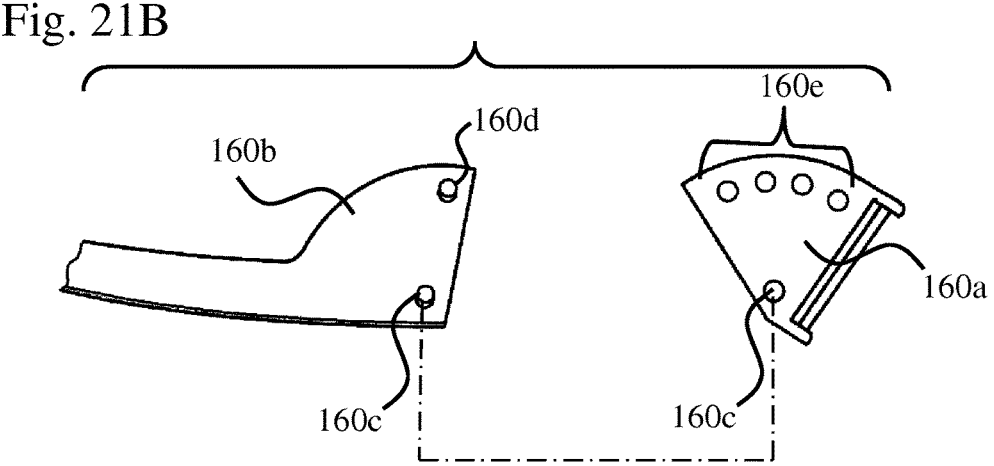
Figure 21C:
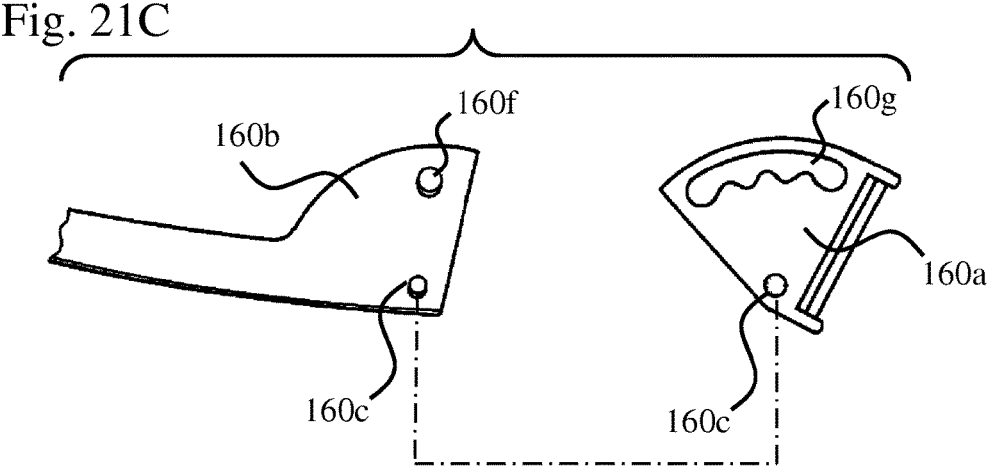

FIG. 21 is a drawing for explaining a variation of plate-shape members 160*a* and 160*b*. In FIG. 21A through FIG. 21C, a fixing means is shown which fixes the rotate position of plate-shape members 160*a* and 160*b* when they are rotated. For example, FIG. 21A shows an example of the fixing means which is configured to be a gear mechanism having the rotation axis 160*c* of star shape, gear shape or the like. In this example, gear shape protrusions provided on the plate-shape member 160*b*, which are arranged on the circular arc around the rotation axis 160*c* as the center, mate with gear shape holes or concave portions corresponding to the rotation axis 160*c* on the plate-shape member 160*b*. And, by mating of the both portions, the rotated position is fixed. And when plate-shape members 160*a* and 160*b* are rotated by a force greater than the force of mating of the gear mechanism, the fixation is released and then mate again at another rotated position. FIG. 21B shows an example of plate-shape member 160*b* having an protrusion 160*d* provided near the circular arc of the plate-shape member 160*b*, and plate-shape member 160*a* having a hole or a concave portion 160*e* provided near the circular arc of the plate-shape member 160*a*. In this example, plate-shape members 160*a* and 160*b* are rotated with the rotation axis 160*c* as a center, and the protrusion 160*d* and the hole or the concave 160*e* mate with each other. Thereby the rotated position is fixed. FIG. 21C shows an example of the fixing means which is configured to have the plate-shape member 160*b* having an protrusion 160*f* provided near the circular arc thereof, while the plate-shape member 160*a* having an arc shaped opening 160*g* provided along the circular arc thereof. In this example, the opening 160*g* of the plate-shape member 160*b* has a wave-formed portion on the rim. When the plate-shape members 160*a* and 160*b* are rotated with the rotation axis 160*c* as the center, the protrusion 160*f* of the plate-shape member 160*b* moves within the opening 160*g* of the plate-shape member 160*a*, and mates with the root portion of the waveform. Hence, the rotate position is fixed.

Figures 22A, 22B:
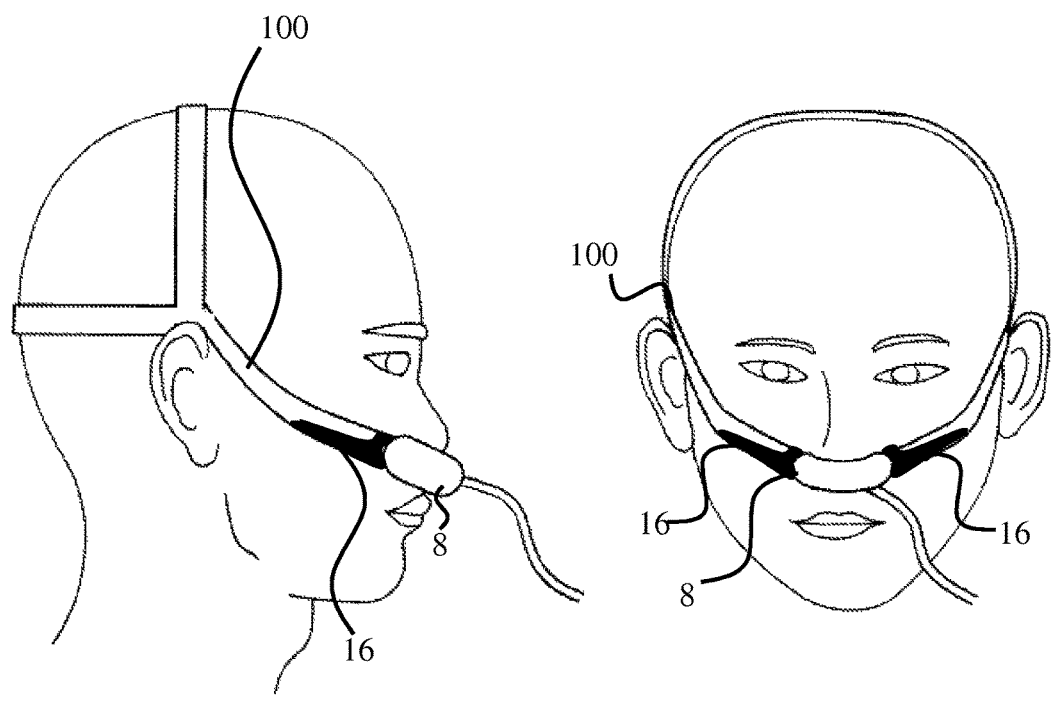
FIG. 22A and FIG. 22B are drawings for explaining an example of the panel 16 of the third or the fourth embodiment being applied to conventional headgear-style wearing tool.

FIGS. 22A and 22B are drawings for explaining an example of the panel 16 of the third or the fourth embodiment being applied to conventional headgear-style wearing tool. The example shown in FIGS. 22A and 22B is an example of headgear-style wearing tool having straps 100 which are connected to both sides of the breathing mask 8 and latch at the back of the head of the user. Each strap 100 is separated into two portions in front of the ear after passing by the cheekbones. And, both ends of the separated portions are jointed in loop-shape on the top and the back of the head of the user, and thus the straps 100 latch around the head of the user.

In such a configuration, if rigid supporting members are provided on entire region of the straps 100 to prevent twist of the strap 100 in the width direction, there is the concern that the supporting members give a pain to the user by a contact with the cheekbones.

Therefore, in achieving an object of preventing such pain and twist of the straps 100, application of the panels 16 of this embodiment to the straps 100 can prevent contact with the cheekbones and thus giving the user pain. And twist of the straps 100 in the width direction can be prevented.

In this way, the third or fourth embodiment can be also applied to a headgear-style wearing tool. That is, the third or the fourth embodiments can provide on the wearing tool (the straps 100 in the above example) the supporting members (the panels 16 in the above example) which are connected to the both sides of the breathing mask 8, and which latch around the head of the user; the supporting members extend in the longitudinal direction of the wearing tool and has rigidity greater than the wearing tool, whereby the width of the supporting member on a portion of the longitudinal direction is narrower than the width of other portions thereof.

Figure 23:
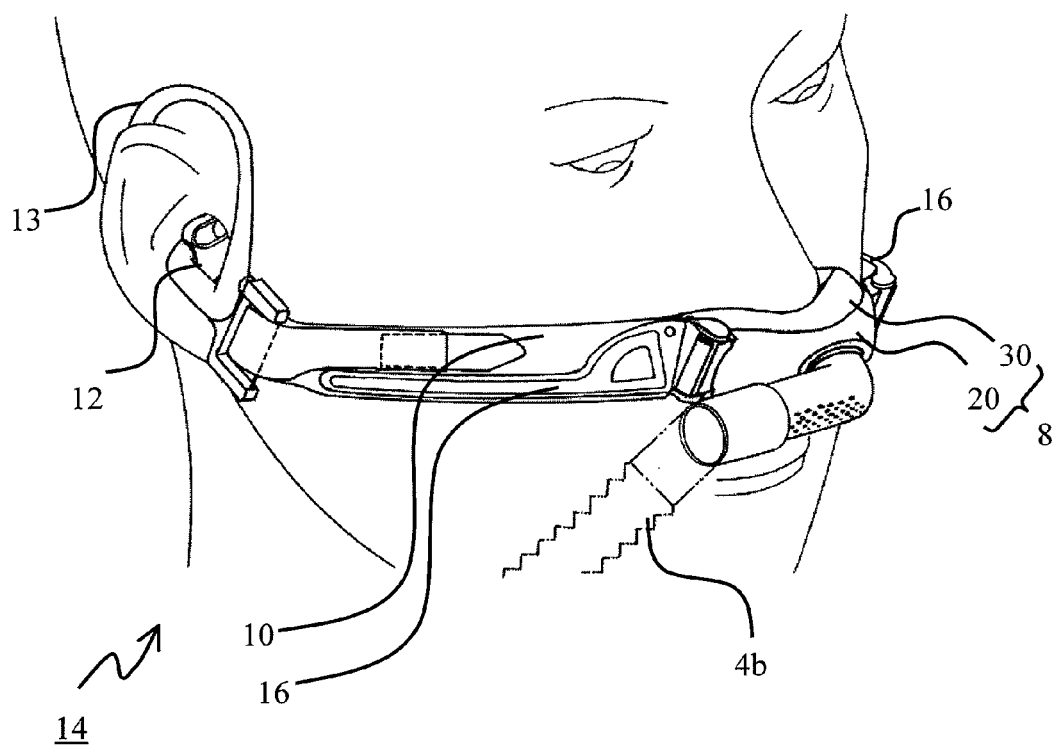
FIG. 23 is a drawing for explaining an example of combination of the wearing tool 14 of the first and the third embodiments.

FIG. 23 is a drawing for explaining an example of combination of the wearing tool 14 of the first and the third embodiments. Here, a using status is shown of the wearing tool 14 having the above mentioned straps 10, plugs 12, ear hooking portions 13, and panels 16. That is, one end portion of the straps 10 are connected to the both sides of the breathing mask 8, and the other end portion of the straps 10 are connected to the plugs 12. And the plugs 12 are plugged in the dimples around the tragi of the user and are fixed. Further, the ear hooking portions 13 are provided on the end portion of the straps 10, and the ear hooking portions 13 latch around the ears.

Further, the panels 16 as supporting members are provided on the straps 10. The panels 16 extend in the longitudinal direction of the straps 10 and have certain degree of widths near the connecting portions with the breathing mask 8, so as to configure a plane portion. By this means, excessive extension and contraction of the strap 10 in the longitudinal direction can be prevented, and also twist in the width direction can be prevented. And the width of a portion which is in contact with the cheekbones is configured to be narrow, and thus the user's pain is prevented.

By the wearing tool 14 configured in this way, a pain or a discomfort feeling which occur when the breathing mask 8 is worn can be reduced, and displacement of the breathing mask 8 is prevented. Further, wearing of the breathing mask 8 can be facilitated.

[5] First Embodiment of Breathing Mask

First, FIG. 23 is used to explain the overall configuration of the breathing mask 8. The breathing mask 8 has a frame 20 which forms the contour and is also connected to the flexible hose 4*b*, and a cushion 30 which is used in combination with the frame 20 and is in contact with the environs of the nostrils of the user to cover it.

Here the configuration of a breathing mask of the prior art is explained, and then this embodiment is explained.

Figure 24:
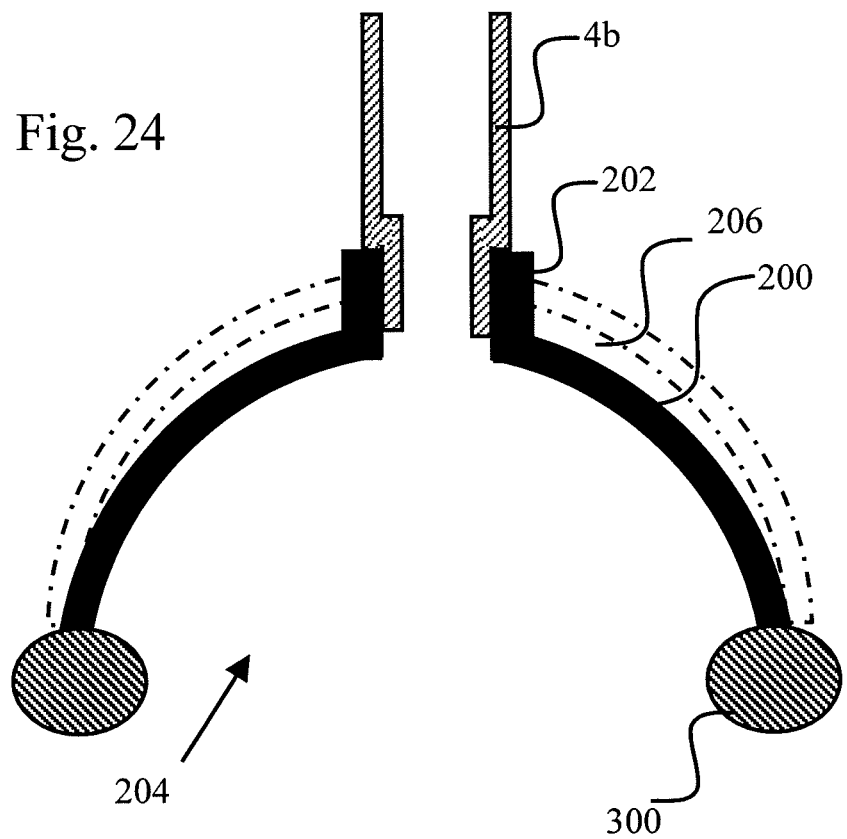
FIG. 24 is a drawing for explaining the configuration of a breathing mask of the prior art.

FIG. 24 is a drawing for explaining the configuration of a breathing mask of the prior art. In FIG. 24, a cross-sectional view of the breathing mask is shown schematically. The bottom of the figure corresponds to the position of the environs of the nostrils of the user lying on the back. In general, a breathing mask has a frame 200 which forms the outer shell of the breathing mask, and a cushion 300 provided on the periphery of the opening portion 204 of the frame 200 and which abuts the environs of the nostrils of the user. The frame 200 has an inhaling port 202, joined to a flexible hose 4*b* which supplies gas for breathing. Here, a case is shown in which the inhaling port 202 is provided vertically above the environs of the nostrils of the user lying on the back.

A breathing mask configured in this way covers the nostrils of the user by means of the opening portion 204, and is fixed in close contact with the environs of the nostrils of the user by a wearing tool. And, gas for breathing, supplied from the inhaling port 202, is sent into the nostrils of the user.

Here, the inhaling port 202 and frame 200 are formed from materials having at least a certain degree of rigidity, such there is no change in shape upon application of an external force or upon occurrence of negative pressure within due to breathing by the user, and such that there is no blocking of the passage used to supply gas for breathing.

On the other hand, in order to send gas for breathing into the nostrils of the user, it is desirable that the frame 200 be in close contact with the face, and that an airtight state be secured. However, if the rigid frame 200 is pressed against the face, pain results, and moreover the shape of the rim of the opening portion 204 of the frame 200 does not necessarily follow the shape of the face for each user, so that there is the concern that gaps may occur. Hence the cushion 300 provided on the rim of the opening portion 202 of the frame 200 should have a certain degree of flexibility and elasticity.

In response to this demand, the frame 200 is for example formed from polycarbonate. And, the cushion 300 is formed from silicone rubber.

However, in CPAP treatment, there are cases in which, in order to avoid excessive drying of the mucous membrane within the nostrils, humidity is added to the gas for breathing using a humidifier 6 as shown in FIG. 1. Further, the breath of the user himself contains moisture. The frame 200 formed of polycarbonate does not have water repellent properties, so that when temperatures are lower, in wintertime or in other circumstances, there are cases in which the humidified gas for breathing and moisture contained in the breath may condense on the inner walls of the frame 200. And, when the user is lying on the back, there is the concern that condensed water drops may grow to a size at which gravitational force cannot be resisted, so that the drops drip onto the face of the user, causing the user to waken.

As a measure to address this condensation, a method of suppressing condensation is proposed in which a heat insulating air layer 206 is provided as a dual structure of the frame 200 as shown by the dot-dash line, to maintain the inner walls of the frame 200 at a temperature higher than that of the outer walls.

However, when blow molding or another highly difficult technique is used for integral molding of the frame 200 of this structure, costs are increased. And when a method is employed in which the inner walls and outer walls are molded separately and combined, the increased number of components and increase in the number of assembly processes entail increased cost.

Hence with the object of providing a breathing mask which is low in cost and able to suppress condensation, the breathing mask of this embodiment is configured as follows.

A breathing mask which covers the nostrils of the user and supplies humidified gas for breathing to the nostrils has a first member (cushion), abutting the face of the user and covering the nostrils and comprising a first port which takes in gas for breathing, and a second member (frame) covering at least a portion of the first member, having a rigidity greater than that of the first member, and comprising a second port connected to a means for transport of the gas for breathing and which mates with the first port portion; a cavity is present between the first member and the second member.

Further, the breathing mask of another aspect has a first member (cushion), abutting the face of the user and covering the nostrils and comprising a first inhaling port which takes in gas for breathing and a first exhaling port which discharges breath, and a second member (frame) covering at least a portion of the first member, having a rigidity greater than that of the first member, and comprising a second inhaling port connected to a means for transport of the gas for breathing and which mates with the first inhaling port portion, and a second exhaling port which mates with the first exhaling port portion and which is connected to the outside; a cavity is present between the first member and the second member.

Further, the breathing mask of a separate aspect has a first member (cushion), abutting the face of the user and covering the nostrils and comprising a first port which takes in gas for breathing, and a second member (frame) covering at least a portion of the first member, having a rigidity greater than that of the first member, and comprising a second port connected to a means for transport of the gas for breathing and which mates with the first port portion; the first member has water repellent properties.

Moreover, the breathing mask of a separate aspect has a first member (cushion) abutting the face of the user and covering the nostrils and comprising a first inhaling port which takes in gas for breathing and a first exhaling port which discharges breath, and a second member (frame) covering at least a portion of the first member, having a rigidity greater than that of the first member, and comprising a second inhaling port connected to a means for transport of the gas for breathing and which mates with the first inhaling port portion, and a second exhaling port which mates with the first exhaling port portion and is connected to the outside; the first member is characterized in having water repellent properties. In a preferred embodiment, the first inhaling port also serves as the first exhaling port, and the second inhaling port also serves as the second exhaling port.

Next, the breathing mask of this embodiment is explained in detail, referring to FIG. 25 through FIG. 33.

Figure 25A:
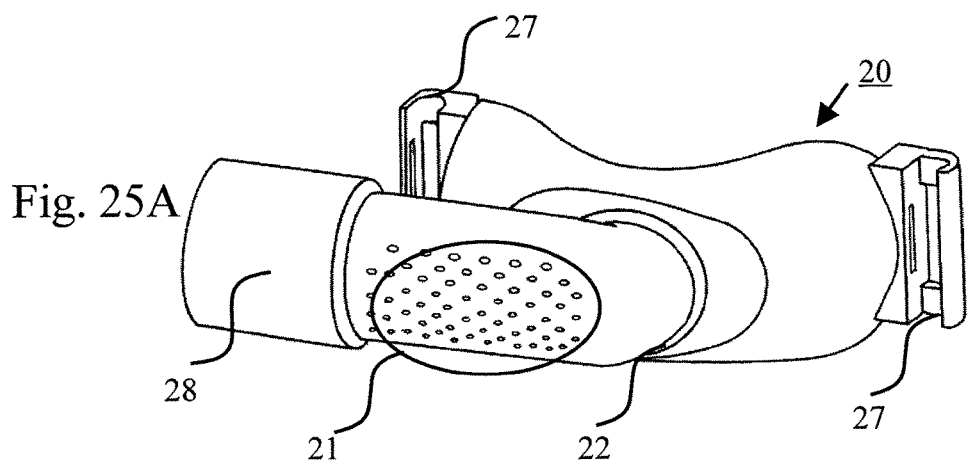
FIG. 25A through FIG. 25C are drawings for explaining the structure of the frame in this embodiment.
Figure 25B:
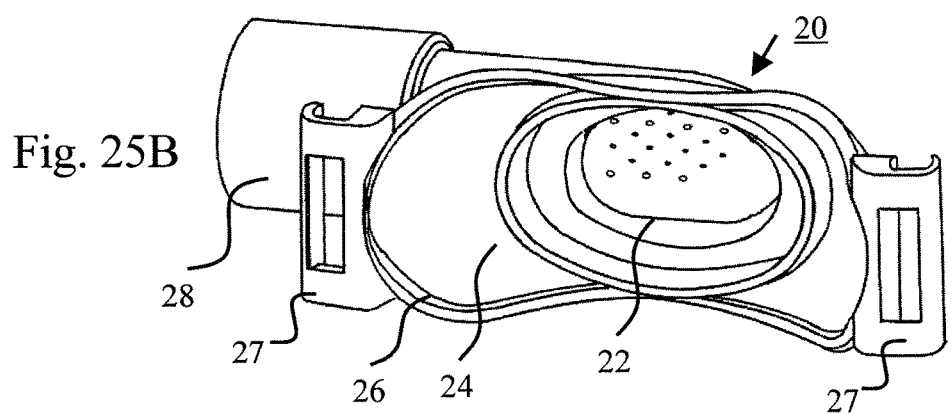
Figure 25C:
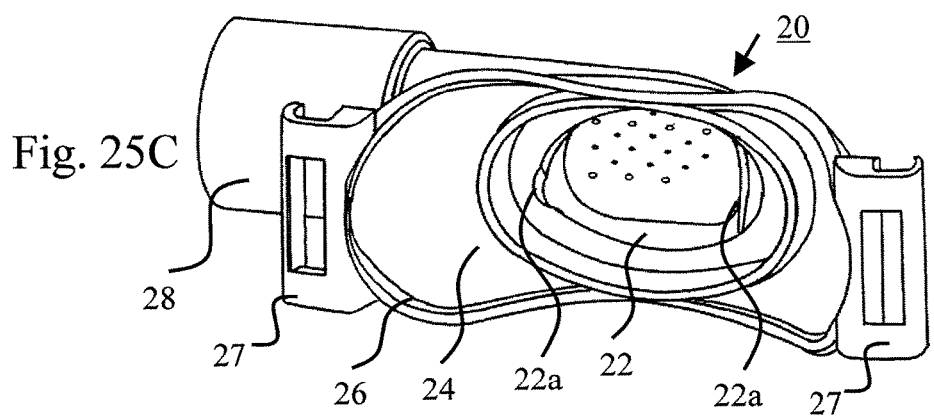

FIG. 25 is a drawing for explaining the structure of the frame in this embodiment. FIG. 25A is a front perspective view of the frame, and FIG. 25B and FIG. 25C show rear perspective views. FIG. 26 shows enlarged views of different portions of the frame.

Figure 26A:
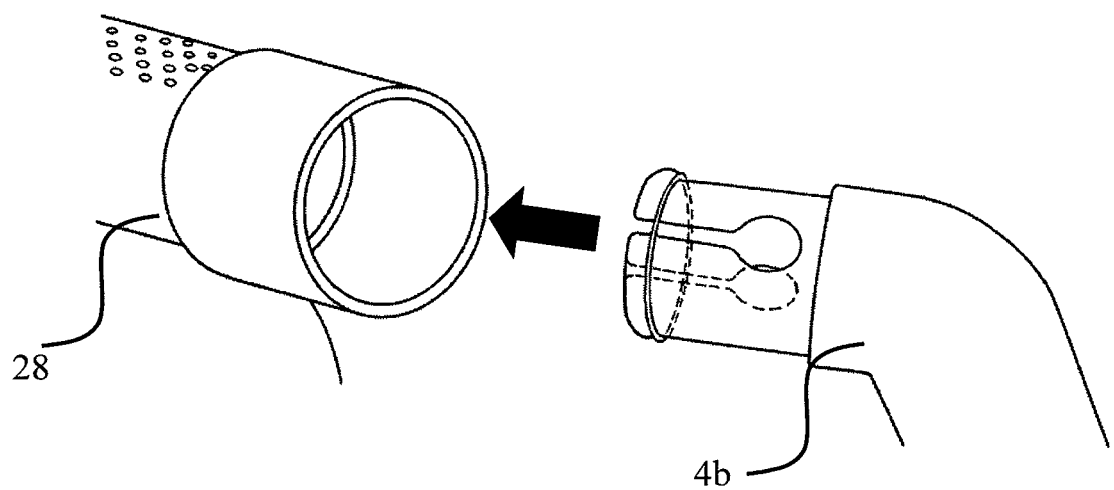
FIG. 26A and FIG. 26B are drawings for showing enlarged views of different portions of the frame.
Figure 26B:
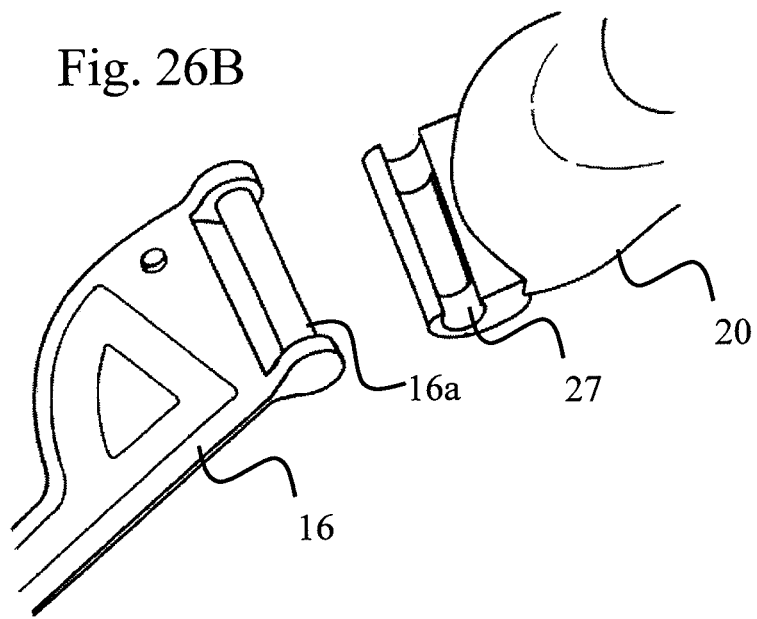

The frame 20 in this embodiment has an opening portion 24 which opposes the user, and an inhale/exhale port 22 which supplies gas for breathing and which discharges breath. The tip of the inhale/exhale port 22 is bent into an L shape, forming an L-shape tube 28. And, as shown in FIG. 26A, the tip end of the L-shape tube 28 is configured to enable mating with a flexible hose 4b. Exhaling holes 21 are provided at places in the inner wall of the L-shape tube 28 opposing the inhale/exhale port 22. By this means, the breath of the user is discharged to the outside of the frame 20. The flexible hose 4b and L-shape tube 28 form a means for transport of gas for breathing.

A concave mating groove 26 is provided in the inner wall of the rim of the opening portion 24, and is configured to enable mating with the cushion 30, as described below. And, as shown in enlargement in FIG. 26B, on both side portions of the frame 20 are provided mating portions 27, which mate with the mating portions 16a of panels 16 provided with straps 10. By this means, the frame 20 is connected with straps 10 at both side portions.

The frame 20 must have degree of rigidity such that deformation under external forces does not readily occur, and can, as one example, be molded integrally from polycarbonate. Integral molding is a preferred embodiment from the standpoints of reducing the number of components and reducing costs.

As shown in FIG. 25C, a pair of plate-shape portions 22a may be formed at positions (for example, the left and right edges) opposing the environs of the inhale/exhale port 22 of the frame 20. By this means, when mated with the inhale/exhale port of the cushion 30 as described below, this can be enclosed and fixed more reliably. Here, semicircular plate-shape portions 22a are shown as one example, but any arbitrary shape can be used, so long as enclosure of the inhale/exhale port of the cushion 30 is possible.

Figure 27A:
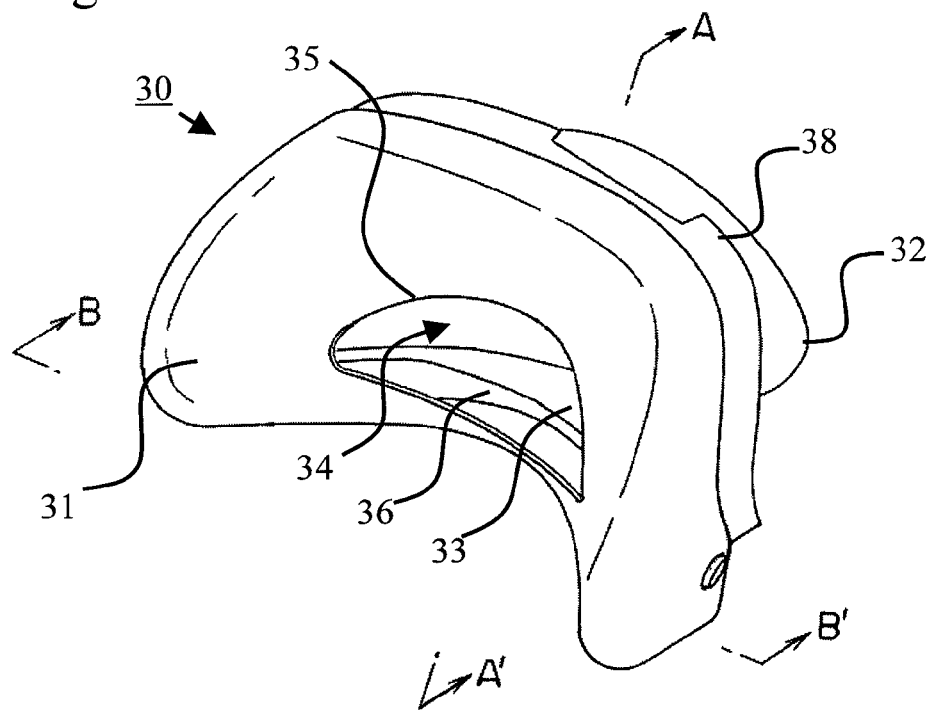
FIG. 27A and FIG. 27B are drawings for explaining the structure of the cushion.
Figure 27B:
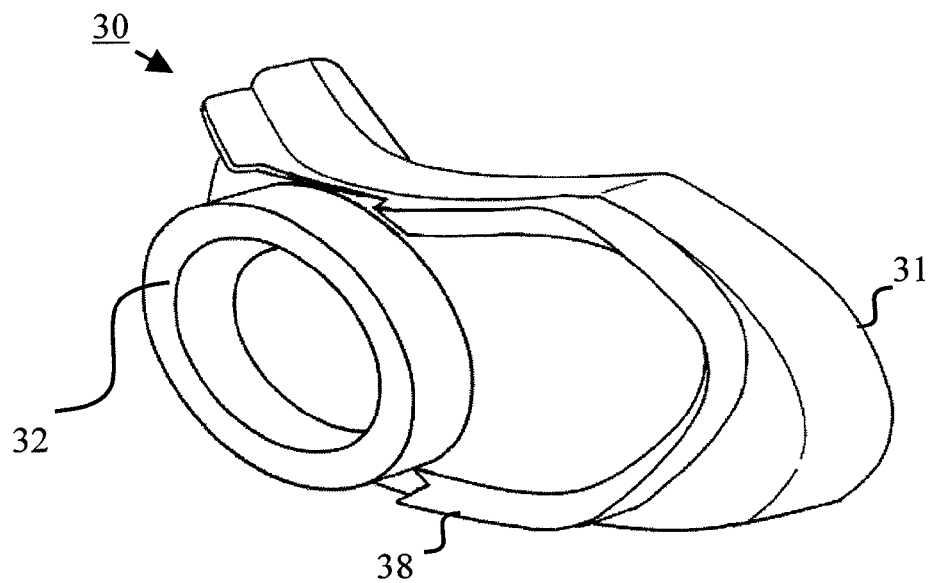
Figure 28A:
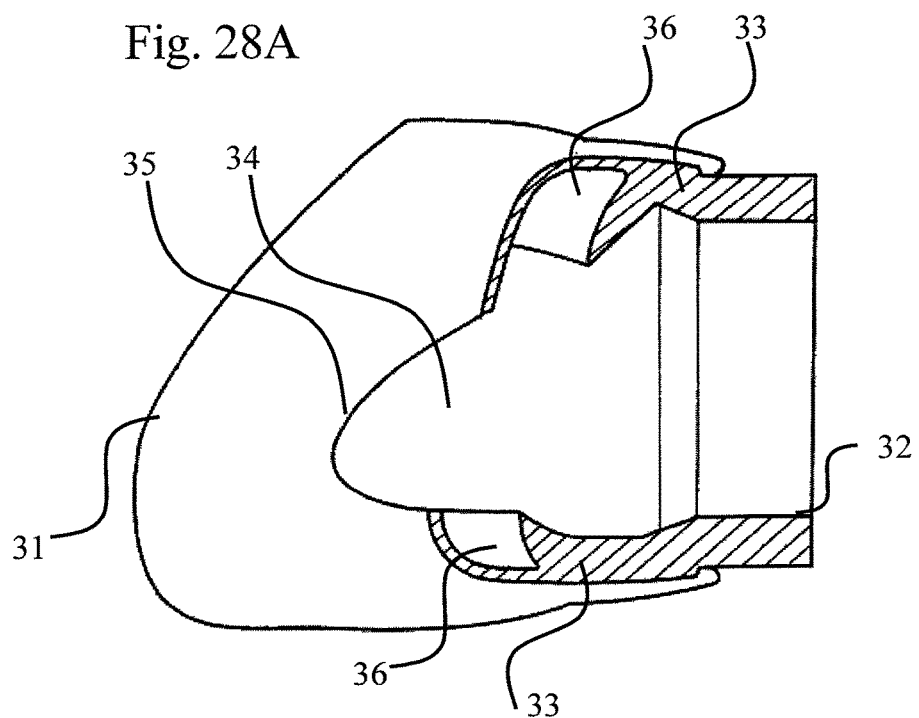
FIG. 28A and FIG. 28B are drawings for showing cross-sections of the cushion 30.
Figure 28B:
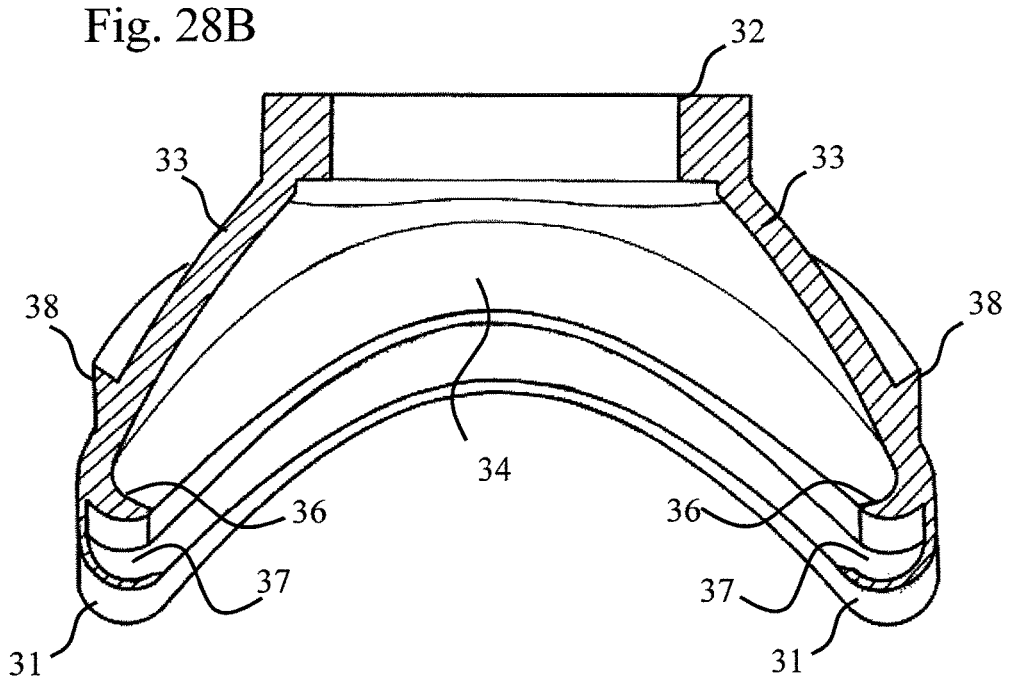

FIG. 27 is a drawing for explaining the structure of the cushion. FIG. 27A is a front perspective view of the cushion, and FIG. 27B is a rear perspective view. Also, FIG. 28 shows cross-sections of the cushion. FIG. 28A shows a cross-section of the cushion 30 in the plane AA' in FIG. 27A, and FIG. 28B shows a cross-section of the cushion 30 in the plane BB' in FIG. 27A. The cushion 30 in this embodiment comprises a first membrane (abutting portion) 31, which abuts the face of the user, an inhale/exhale port 32 which mates with the inhale/exhale port 22 of the frame 20, and an intermediate portion 33 which connects the abutting portion 31 and the inhale/exhale port 32. The abutting portion 31, inhale/exhale portion 32, and intermediate member 33 form an internal space 34, and gas for breathing is supplied to this internal space 34 from the inhale/exhale port 22 of the frame 20.

A oval-shape opening portion 35 connecting to the internal space 34 is formed in substantially the center of the abutting portion 31, and the nostrils of the user face the internal space 34 with this opening portion 35 intervening. The region of contact between the abutting portion 31 and the face of the user extends over the range, in the vertical direction of the face of the user, from the tip of the nose to the upper lip, and in the lateral direction, between both cheeks. Hence the abutting portion 31 makes contact only the environs of the nostrils, which are comparatively insensitive to discomfort resulting from contact and pressure by foreign objects. Consequently there is no contact of the cushion 30 with the sensitive nasal bridge or environs of the eyes, and a good field of vision can be secured, while preventing a situation in which itching, inflammation and similar occur due to long-term use.

Further, the abutting portion 31 is formed to be thin using a material having a degree of flexibility and elasticity, as well as biocompatibility, such as for example silicone rubber. Hence when the gas for breathing is supplied under pressure to the internal space 34, the first membrane 31 expands outward, and makes close contact with the face of the patient. Consequently there is no leaking of the gas for breathing from between the abutting portion 31 and the face of the user, and the occurrence of strange noises due to gas leakage as well as stimulation of the eyes and similar can be prevented. Further, even when the wearing tool 14 is tightened to fasten the breathing mask 8 to the face of the user, the contact pressure applied by the abutting portion 31 to the face of the patient is relaxed, so that a satisfactory wearing sensation results.

Further, a second membrane 36 is provided integrally between the abutting portion 31 which is the first membrane and the intermediate portion 33 in the cushion 30. This second membrane 36 protrudes on the inside of the internal space 34, and moreover is formed in a ring shape along the abutting portion 31. And, the second membrane 36, intermediate portion 33, and inhale/exhale port 32 are formed to be thick compared with the abutting portion 31 which is the first membrane, as shown in FIG. 28A, and have a certain degree of rigidity. Hence even when the breathing mask 8 is placed in close contact with the face of the patient, the shape of the cushion 30 can be maintained in a satisfactory shape, and moreover the second membrane 36 presses the abutting portion 31 from the inside, so that the force of close contact of the abutting portion 31 with the face of the user can be further increased. In particular, it is preferable that the rim portion of the opening portion 35 in the abutting portion 31 be formed extending to the inside of the inner rim portion of the second membrane 36. In this case, only the flexible abutting portion 31 abuts the face of the user, so that a more satisfactory wearing sensation can be obtained. Further, by means of this configuration, a pocket 37 which can hold water drops is formed on the inside of the abutting portion 31 and the second membrane 36, as described in detail below.

Further, the second membrane 36, intermediate portion 33, and inhale/exhale port 32 may each be formed using different materials; but from the standpoint of reducing the number of components and reducing costs, it is preferable that these be formed integrally using the same material as used in the abutting portion 31.

On the other hand, a convex mating edge 38, which can mate with the mating groove 26 provided in the inner wall of the opening portion rim of the frame 20, is provided integrally on the outside of the intermediate portion 33 in the cushion 30.

Figure 29A:
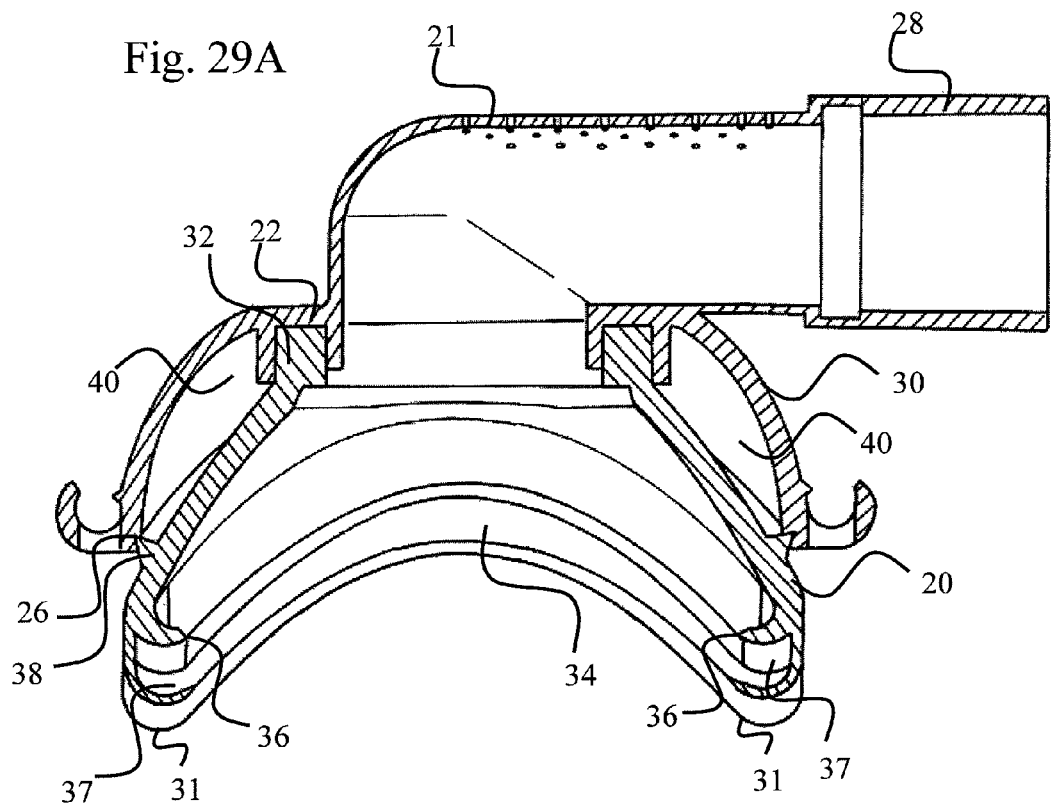
FIG. 29A and FIG. 29B are drawings for showing cross-sectional views of the state in which the frame 20 and cushion 30 are mated.

FIG. 29 shows cross-sectional views of the state in which the frame 20 and cushion 30 are mated. FIG. 29A shows the cross-section at the plane BB' in FIG. 27A. The inhale/exhale portion 32 of the cushion 30 is mated with the inhale/exhale portion 22 of the frame 20, and the mating edge 38 of the cushion 30 is mated with the mating groove 26 of the frame 20. By this means, the frame 20 and cushion 30 are mated at two places. Further, by molding the frame 20 in advance such that the outer wall is formed in a shape which swells outward, a cavity 40 is formed between the frame 20 and the cushion 30.

Through the functioning of this cavity 40 as a heat insulating air layer, the temperature within the cushion 30 can be maintained at a temperature higher than the temperature outside the frame 20, and condensation within the cushion 30 can be suppressed. In order to enhance the air tightness of the cavity 40, a gel or other adhesive may be applied between the mating groove 26 on the side of the frame 20 and the mating edge 38 on the side of the cushion 30. By this means, the heat insulation effect of the cavity 40 can be enhanced, and condensation can be suppressed more reliably.

Further, in the above configuration the mating groove 26 on the side of the frame 20 and the mating edge 38 on the side of the cushion 30 can be mated and fixed, so that when the wearing tool 14 is tightened and the breathing mask 8 is brought into close contact with the face of the patient, pressing of the cushion 30 into the frame 20 can be prevented. Hence blocking of the cavity 40 can be prevented. Also, when the cushion 30 is formed from silicone rubber or another flexible material, upon supplying gas for breathing under pressure, the intermediate portion 33 and similar expand slightly; in this case also, the mating groove 26 and mating edge 38 are mated, so that the occurrence of shifts in position between the frame 20 and the cushion 30 can be prevented. And, the contact pressure when wearing the breathing mask 8 to the user can be relaxed through the action of expansion of the abutting portion 31, and in addition, by forming the convex mating edge 38 of silicone rubber or similar, similarly to the other portions of the cushion 30, the mating edge 38 acts as a cushion which relaxes the pressure. Hence the wearing sensation felt by the user can be further improved.

In place of providing a concave mating groove 26 and a convex mating edge 38, the same action and advantageous results can be obtained by a configuration in which mutually joinable steps are provided on the periphery or a portion of the frame 20 and cushion 30. That is, the frame 20 and cushion 30 can be joined and fixed, so that the air tightness of the cavity 40 is enhanced, and when the wearing tool 14 is tightened and the breathing mask 8 is brought into close contact with the face of the patient, pressing of the cushion 30 into the frame 20 can be prevented. Hence blocking of the cavity 40 can be prevented. Even when the intermediate portion 33 of the cushion 30 expands due to the pressurized gas for breathing, shifts in position between the frame 20 and cushion 30 can be prevented. Further, by joining the cushion 30 with the frame 20, it acts as a cushion which relaxes pressure, and the wearing sensation felt by the user can be further improved.

Figure 29B:
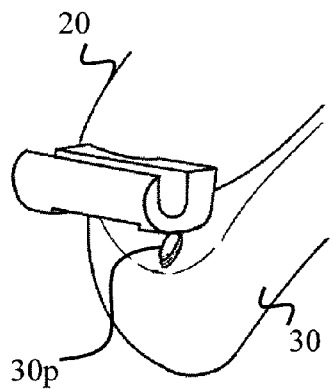

As shown in FIG. 29B, a protrusion 30p to discriminate between the right and left of the cushion 30 can be provided, so that right and left are discriminated according to the presence or absence of a protrusion, and the number thereof. Or, as the means of discrimination, characters, symbols, or figures may be provided apart from protrusions. By this means, right and left can easily be discriminated when connecting the cushion 30 and the frame 20. Hence when the breathing mask 8 is disassembled and cleaned, and the user once again assembles the mask, assistance can be provided for efficient and accurate assembly.

Here, the advantageous results of this embodiment are explained, through comparison with an example of the prior art. First, in the prior art example shown in FIG. 24, the frame 200 and cushion 300 are configured as separate members formed from different materials, and in a breathing mask 8 employing these in combination, a heat insulating air layer is formed by employing a dual structure for the frame 200. On the other hand, in this embodiment shown in FIG. 25 through FIG. 29, the frame 20 and cushion 30 are configured as separate members formed using different materials, and a cavity 40 can be formed as a heat insulating air layer when these are used in combination, so that condensation can be suppressed using a smaller number of components and fewer manufacturing processes.

Further, in the above configuration, the entire inner walls of the breathing mask 8 are formed by the cushion 30, so that the water repellent properties of silicone rubber can be applied to the entirety of the inner walls. Hence even when small-diameter water drops occur due to condensation within the cushion 30, because of the small adsorptive force with the cushion 30, the drops can be discharged to the outside by the airflows of the gas for breathing supplied to the mask, the breath of the patient, and similar before the drops grow to a large enough diameter to drip onto the face of the user, and so dripping of water drops onto the face of the user can be prevented. And, because exhaling holes 21 are provided near the inhale/exhale port 32, that is, near the inhale/exhale port 22 on the side of the frame 20, discharge of moist air can be promoted. Hence the more rapid evaporation of water drops can be promoted.

Here, if when the user is lying on the back there are scattered places above the environs of the nostrils which do not have water repellent properties, then there is an increased probability that water drops which have condensed at these places will grow and drip onto the face of the user. By employing the above configuration, the inner walls of the cushion 30 having water repellent properties, the inhale/exhale port 32, the inhale/exhale port 22 of the frame 20, and the inner wall portions of the L-shape tube 28 in which the exhaling holes 21 are provided, are positioned vertically above the environs of the nostrils of the user lying on the back. Here, the inner walls of the L-shape tube 28 do not have water repellent properties, but by providing the exhaling holes 21, the probability of occurrence of condensation at such places, or the probability of growth to a large diameter of water drops which have condensed, can be made small. In this way, even should condensation occur on the inner walls of the cushion 30, the water drops can be discharged to the outside from the exhaling holes 21 via the inhale/exhale ports 32, 22 by the airflows of the gas for breathing supplied to the mask, by the breath of the patient, and similar, before growing to large diameter. Hence the probability that water drops above the environs of the nostrils of the user will grow is made small, and wakening due to dripping of water drops can be prevented.

Further, in order to enhance the closeness of contact at the environs of the nostrils of the user, the abutting portion 31 is curved in the lateral direction overall, and is formed with the rim portion of the opening portion 35 in the abutting portion 31 extending to the inside from the inner rim portion of the second membrane 36, so that when worn with the user lying on the back, even if condensed water drops travel along the inner walls of the cushion 30 and fall, a pocket 37 capable of holding the water drops is formed on the inside of the abutting portion 31 and in the second membrane 36. And, by making the shape of the abutting portion 31 a shape which is curved in the lateral direction, the pocket 37 has a shape which broadens downwards, so that the accumulated water drops can be held reliably. It is preferable that a sponge, absorbent gel, or other water-absorbing material be comprised in the pocket 37, so that water drops can be held with high certainty. Hence falling of water drops onto the face of the user and wakening of the user can be prevented with higher certainty.

As another embodiment, the frame 20 and the cushion 30 may have separate inhaling ports and exhaling ports.

Figure 30:
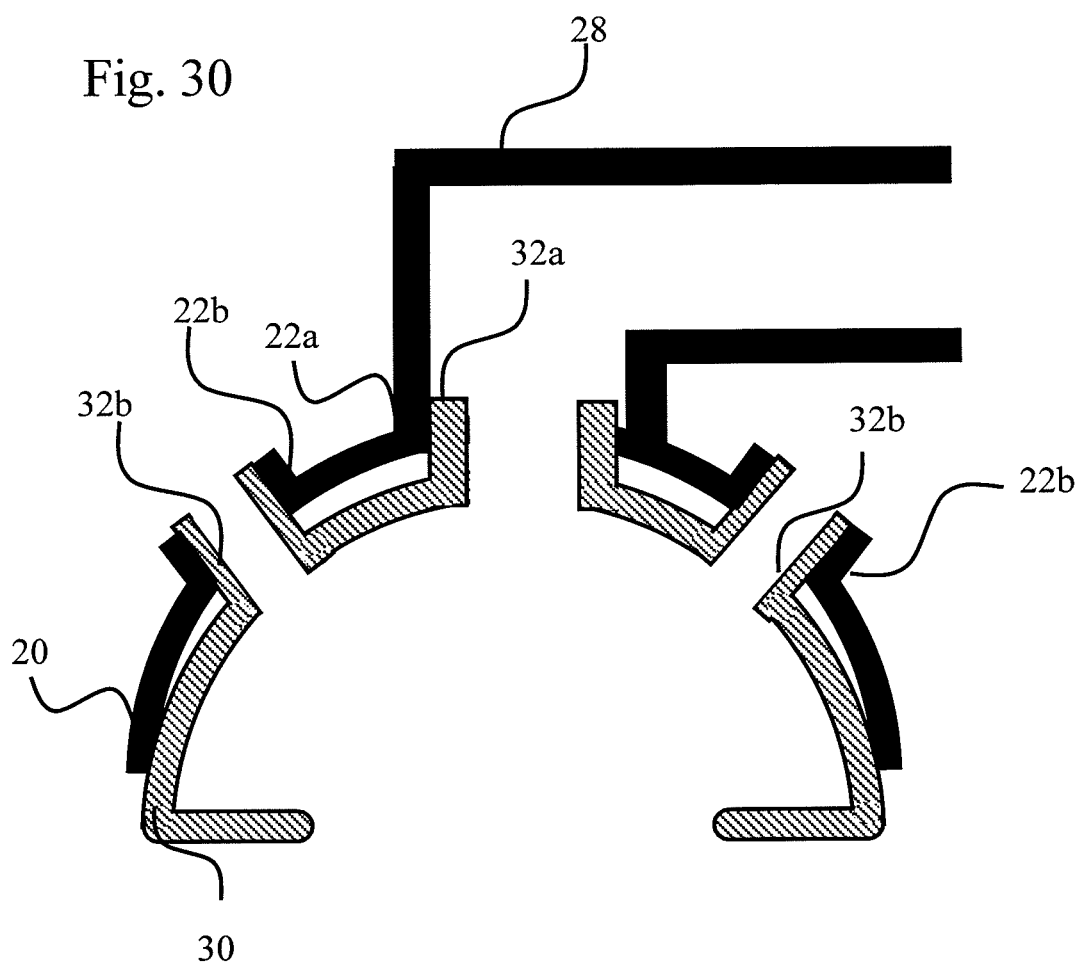
FIG. 30 is a drawing for showing an example of the configuration of a frame 20 and cushion 30 having separate inhaling ports and exhaling ports.
Figure 31A:
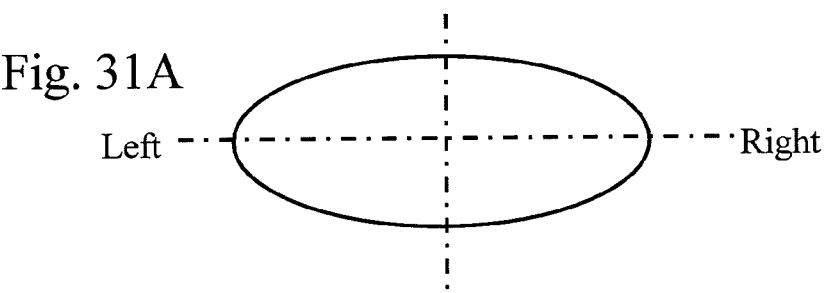
FIG. 31A through FIG. 31D are drawings for explaining examples of the shapes of the mating portions of the frame 20 and cushion 30.
Figure 31B:
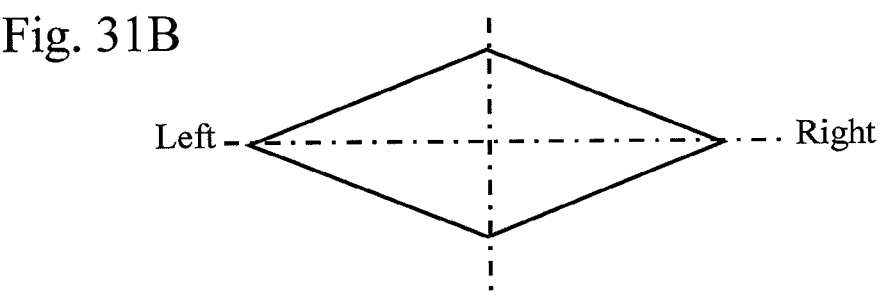
Figure 31C:
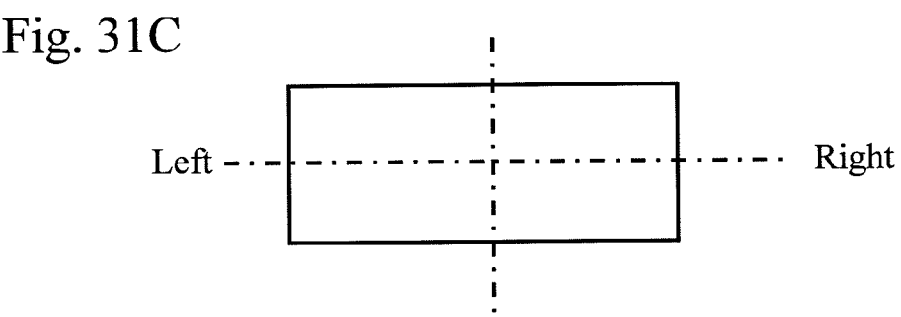
Figure 31D:
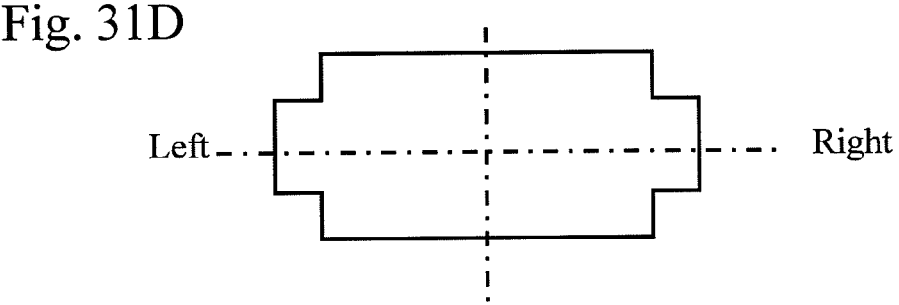

FIG. 30 shows an example of the configuration of a frame 20 and cushion 30 having separate inhaling ports and exhaling ports. In this configuration, the inhaling port 32a and exhaling port 32b of the cushion 30 are provided so as to enable mating with the inhaling port 22a and exhaling port 22b of the frame 20, respectively. And, the exhaling port 32b portion of the cushion 30 is formed from silicone rubber having water repellent properties similar to the entire cushion 30. Hence even should condensation occur within the cushion 30, evaporation will be caused before growing into water drops large enough to fall, and moist air can be discharged outside the mask from the exhaling port 32b. Hence falling of condensed water drops and wakening of the user can be prevented.

Here, a case is shown in which two exhaling ports 22b, 32b are provided, but the number and placement of exhaling ports are not limited to those of this example.

Further, in this case also, by forming a cavity 40 between the frame 20 and the cushion 30 as a heat insulating air layer, the advantageous result described above of suppressing condensation can be obtained.

[6] Second Embodiment of Breathing Mask

In a second embodiment of a breathing mask, by integrally molding and providing the L-shape tube 28 on the frame 20, the number of components of the breathing mask 8 and costs can be reduced. And, the mating portions of the frame 20 and cushion 30, that is, the inhale/exhale ports 22, 32, mating groove 26, and mating edge 38, are formed in shapes having 180° rotational symmetry. Together with this, the portions 27 mating with the panels 16 provided on the frame 20 and straps 10 are formed in shapes having 180° rotational symmetry. By this means, the breathing mask 8 can be configured such that the direction of the tip portion of the L-shape tube 28 may be directed to the left or to the right, according to the preference of the user, and can be worn by the wearing tool 14. By this means, the breathing mask 8 can be worn with the flexible hose 4b directed in advance in the direction in which there is little concern that, when the user is lying on the side, the flexible hose 4b will be crushed by the body. Hence crushing of the flexible hose 4b and hindrance of the supply of gas for breathing can be prevented.

FIG. 31 is a drawing for explaining examples of the shapes of the mating portions of the frame 20 and cushion 30. The examples of shapes shown in FIG. 31 are examples of shapes of the inhale/exhale port 22 of the frame 20 and inhale/exhale port 32 of the cushion 30, or examples of shapes of the mating groove 26 of the frame 20 and the mating edge 38 of the cushion 30. The examples shown in FIG. 25 through FIG. 29 correspond to the elliptical shape in FIG. 31A. In addition, for example a diamond shape (FIG. 31B), rectangular shape (FIG. 31C), or other irregular shapes (FIG. 31D), or any other arbitrary shapes having 180° rotational symmetry, can be used. Here a true circle, a square shape, and other shapes with 90° rotational symmetry are also included; but if a shape with 90° rotational symmetry is used, then mating is also possible with the lateral directions of the frame 20 and the cushion 30 rotated by 90°, and so in order to prevent such errors in assembly, shapes with 180° rotational symmetry are preferred.

Further, the shapes of the inhale/exhale port 22 and mating groove 26 on the side of the frame 20, and of the inhale/exhale port 32 and mating edge 38 on the side of the cushion 30, may respectively be the same shapes, or may be different shapes. By means of this configuration, when the user assembles the breathing mask 8, the direction of the L-shape tube 28 can be directed to either the left or to the right, so that freedom of selection is secured, and in addition no errors are made in the vertical direction. Hence accurate assembly can be performed.

Thus by means of this embodiment, freedom in the direction of connection of the frame 20 and flexible hose 4b can be secured at low cost, and convenience to the user can be enhanced.

Figure 32:
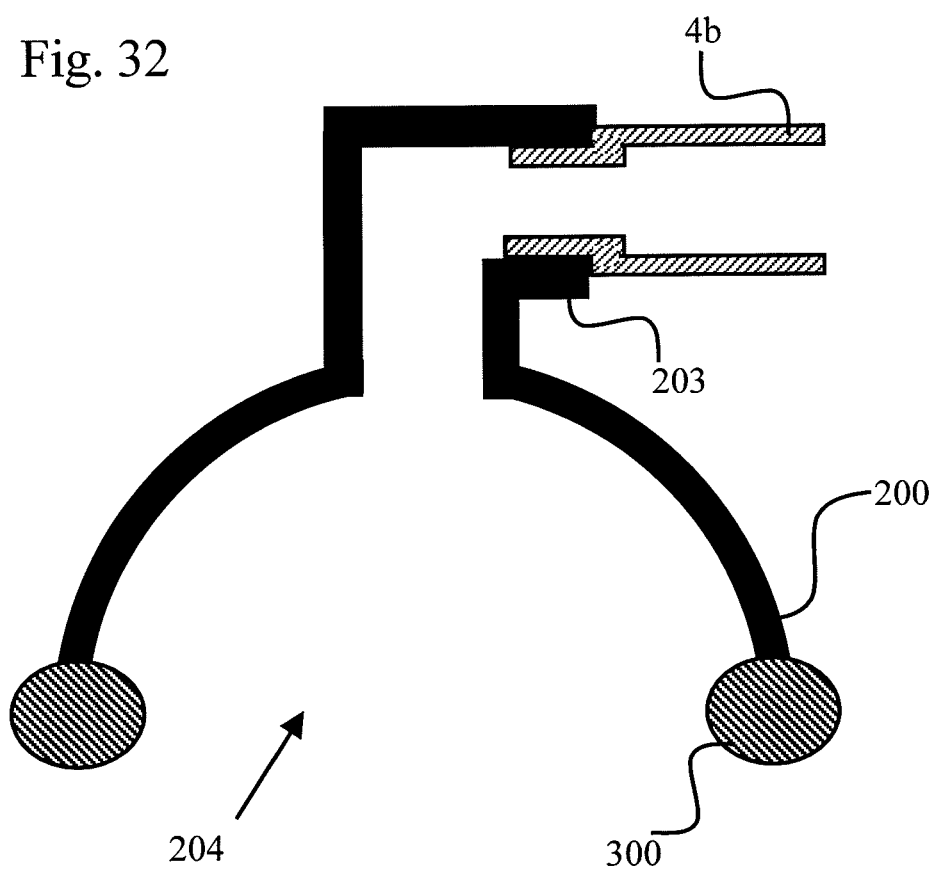
FIG. 32 is a drawing for explaining an example of a conventional breathing mask to which the frame 20 and cushion 30 are applied.

Further, an embodiment in which the shapes of the mating portions of the frame and cushion have 180° rotational symmetry as described above can also be applied to a breathing mask configured with a conventional frame and cushion, as shown in FIG. 32. Here, in contrast with the case of FIG. 24, the inhaling port 203 forms an L-shape tube directed in a lateral direction.

In this case, in a breathing mask 8 having a frame 200 forming the shell of the breathing mask and a cushion 300 provided on the rim of the opening portion 204 of the frame 200 and which abuts the environs of the nostrils of the user, the frame 200 and cushion 300 are configured to enable attachment and removal. For example, the rim of the opening portion of the frame 200 and the cushion 300 are configured to enable mating. Here, by making the shapes of the mating portions of the rim of the opening portion of the frame 200 and the cushion 300 shapes with 180° rotational symmetry as described above, the direction of connection of the inhaling port 203 forming the L-shape tube can be either to the right or to the left. That is, freedom in the direction of connection of the frame 20 and the flexible hose 4b can be secured, and accurate assembly is made possible. Hence convenience to the user can be enhanced.

FIG. 33 is a drawing for explaining a practical example relating to the combination of the mating portion 27 of the frame 20 and the mating portion 16a of the panel 16. In FIG. 33A, a schematic plane view of the frame 20 and the left and right panels 16 is shown. For convenience, here the right and left in the plane of the paper are associated with the right and left of the frame 20 and panels 16 in the explanation. Also, here a case is explained in which the mating portions 16a on the sides of the panels 16 have a columnar shape, whereas the mating portions 27 on the side of the frame 20 have a groove shape (shown in solid black) which mate therewith; but the mating portions 16a and 27 may have the opposite shapes.

In this practical example, the mating portions 27 of the frame 20 and the mating portions 16a of the panels 16 have 180° rotational symmetry, and vertically are not symmetric. For example, a configuration is employed in which a cone-shape portion 16r is provided on the upper end of the mating portion 16a on the left side, and a cone-shape portion 16r' is provided on the lower end of the mating portion 16a on the right side, and the mating portions 27 have shapes corresponding thereto.

By means of this configuration, first the mating portions 27 of the frame 20 and the mating portions 16a of the panels 16 have 180° rotational symmetry, so that when the entire frame 20 is rotated to change the direction of the L-shape tube 28, either of the mating portions 27 can be mated with the mating portions 16a of the left and right panels 16. However, if an attempt is made to erroneously mount the frame 20 and panels 16 with the front and rear reversed, the mating shapes of the mating portions 27 and 16a do not match, so that assembly is not possible. If the panels 16 are assembled with the front and rear erroneous, the panels 16 abut the cheeks of the user, and there is the concern that discomfort may occur; but by means of this practical example, such a situation can be prevented. Further, when marks are provided to indicate front and rear, the user must confirm the marks each time. However, by means of this practical example, erroneous assembly is not possible, so that errors in assembly can easily be prevented.

Figure 33A:
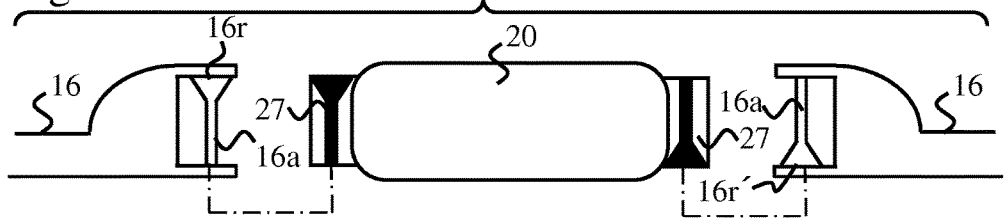
FIG. 33A through FIG. 33E are drawings for explaining a practical example relating to the combination of the mating portion 27 of the frame 20 and the mating portion 16a of the panel 16.
Figure 33B:
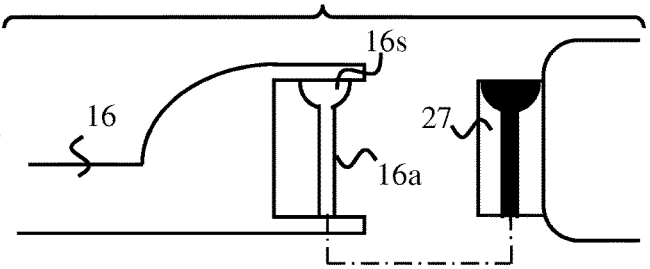
Figure 33C:
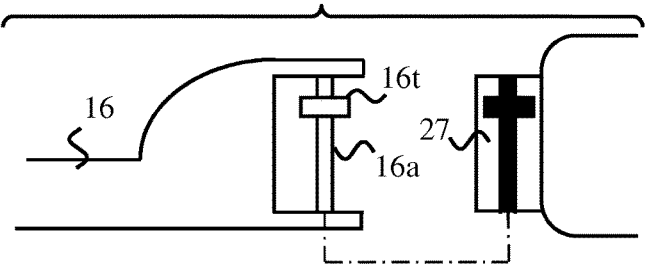
Figure 33D:
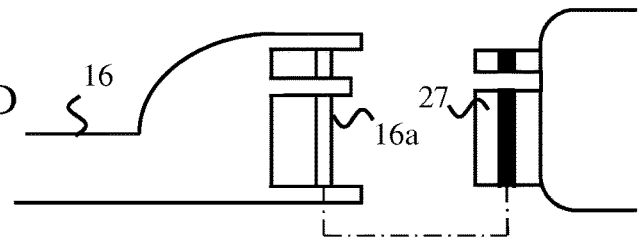
Figure 33E:
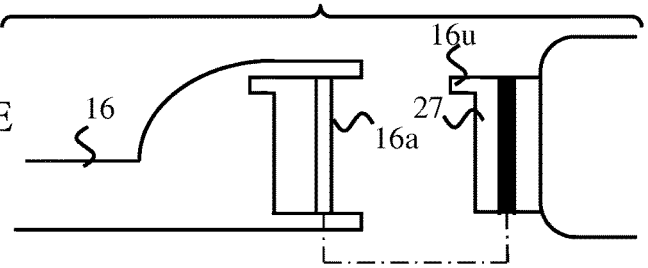

FIG. 33B through FIG. 33E show other modified examples. For convenience, in FIG. 33B through FIG. 33E only the left-side mating portions 16a and 27 are shown. FIG. 33B is an example in which, in place of cone shapes, portions 16s with a hemispherical shape are provided at the upper ends of the mating portions 27, 16a. FIG. 33C is an example in which a disc-shape portion 16t is provided at a position toward the upper end from the center of the mating portion 16a, and an opening corresponding thereto is provided in the mating portion 27. FIG. 33D is an example in which the mating portions 27 and 16a are divided into upper and lower, and the upper and lower lengths are made different. FIG. 33E is an example in which a flange-shaped convex portion 16u is provided in the direction perpendicular to a columnar groove in the upper end of the mating portion 27, and an opening corresponding thereto is provided on the side of the mating portion 16a.

A breathing mask 8 having the frame 20 and cushion 30 of the first and second embodiments of breathing masks may be used with the wearing tool 14 in the first through fourth embodiments of wearing tool described above, or may be used with wearing tool other than the wearing tool 14, such as for example a conventional headgear-type wearing tool. In all these cases, a breathing mask which suppresses condensation on the inside can be realized at low cost. Further, even if condensation occurs, falling of water drops resulting from condensation onto the face of a user while asleep to cause wakening can be prevented. Further, a breathing mask can be realized at low cost which can prevent a situation in which, because the user is lying on the side, the flexible hose 4b is crushed by the body, impeding the flow of gas for breathing.

Further, the wearing tool 14 in the first through fourth embodiments of wearing tool described above can be used not only in CPAP treatment for sleep apnea syndrome, but also in other applications. For example, use as the wearing tool of an oxygen mask for first aid procedures in emergencies is possible. In this case, wearing can be performed more quickly and more easily than in the case of headgear designs which latch around the perimeter of the head of the user. Or, the wearing tool 14 in the first through fourth embodiments of wearing tool, and the breathing masks 8 in the first and second embodiments of breathing masks, can also be applied to NIPPV (Non-invasive Positive Pressure Ventilation) treatment, which is one ventilatory failure treatment method in which a gas for breathing, pressurized to approximately 392 to 1961 Pa, is supplied intermittently to the environs of the nostrils of the user. In the NIPPV treatment method, the user must fasten a breathing mask not only while sleeping, but during the daytime as well. Hence the wearing tool 14 of the first through fourth embodiments of wearing tool, and the breathing masks 8 of the first and second embodiments of breathing masks, are suitable for use to reduce the pain and discomfort attending prolonged wearing of the breathing mask, and to suppress condensation and prevent the growth of water drops.

As explained above, by the present invention, the breathing mask can be fixed at the environs of the nostrils of the user, and together with this, a pain and a discomfort feeling brought by wearing can be reduced. Also, displacement of the breathing mask can be prevented. Further, by the present invention, when the breathing mask is worn, adjustment according to the structure of the nose of the user is enabled, and wearing of the breathing mask is facilitated. Further, by the present invention, condensation of the breathing mask can be suppressed at low cost. And, by the present invention, the breathing mask which can prevent interference with the supply of gas for breathing is realized at low cost.

DESCRIPTION OF NOTES

2: BREATHING GAS SUPPLY APPARATUS 4a, 4b: FLEXIBLE HOSE 6: HUMIDIFIER 8: BREATHING MASK 10: STRAP 12: PLUG 13: EAR HOOKING PORTION 13a: FRAME PORTION 13b: BIASING PORTION 14: WEARING TOOL 16: PANEL 160a, 160b: PLATE-SHAPE MEMBER 20: FRAME 21: EXHALING HOLES 22: INHALE/EXHALE PORT 24: OPENING PORTION 26: MATING GROOBE 28: L-SHAPE TUBE 30: CUSHON 31: ABUTING PORTION 32: INHALE/EXHALE PORT 35: OPENING PORTION 37: POCKET 38: MATING EDGE

What is claimed is:

1. A wearing tool for a breathing mask which covers nostrils of a user and supplies gas for breathing to the nostrils comprising:
   a pair of connecting members each of which has a longitudinal shape, and has a first end portion which is connected to the breathing mask; and
   a pair of fixing members each of which is connected to a second end portion of each of the pair of connecting members respectively, and is configured with a plate piece extending in a longitudinal direction that is anteroposterior direction of the user,
   wherein the plate piece has a first latching portion having a curved surface adapted to latch in a first dimple inside a tragus of the user, and has a second latching portion having a curved surface adapted to latch in a second dimple inside an antitragus of the user, the second latching portion is in a position substantially opposing the first latching portion in the longitudinal direction of the plate piece, the first latching portion has a shape curving towards entrance of an ear canal, and the second latching portion has a shape curving in the opposite direction of the first latching portion.

2. The wearing tool according to claim 1, wherein each of the pair of fixing members is connected to each of the pair of connecting members respectively at a position center line in width direction of the connecting member.

3. The wearing tool according to claim 1, wherein each of the pair of fixing members comprises a hole or a cutout in a position corresponding to an ear canal of the user.

4. The wearing tool according to claim 1, wherein each of the pair of fixing members further comprises an inserting portion which is adapted to insert in the ear canal of the user.

5. The wearing tool according to claim 4, wherein the inserting portion is deformable according to the ear canal of the user.

6. The wearing tool according to claim 4, wherein the inserting portion of each of the pair of fixing members has a prescribed angle relative to a center of each of the respective pair of fixing members.

7. The wearing tool according to claim 4, wherein the center of the inserting portion of each of the pair of fixing members is in a deviated position from a center of each of the respective pair of fixing members.

8. The wearing tool according to claim 1, wherein each of the pair of fixing members further has a third latching portion which is adapted to latch in a third dimple inside an incisura intertragica of the user.

9. The wearing tool according to claim 8, wherein each of the pair of fixing members has, on the third latching portion, a surface which curves along the shape of the third dimple.

10. The wearing tool according to claim 1, wherein each of the pair of fixing members has a portion which has elasticity between the first latching portion and the second latching portion.

11. The wearing tool according to claim 1, wherein the fixing member has an elastic material in the second latching portion.

12. The wearing tool according to claim 1, wherein each of the pair of fixing members has a portion which is connected to the second end portion of each of the pair of connecting members respectively, and which can tilt.

13. The wearing tool according to claim 1, wherein each of the pair of connecting members is connected, on the second end portion, with a latching member which is adapted to latch around an ear of the user.

14. The wearing tool according to claim 13, wherein the latching member has a first portion which has a diameter different from a diameter of a second portion other than the first portion.

15. The wearing tool according to claim 14, wherein the first portion is a portion which is close to a tip end of the latching member.

16. The wearing tool according to claim 1, wherein
each of the pair of connecting members further comprises a supporting member which extends in the longitudinal direction of the connecting member, and which has a greater rigidity than that of the connecting member, and
the supporting member has a first width on a first region close to the first end portion, and a second width, which is narrower than the first width, on a second region other than the first region.

17. The wearing tool according to claim 1, wherein
the first latching portion has a diameter larger than the second latching portion.

18. A breathing mask comprising the wearing tool according to claim 1.

19. A wearing tool for a breathing mask which supplies a user with gas for breathing comprising:
a pair of connecting members each of which has a longitudinal shape and has a first end portion which is connected to the breathing mask; and
a pair of frame portions, each of which is connected to a second end portion of each of the pair of connecting members; wherein
each of the pair of frame portions comprises:
a first portion having a first end connected to the second end portion of one of the pair of connecting members and adapted to be placed around the outer circumference of the ear flap of the user, and the first portion being not pressed between the ear flap and a head of the user when the user lies on the side, the entire first portion having an inner radius larger than the entire outer circumference of the ear flap; and
a biasing portion which is connected to a second end of the first portion and is adapted to bias the base of the ear of the user in a forward direction of the user, and a diameter of the biasing portion being configured to be smaller than a diameter of a part of the first portion, the part of the first portion being positioned along the biasing portion;
wherein each of the pair of connecting members has a strap and a supporting member, wherein said supporting member comprises a first plate-shape member which is fixed at the breathing mask, and a second plate shape member which is fixed at the strap, wherein the first plate-shape member and the second plate-shape member are configured to be rotatable around a rotation axis which is provided at a position on an extended line of the second region of the supporting member.

20. The wearing tool according to claim 19, wherein each of the pair of frame portions curves in substantially U-shape.

21. The wearing tool according to claim 19, wherein a tip end of the biasing portion is apart from the first portion.

22. The wearing tool according to claim 19, further comprising a pair of fixing members each of which is connected to the second end portion of each of the pair of connecting members, and is adapted to plug in a tragus of the user.

23. The wearing tool according to claim 19, wherein the first portion circumvents the environs of the ear flap of the user.

24. A breathing mask comprising the wearing tool according to claim 19.

25. A wearing tool for a breathing mask which covers nostrils of a user and supplies pressurized gas for breathing to the nostrils comprising:
a pair of connecting members each of which has a longitudinal shape and has a first end portion, which is connected to the breathing mask, and a second end portion at the opposite end of the first end portion, which is connected to each of a pair of fixing portions, and which is adapted to fix the breathing mask at the environs of the nostrils of the user and is adapted to pass on a cheek of the user; wherein
each of the pair of connecting members has
a strap having a longitudinal shape and being located between the first end portion and the second end portion and
a supporting member provided on the strap, extending in the longitudinal direction of the strap, and having greater rigidity than that of the strap,
the supporting member of said each of the pair of connecting members has
a first region having a first width and being located to the first end portion and
a second region extending from the first region toward the second end portion and having a second width, which is narrower than the first width, and
the strap of said each of the pair of connecting members is adapted to pass on cheekbones of the user at a position parallel to the second region and the second region of the supporting member is adapted to pass below the cheekbones and be prevented from passing on the cheekbones;
wherein said supporting member comprises a first plate-shape member which is fixed at the breathing mask, and a second plate shape member which is fixed at the strap, wherein the first plate-shape member and the second plate-shape member are configured to be rotatable around a rotation axis which is provided at a position on an extended line of the second region of the supporting member.

26. The wearing tool according to claim 25, further comprising the pair of fixing members each of which is connected to the second end portion of each of the pair of connecting members and is adapted to plug in a dimple inside a tragus of the user, wherein
the length of each of the pair of connecting members can be adjusted by the second end portion of the connecting member folding back and latching at the center portion of the connecting member, and
said each of the supporting members is provided in a position of each of the pair of connecting members which does not overlap with the second end portion which folds back.

27. The wearing tool according to claim 25, further comprising a fixing element provided on the first plate-shape member and the second plate-shape member, which fixes a position of the rotation of the first plate-shape member and the second plate-shape member.

28. A breathing apparatus comprising:
a breathing mask having a third width and adapted to cover nostrils and peripheral area of the nostrils of a user and supply gas for breathing to the nostrils; and
a wearing tool connected to the breathing mask,
wherein the wearing tool comprises:
a pair of connecting members each of which has a longitudinal shape and has a first end portion which is connected to the breathing mask, and a second end portion at the opposite end of the first end portion; wherein each of the connecting members has
- a strap having a longitudinal shape and being located between the first end portion and the second end portion and
- a supporting member provided on the strap, extending in the longitudinal direction of the strap, and having greater rigidity than that of the strap, the supporting member further comprises a first plate-shape member which is fixed at the breathing mask and has a first width and a second-plate shape member which is fixed on the strap and has a second width, the first plate-shape member and the second plate-shape member are rotatably connected with each other at a rotational axis so that the first plate-shape member and the second plate-shape member are rotatable with respect to each other, and the rotational axis is provided at the bottom end portion of the first plate-shape member and in a direction of the second width of the second plate-shape member, and the position of the bottom end portion in the first width and the second width corresponds to the position of a bottom end portion in the third width of the breathing mask.

29. The breathing mask according to claim 28, wherein the thickness of the first plate-shape member and the second plate-shape member is from 0.1 millimeters to 3.0 millimeters.

30. The breathing mask according to claim 28, further comprising, on the first plate-shape member and the second plate-shape member, a fixing element which fixes a position of the rotation of the first plate-shape member and the second plate-shape member.

31. The breathing mask according to claim 30, wherein
the first plate-shape member and the second plate-shape member have substantially fan-like shape having the rotation axis as a pivot, and
the fixing element is provided in the region around the arc of the fan-like shape.

32. The breathing mask according to claim 31, wherein
the fixing element comprises:
a plurality of holes placed along an arc of either of the first plate-shape member or the second plate-shape member, and
a protrusion which is provided on the other of the first plate-shape member or the second plate-shape member, and which can latch at any of the plurality of holes.

33. The breathing mask according to claim 31, wherein the fixing element comprises:
a hole which has a cutout on its rim and is provided in a region around an arc of the fan-like shape of either of the first plate-shape member or the second plate-shape member, and
a protrusion which can move within the hole and can latch at the cutout, and which is provided in the other of the first plate-shape member or the second plate-like member.

34. The breathing mask according to claim 31, wherein the fixing element comprises a gear mechanism which is provided at the rotation axis.

* * * * *